(12) United States Patent
Schaeffer et al.

(10) Patent No.: US 9,895,055 B2
(45) Date of Patent: Feb. 20, 2018

(54) MEDICAL DEVICES, SYSTEMS, AND METHODS FOR THE VISUALIZATION AND TREATMENT OF BODILY PASSAGES

(71) Applicants: Cook Medical Technologies LLC, Bloomington, IN (US); Cook Biotech Incorporated, West Lafayette, IN (US)

(72) Inventors: Darin Schaeffer, Bloomington, IN (US); Charlie Agnew, West Lafayette, IN (US); Arun Mohan, West Lafayette, IN (US); Thomas Cherry, Covington, LA (US); Pamela Ridgley, Bloomington, IN (US); Daniel Dalenberg, Portage, MI (US); Kathryn Evert, Bloomington, IN (US); Ken Kennedy, Clemmons, NC (US)

(73) Assignees: COOK MEDICAL TECHNOLOGIES LLC, Bloomington, IN (US); COOK BIOTECH INCORPORATED, West Lafayette, IN (US)

( * ) Notice: Subject to any disclaimer, the term of this patent is extended or adjusted under 35 U.S.C. 154(b) by 556 days.

(21) Appl. No.: 14/191,535

(22) Filed: Feb. 27, 2014

(65) Prior Publication Data

US 2014/0243615 A1    Aug. 28, 2014

Related U.S. Application Data

(60) Provisional application No. 61/770,405, filed on Feb. 28, 2013.

(51) Int. Cl.
*A61B 1/005* (2006.01)
*A61B 1/267* (2006.01)
(Continued)

(52) U.S. Cl.
CPC .............. *A61B 1/267* (2013.01); *A61B 1/005* (2013.01); *A61B 1/0051* (2013.01);
(Continued)

(58) Field of Classification Search
CPC ............ A61B 1/00039; A61B 1/00041; A61B 1/00043; A61B 1/00045; A61B 1/00048;
(Continued)

(56) References Cited

U.S. PATENT DOCUMENTS 2,649,092 A    8/1953    Wallace
3,521,620 A    7/1970    Cook
(Continued)

FOREIGN PATENT DOCUMENTS

CA    2403030 A1    3/2003
EP    2368481 A1    9/2011
(Continued)

OTHER PUBLICATIONS

International Bureau of WIPO, "International Report on Patentability," for Int. App. No. PCT/US2014/018878, dated Sep. 11, 2015, pp. 1-9.
(Continued)

*Primary Examiner* — Ryan Henderson
(74) *Attorney, Agent, or Firm* — Buchanan Van Tuinen LLC

(57) ABSTRACT

Medical devices are described herein. More particularly, the disclosure relates to medical devices, systems, and methods for the visualization and treatment of bodily passages, such as an airway, sinus cavity, or sinus passages. An exemplary medical device comprises an elongate member, an actuator moveable between an actuator first position and an actuator second position, and a wire member. The elongate member has a first straight, or substantially straight configuration, when the actuator is in the actuator first position and a
(Continued)

second curved configuration when the actuator is in the actuator second position.

20 Claims, 23 Drawing Sheets

(51) Int. Cl.
*A61B 5/00* (2006.01)
*A61B 1/233* (2006.01)
(52) U.S. Cl.
CPC ............ *A61B 1/0057* (2013.01); *A61B 1/233* (2013.01); *A61B 1/2673* (2013.01); *A61B 1/2676* (2013.01); *A61B 5/4806* (2013.01); *A61B 5/4818* (2013.01)
(58) Field of Classification Search
CPC .............. A61B 1/0005; A61B 1/00055; A61B 1/00071; A61B 1/00135; A61B 1/00142; A61B 1/00154; A61B 1/005; A61B 1/0051; A61B 1/0052; A61B 1/0053; A61B 1/0055; A61B 1/0056; A61B 1/0057; A61B 1/0058; A61B 1/008; A61B 1/01; A61B 1/04; A61B 1/041; A61B 1/042; A61B 1/043; A61B 1/045; A61B 1/05; A61B 1/051; A61B 1/053; A61B 1/055; A61B 1/24; A61B 1/247; A61B 1/267; A61B 1/2673; A61B 1/2676; A61B 5/4806; A61B 5/4808; A61B 5/4812; A61B 5/4815; A61B 5/4818
USPC ................ 600/114, 115, 121–125, 127, 129, 600/139–152; 604/95.01–95.05, 528, 604/540, 541
See application file for complete search history.

(56) References Cited

U.S. PATENT DOCUMENTS

| | | |
|---|---|---|
| 3,625,200 A | 12/1971 | Muller |
| 4,726,374 A | 2/1988 | Bales et al. |
| 4,790,812 A | 12/1988 | Hawkins et al. |
| 4,826,087 A | 5/1989 | Chinery |
| 4,886,067 A | 12/1989 | Palermo |
| 5,125,395 A | 6/1992 | Adair |
| 5,308,318 A | 5/1994 | Plassche, Jr. |
| 5,380,305 A | 1/1995 | Ghouri |
| 5,441,483 A | 8/1995 | Avitall |
| 5,447,503 A | 9/1995 | Miller |
| 5,460,616 A | 10/1995 | Weinstein et al. |
| 5,477,860 A | 12/1995 | Essen-Moller |
| 5,489,278 A | 2/1996 | Abrahamson |
| 5,509,900 A | 4/1996 | Kirkman |
| 5,522,400 A | 6/1996 | Williams |
| 5,534,007 A | 7/1996 | Germain et al. |
| 5,642,736 A | 7/1997 | Avitall |
| 5,643,171 A | 7/1997 | Bradshaw et al. |
| 5,658,301 A | 8/1997 | Lamaitre et al. |
| 5,674,197 A | 10/1997 | van Muiden et al. |
| 5,685,858 A | 11/1997 | Kawand |
| 5,718,684 A | 2/1998 | Gupta |
| 5,738,664 A | 4/1998 | Erskine et al. |
| 5,769,821 A | 6/1998 | Abrahamson et al. |
| 5,807,398 A | 9/1998 | Shaknovich |
| 5,865,800 A | 2/1999 | Mirarchi et al. |
| 5,908,403 A | 6/1999 | Bosma et al. |
| 5,916,214 A | 6/1999 | Cosio et al. |
| 5,938,582 A | 8/1999 | Ciamacco et al. |
| 5,954,050 A | 9/1999 | Christopher |
| 5,989,241 A | 11/1999 | Plishka et al. |
| 6,033,378 A | 3/2000 | Lundquist et al. |
| 6,071,263 A | 6/2000 | Kirkman |
| 6,117,386 A | 9/2000 | Stiger |
| 6,126,649 A | 10/2000 | VanTassel et al. |
| 6,159,158 A | 12/2000 | Lowe |
| 6,159,177 A | 12/2000 | Amos, Jr. et al. |
| 6,338,735 B1 | 1/2002 | Stevens |
| 6,383,206 B1 | 5/2002 | Gillick et al. |
| 6,447,530 B1 | 9/2002 | Ostrovsky et al. |
| 6,450,988 B1 | 9/2002 | Bradshaw |
| 6,485,500 B1 | 11/2002 | Kokish et al. |
| 6,491,662 B1 | 12/2002 | Liprie et al. |
| 6,500,167 B1 | 12/2002 | Webster, Jr. |
| 6,500,182 B1 | 12/2002 | Foster |
| 6,508,833 B2 | 1/2003 | Pavcnik et al. |
| 6,527,737 B2 | 3/2003 | Kaneshige |
| 6,530,913 B1 | 3/2003 | Giba et al. |
| 6,533,783 B1 | 3/2003 | Tollner |
| 6,558,349 B1 | 5/2003 | Kirkman |
| 6,572,610 B2 | 6/2003 | Kovalcheck et al. |
| 6,629,987 B1 | 10/2003 | Gambale |
| 6,673,060 B1 | 1/2004 | Fleming, III |
| 6,679,860 B2 | 1/2004 | Stiger |
| 6,692,484 B1 | 2/2004 | Karpiel et al. |
| 6,695,858 B1 | 2/2004 | Dubrul et al. |
| 6,755,812 B2 | 6/2004 | Peterson et al. |
| 6,918,929 B2 | 7/2005 | Udipi et al. |
| 6,932,829 B2 | 8/2005 | Majercak |
| 7,037,290 B2 | 5/2006 | Gardeski et al. |
| 7,144,408 B2 | 12/2006 | Keegan et al. |
| 7,232,462 B2 | 6/2007 | Schaeffer |
| 7,269,453 B2 | 9/2007 | Mogul |
| 7,503,914 B2 | 3/2009 | Coleman et al. |
| 7,520,876 B2 | 4/2009 | Ressemann et al. |
| 7,641,630 B2 | 1/2010 | Accisano, III et al. |
| 7,658,305 B2 | 2/2010 | Voegele et al. |
| 7,678,099 B2 | 3/2010 | Ressemann et al. |
| 7,736,331 B2 | 6/2010 | Accisano, III et al. |
| 7,740,608 B2 | 6/2010 | Lampropoulos et al. |
| 7,785,252 B2 | 8/2010 | Danitz et al. |
| 7,785,315 B1 | 8/2010 | Muni et al. |
| 7,803,130 B2 | 9/2010 | Ryan et al. |
| 7,811,277 B2 | 10/2010 | Boulais |
| 7,867,218 B1 | 1/2011 | Voda |
| 7,892,233 B2 | 2/2011 | Hall et al. |
| 7,909,814 B2 | 3/2011 | Accisano, III et al. |
| 7,909,862 B2 | 3/2011 | Garrison |
| 7,935,108 B2 | 5/2011 | Baxter et al. |
| 7,959,601 B2 | 6/2011 | McDaniel et al. |
| 7,959,644 B2 | 6/2011 | Shriver |
| 8,029,461 B2 | 10/2011 | Thielen et al. |
| 8,066,664 B2 | 11/2011 | LaDuca et al. |
| 8,070,693 B2 | 12/2011 | Ayala et al. |
| 8,083,879 B2 | 12/2011 | Swinehart et al. |
| 8,118,803 B1 | 2/2012 | Chow |
| 8,182,467 B2 | 5/2012 | Nguyen et al. |
| 8,216,210 B2 | 7/2012 | Ostrovsky et al. |
| 8,369,923 B2 | 2/2013 | de la Rama et al. |
| 8,403,977 B2 | 3/2013 | Case |
| 8,425,466 B2 | 4/2013 | Sargent, Jr. |
| 8,430,864 B2 | 4/2013 | Schultz |
| 8,496,645 B2 | 7/2013 | Eells et al. |
| 8,535,310 B2 | 9/2013 | Hardin, Jr. et al. |
| 8,535,349 B2 | 9/2013 | Chen et al. |
| 8,579,802 B2 | 11/2013 | Robertson |
| 8,603,185 B2 | 12/2013 | Shah et al. |
| 8,657,805 B2 | 2/2014 | Peh et al. |
| 8,734,426 B2 | 5/2014 | Ahmed et al. |
| 8,758,231 B2 | 6/2014 | Bunch et al. |
| 2001/0039450 A1 | 11/2001 | Pavcnik et al. |
| 2002/0115983 A1 | 8/2002 | Sekino et al. |
| 2003/0004460 A1 | 1/2003 | Bedell |
| 2003/0032977 A1 | 2/2003 | Brady |
| 2003/0050694 A1 | 3/2003 | Heneveld et al. |
| 2004/0087965 A1 | 5/2004 | Hebert et al. |
| 2004/0087996 A1 | 5/2004 | Forcucci et al. |
| 2004/0225322 A1 | 11/2004 | Garrison et al. |
| 2005/0171592 A1 | 8/2005 | Majercak |
| 2005/0256452 A1 | 11/2005 | DeMarchi et al. |
| 2006/0063973 A1 | 3/2006 | Makower et al. |
| 2007/0093781 A1 | 4/2007 | Kugler et al. |
| 2007/0167682 A1 | 7/2007 | Goldfarb et al. |

(56) References Cited

U.S. PATENT DOCUMENTS

| | | |
|---|---|---|
| 2007/0219464 A1 | 9/2007 | Davis et al. |
| 2007/0250105 A1 | 10/2007 | Ressemann et al. |
| 2007/0293727 A1 | 12/2007 | Goldfarb et al. |
| 2008/0039692 A1* | 2/2008 | Hirakawa ........... A61B 1/00045 600/160 |
| 2008/0097154 A1 | 4/2008 | Makower et al. |
| 2008/0125756 A1 | 5/2008 | Dicarlo et al. |
| 2008/0243067 A1 | 10/2008 | Rottenberg et al. |
| 2008/0249483 A1 | 10/2008 | Slenker et al. |
| 2008/0281156 A1 | 11/2008 | Makower et al. |
| 2008/0287918 A1 | 11/2008 | Rosenman et al. |
| 2009/0030274 A1 | 1/2009 | Goldfarb et al. |
| 2009/0043299 A1 | 2/2009 | Racz |
| 2009/0044799 A1* | 2/2009 | Qiu ...................... A61B 5/0084 128/200.26 |
| 2009/0093823 A1 | 4/2009 | Chang et al. |
| 2009/0198153 A1 | 8/2009 | Shriver |
| 2009/0326450 A1 | 12/2009 | Ostrovsky et al. |
| 2010/0010309 A1 | 1/2010 | Kitagawa |
| 2010/0030113 A1 | 2/2010 | Morriss et al. |
| 2010/0076269 A1 | 3/2010 | Makower et al. |
| 2010/0099946 A1 | 4/2010 | Jenkins et al. |
| 2010/0211007 A1 | 8/2010 | Lesch, Jr. et al. |
| 2010/0217261 A1 | 8/2010 | Watson |
| 2010/0262075 A1 | 10/2010 | Danitz et al. |
| 2010/0280316 A1 | 11/2010 | Dietz et al. |
| 2010/0331776 A1 | 12/2010 | Salahieh et al. |
| 2011/0009700 A1 | 1/2011 | Ostrovsky et al. |
| 2011/0040269 A1 | 2/2011 | Cline |
| 2011/0112476 A1 | 5/2011 | Kauphusman et al. |
| 2011/0190831 A1 | 8/2011 | Mafi et al. |
| 2011/0218492 A1 | 9/2011 | McDaniel et al. |
| 2011/0224647 A1* | 9/2011 | Lazarus ................ A61M 1/008 604/506 |
| 2011/0264134 A1 | 10/2011 | Drontle et al. |
| 2011/0313392 A1 | 12/2011 | Varghese et al. |
| 2012/0046664 A1 | 2/2012 | McGuckin, Jr. et al. |
| 2012/0101441 A1 | 4/2012 | Sargent, Jr. |
| 2012/0162401 A1 | 6/2012 | Melder et al. |
| 2012/0197240 A1 | 8/2012 | Smith et al. |
| 2012/0238952 A1 | 9/2012 | Mitchell et al. |
| 2012/0265055 A1 | 10/2012 | Melsheimer et al. |
| 2013/0041314 A1 | 2/2013 | Dillon |
| 2013/0046138 A1 | 2/2013 | McLawhorn |
| 2013/0096384 A1 | 4/2013 | Arai |
| 2013/0103004 A1 | 4/2013 | Gray et al. |
| 2013/0226146 A1 | 8/2013 | Tekulve |
| 2013/0238003 A1 | 9/2013 | Fischer et al. |
| 2014/0088355 A1 | 3/2014 | Schaeffer |

FOREIGN PATENT DOCUMENTS

| | | |
|---|---|---|
| GB | 2465621 A | 6/2010 |
| WO | WO98043530 | 10/1998 |
| WO | WO2001026726 A1 | 4/2001 |
| WO | WO200170308 | 9/2001 |
| WO | 2003001986 | 1/2003 |

OTHER PUBLICATIONS

International Searching Authority. International Search Report and Written Opinion, for International App. No. PCT/US2014/018878. Jun. 11, 2014. p. 1-12.

Non-final Office Action dated Sep. 15, 2009 U.S. Appl. No. 11/800,292.

eyeMAX CCD Laparscopes [online brochure]. Richard Wolf GmbH [retrieved Nov. 15, 2013]. Retrieved from the internet: URL: http://www.richard-wolf.com/uploads/media/A_658_Eyemax_GB_I07.pdf. pp. 1-8.

eyeMAX Flexible LED Cystoscope [online brochure]. Richard Wolf GmbH [retrieved Nov. 15, 2013]. Retrieved from the internet: URL: http://www.richardwolfusa.com/fileadmin/images/content/USA_data/PDF_documents/Urology/Flexible_LED_Digital_Cystoscope_brochure_01312013.pdf. pp. 1-4.

Olympus Naso-laryngoscopes. Olympus. Retrieved from the internet: URL: www.olympuskeymed.com, pp. 1-3.

XprESS Multi-Sinus Dilation Tool Using Bending Tool. Instructions for Use, Entellus Medical, Sep. 2011, pp. 1-7.

XprESS Multi-Sinus Dilation Tool. Instructions for Use, Entellus Medical, May 2011, pp. 1-7.

A trial study of RhinoSleep for the diagnosis of sleep apnea. Psychiatry and Clinical Neurosciences. Jun. 2001, pp. 1-2.

E.G. Scan—Trans-nasal, disposable system for upper GI screening [online brochure]. SynMed Ltd. [retrieved Jun. 4, 2014]. Retrieved from the internet: URL: http://www.synmed.co.uk/products/eg_scan/pdf/SynMed_E.G.Scan_Brochure.pdf.

Drug-induced Sleep Endoscopy webpage [online], Eric J. Kezirian [retrieved Nov. 14, 2013]. Retrieved from the internet: URL: http://www.sleep-doctor.com/surgical-treatment-overview/drug-induced-sleep-endoscopy/.

EyeMax webpage [online], Richard Wolf [retrieved Nov. 14, 2013]. Retrieved from the internet: URL: http://www.richard-wolf.com/en/human-medicine/visualisation/video-endoscopes/ccd-endoscopes.html.

Japanese Patent Office, English Translation of Office Action for Japanese Patent Application No. 2015-560297, dated Oct. 31, 2017, pp. 1-5.

\* cited by examiner

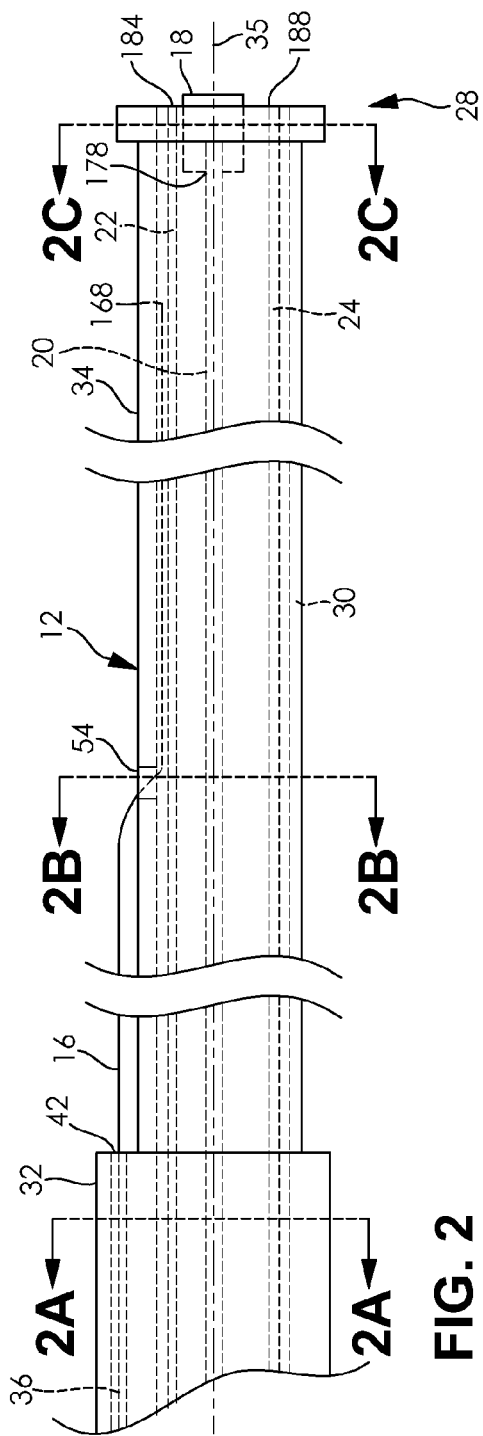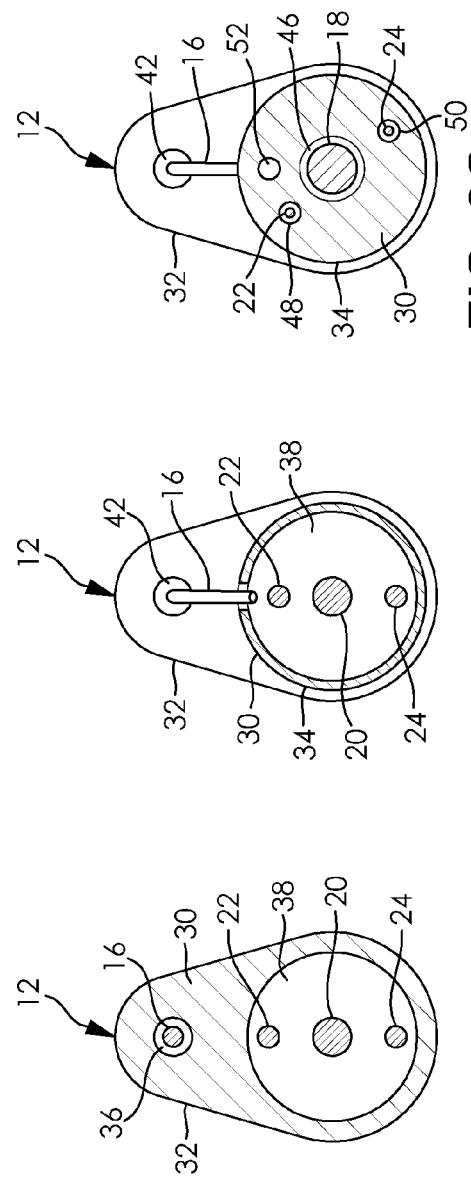

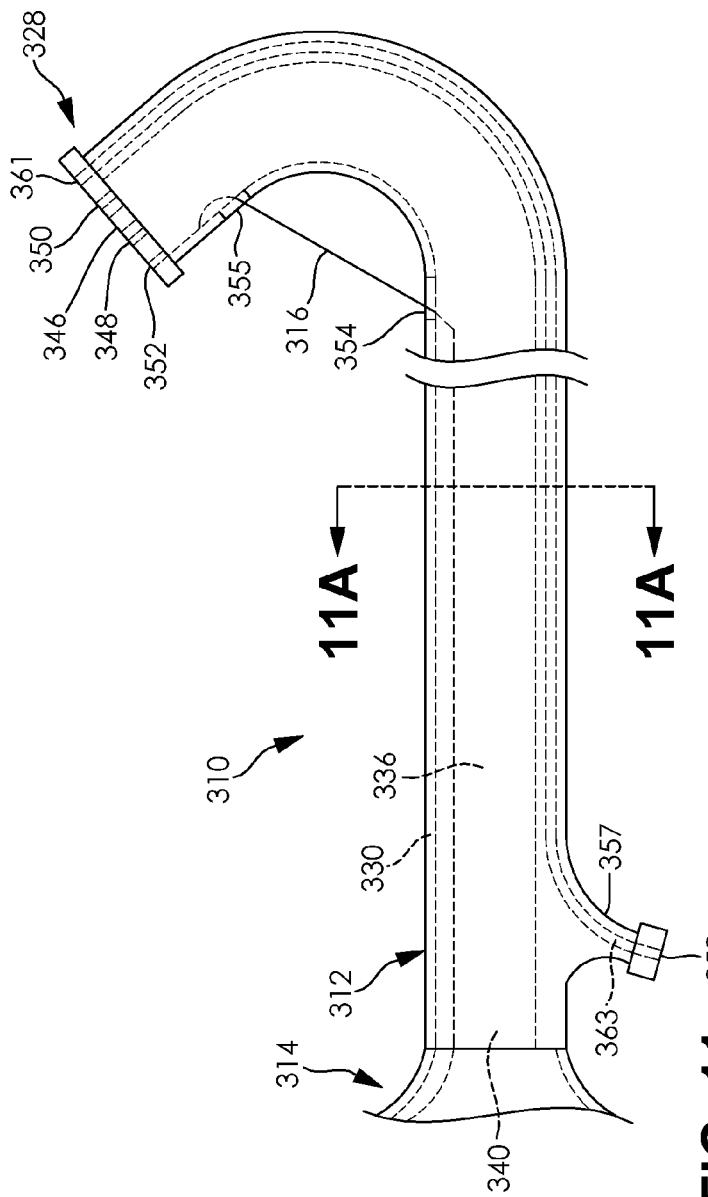
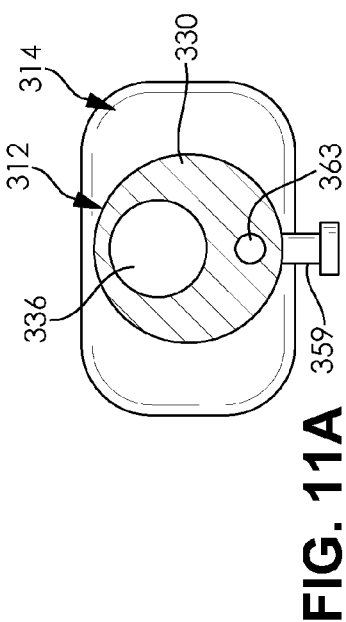
FIG. 11
FIG. 11A

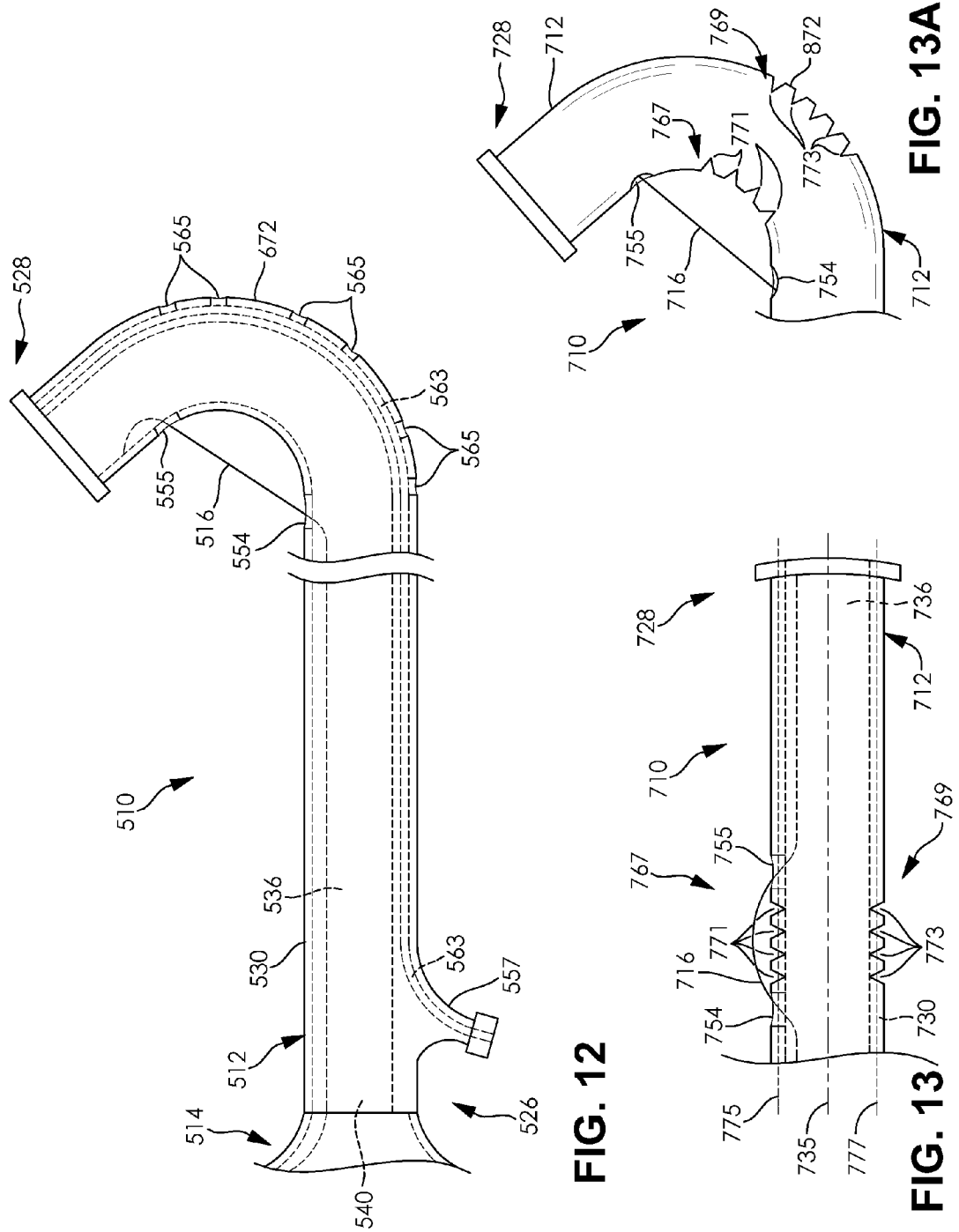

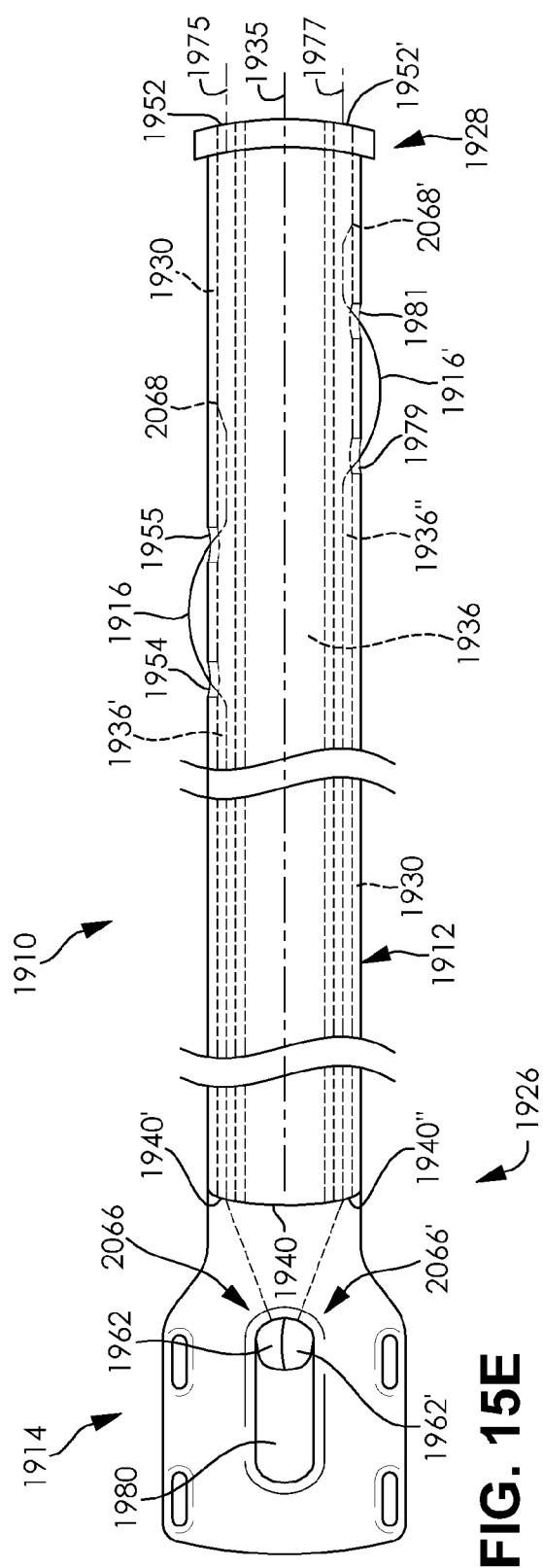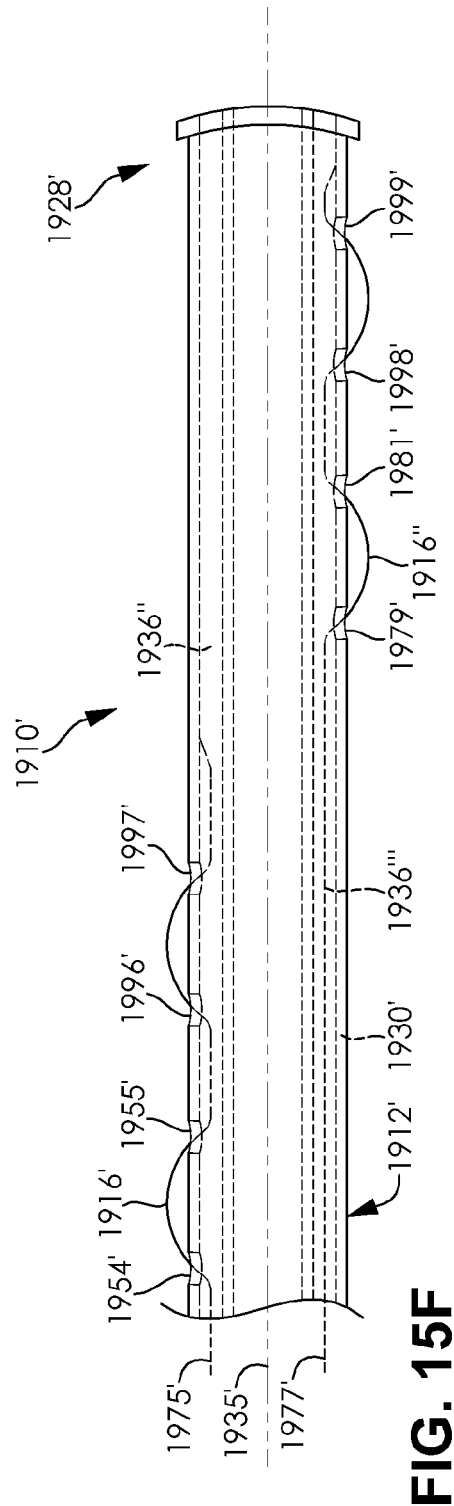

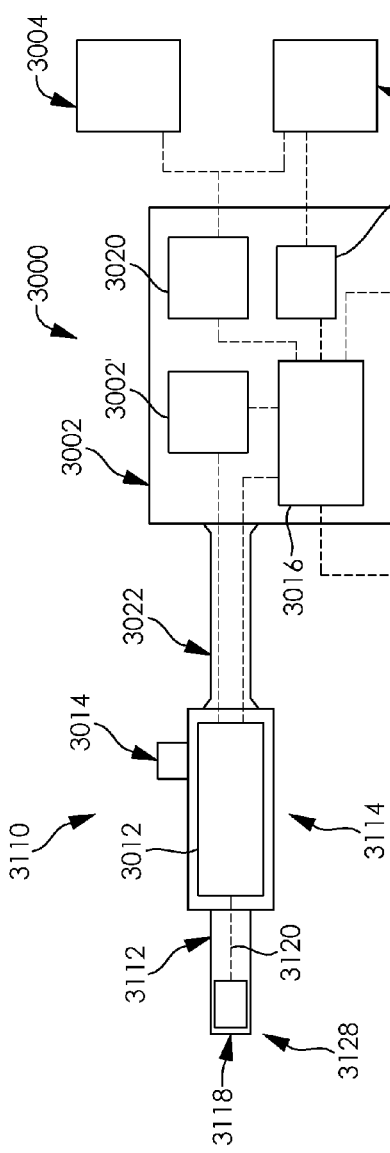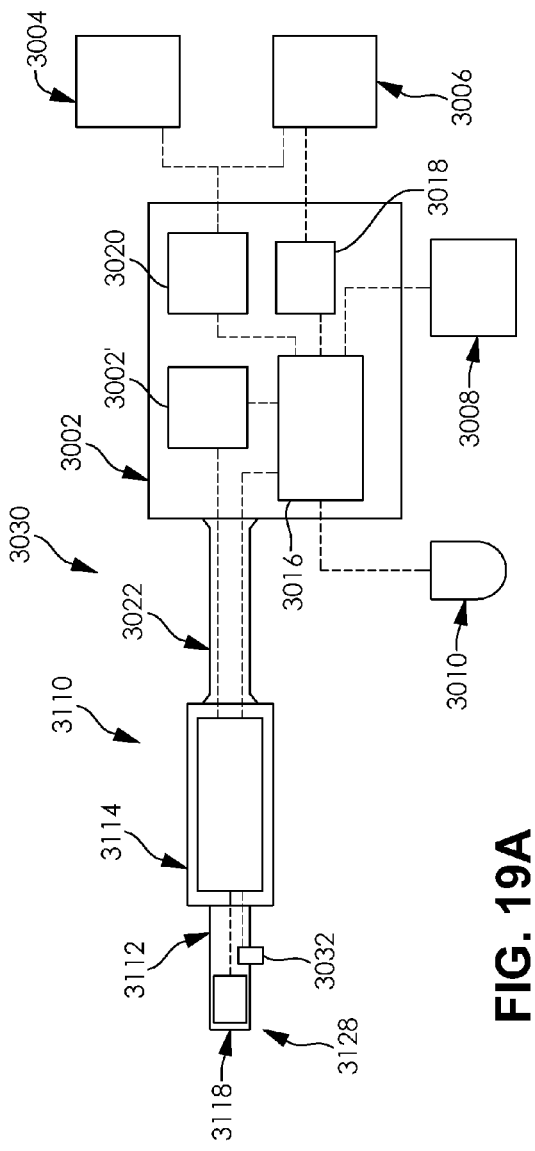
FIG. 19
FIG. 19A

MEDICAL DEVICES, SYSTEMS, AND METHODS FOR THE VISUALIZATION AND TREATMENT OF BODILY PASSAGES

RELATED APPLICATIONS

This application claims the benefit of U.S. Provisional Application No. 61/770,405, filed Feb. 28, 2013. The entire contents of this related application are hereby incorporated into this disclosure by reference.

FIELD

The disclosure relates generally to medical devices, systems, and methods. More particularly, the disclosure relates to medical devices, systems, and methods for the visualization and treatment of bodily passages, such as an airway, sinus cavity, or sinus passage.

BACKGROUND

Obstructive Sleep Apnea (OSA) Syndrome is a respiratory disorder characterized by periodic cessation of breathing caused by upper airway obstruction. Sleep causes the muscles of the upper airway to relax and the associated soft tissues to sag, resulting in narrowing or collapse of the upper airway, and consequent reduction in ventilation. Mild OSA can lead to fatigue, reduced alertness following sleep, and a general reduction in productivity for the affected individual. Severe OSA can lead to sleep deprivation, hypoxemia, and depression.

OSA can have several causes, with each requiring a different remedy. For example, in some cases OSA can be the result of obesity and/or diabetes. In other cases, OSA is caused by the anatomy of the septum, turbinates, palate, tongue, pharyngeal wall, muscle tone in upper airway, epiglottis, and/or uvula. Therefore, individual treatment of OSA requires a study of the causes of OSA in the individual to determine the appropriate form of treatment.

The conventional approach to diagnosis of sleep disorders, such as OSA, has been to require an individual to participate in a "sleep study," which is completed during natural sleep or artificially induced sleep. During a natural sleep study, the individual is outfitted with an array of sensors attached to the surface of the body and face that monitor the individual's respiration, pulse, and blood oxygen saturation, among other physiological statistics. During a drug induced sleep endoscopy (DISE), during which sleep is artificially induced using midazolam or propofol, a scope is disposed within the airway to determine the source of the obstruction.

Conventional sleep studies, however, have several shortcomings. For example, during natural sleep studies visualization of the airway is not performed, which prevents identifying potential obstructions. Artificially induced sleep studies require the use of anesthesia, which increases the risks associated with performing the study. In addition, inducing artificial sleep may alter the results of the sleep study due to the sleep-inducing drug manipulating normal bodily functions. For example, the structural configuration and function of an airway may be altered when using sleep-inducing drugs as compared to the structural configuration and function of an airway during normal sleep. Moreover, artificially induced sleep studies are typically performed with the individual laying on his or her back, which fails to provide data regarding obstructions when the individual is in other sleeping positions.

Therefore, a need exists for improved medical devices, systems, and methods for visualizing and treating bodily passages.

SUMMARY

Various exemplary medical devices are described.

An exemplary medical device comprises an elongate member, a handle, and a wire member. The elongate member has an elongate member proximal end, elongate member distal end, and elongate member body. The elongate member body defines a first elongate member lumen, second elongate member lumen, first elongate member proximal opening, second elongate member proximal opening, first elongate member distal opening, elongate member first aperture, elongate member second aperture, and an elongate member third aperture. The first elongate member distal opening is disposed between the elongate member proximal end and the elongate member distal end. The elongate member first aperture is disposed between the first elongate member distal opening and the elongate member distal end. The elongate member second aperture is disposed between the elongate member first aperture and the elongate member distal end. The elongate member third aperture is disposed between the elongate member second aperture and the elongate member distal end. The first elongate member lumen extends from the first elongate member proximal opening to the first elongate member distal opening. The second elongate member lumen extends from the second elongate member opening to the elongate member distal end. Each of the elongate member first aperture, elongate member second aperture, and elongate member third aperture extends through the elongate member body and provides access to the second elongate member lumen. The handle is attached to the elongate member and has an actuator moveable between an actuator first position and an actuator second position. The wire member has a wire member first end attached to the actuator and a wire member second end attached to the elongate member. The wire member extends from the wire member first end through the first elongate member lumen to the elongate member first aperture. The wire member extends through the elongate member first aperture and into the second elongate member lumen and to the elongate member second aperture. The wire member extends through the elongate member second aperture along the elongate member to the elongate member third aperture. The wire member extends through the elongate member third aperture and into the second elongate member lumen. The elongate member is moveable between a substantially straight configuration when the actuator is in the actuator first position and a curved configuration when the actuator is in the actuator second position.

Another exemplary medical device comprises an elongate member, a handle, and a wire member. The elongate member has an elongate member proximal end, elongate member distal end, and elongate member body. The elongate member body defines a first elongate member lumen, second elongate member lumen, first elongate member proximal opening, second elongate member proximal opening, first elongate member distal opening, elongate member first aperture, elongate member second aperture, and an elongate member third aperture. The first elongate member distal opening is disposed between the elongate member proximal end and the elongate member distal end. The elongate member first aperture is disposed between the first elongate member distal opening and the elongate member distal end. The elongate member second aperture is disposed between the elongate member first aperture and the elongate member distal end. The elongate member third aperture is disposed between the elongate member second aperture and the elongate member distal end. The first elongate member lumen extends from the first elongate member proximal opening to the first elongate member distal opening. The second elongate member lumen extends from the second elongate member opening to the elongate member distal end. Each of the elongate member first aperture, elongate member second aperture, and elongate member third aperture extends through the elongate member body and provides access to the second elongate member lumen. The handle is attached to the elongate member and has an actuator moveable between an actuator first position and an actuator second position. The wire member has a wire member first end attached to the actuator and a wire member second end attached to the elongate member. The wire member extends from the wire member first end through the first elongate member lumen to the elongate member first aperture. The wire member extends through the elongate member first aperture and into the second elongate member lumen and to the elongate member second aperture. The wire member extends through the elongate member second aperture along the elongate member to the elongate member third aperture. The wire member extends through the elongate member third aperture and into the second elongate member lumen. The elongate member is moveable between a substantially straight configuration when the actuator is in the actuator first position and a curved configuration when the actuator is in the actuator second position. The elongate member defines a first curve and a second curve when the actuator is in the actuator second position. The first curve has a first radius of curvature and the second curve has a second radius of curvature.

Furthermore, various methods of treatment are described.

An exemplary method of visualizing an airway comprises the steps of: introducing a medical device having a medical device proximal end and medical device distal end into said airway such that the medical device distal end is disposed within said airway; advancing the actuator from the actuator first position to the actuator second position to define a curve along the elongate member length; obtaining one or more images from the imaging device; advancing the actuator from the actuator second position to the actuator first position; and removing the medical device from the airway.

Additional understanding of the exemplary medical devices, systems, and methods can be obtained by review of the detailed description, below, and the appended drawings.

BRIEF DESCRIPTION OF THE FIGURES

FIG. 2 is a partial side view of the medical device illustrated in FIG. 1.

FIG. 2A is a sectional view of the medical device illustrated in FIG. 2, taken along line 2A-2A.

FIG. 2B is a sectional view of the medical device illustrated in FIG. 2, taken along line 2B-2B.

FIG. 2C is a sectional view of the medical device illustrated in FIG. 2, taken along line 2C-2C.

In FIG. 10 the housing second portion has been removed.

FIG. 11 is a partial side view of another exemplary medical device in a second configuration.

FIG. 11A is a sectional view of the medical device illustrated in FIG. 11, taken along line 11A-11A.

FIG. 12 is a partial side view of another exemplary medical device in a second configuration.

FIG. 13 is a partial side view of another exemplary medical device in a first configuration.

FIG. 13A is a partial side view of the medical device illustrated in FIG. 13 in a second configuration.

FIG. 15E is a side view of another exemplary medical device in a first configuration.

FIG. 15F is a partial side view of another exemplary medical device in a first configuration.

FIG. 19 is a schematic representation of an exemplary imaging system.

FIG. 19A is a schematic representation of another exemplary imaging system.

DETAILED DESCRIPTION

Figure 1:
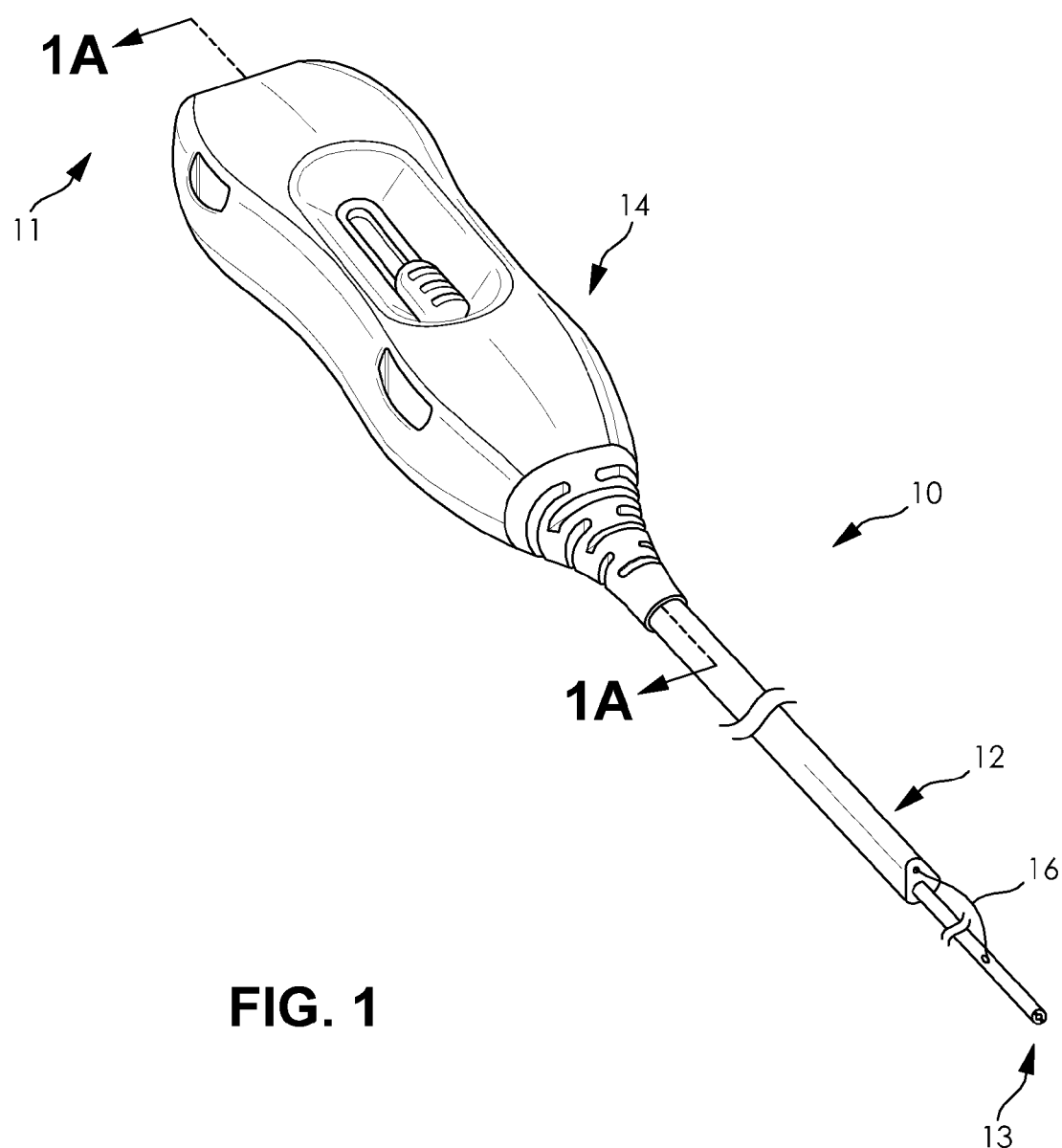
FIG. 1 is a perspective view of an exemplary medical device in a first configuration.

The following detailed description and the appended drawings describe and illustrate various exemplary medical devices, systems, and methods. The description and drawings are exemplary in nature and are provided to enable one skilled in the art to make and use one or more exemplary medical devices, systems, and/or practice one or more exemplary methods. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "exemplary" refers to "an example of" and is not intended to convey a meaning of an ideal or preferred embodiment. The use of "attached" refers to the fixed, releasable, or integrated association of two or more elements and/or devices. Thus, the term "attached" includes releasably attaching or fixedly attaching two or more elements and/or devices. The use of "diameter" refers to the length of a straight line passing from side to side through the center of a body or feature and does not impart any structural configuration on the body or feature. As used herein, the terms "proximal" and "distal" are used to describe opposing axial ends of the particular elements or features being described. The use of "bodily passage" or "body passage" refers to any passage within the body of an animal, including, but not limited to, humans, and includes elongate passages. The term "sinus passage" refers to the nasal passages, and includes, but is not limited to, eustachian tube(s), primary ostium, accessory ostium, and/or an opening defined by a ventilation tube. The term "airway" refers to any airway including, but not limited to, the nasal cavity, nasopharynx, oropharynx, pharynx, trachea, bronchial tubes, esophagus, and/or lungs. The term "sinus cavity" refers to the frontal, ethmoid, sphenoid, and/or maxillary sinus. The term "medication" refers to any fluid, drug, agent, therapeutic agent, and/or any other material used to treat a patient.

FIGS. 1, 2, 2A, 2B, 2C, 3, 4, and 5 illustrate an exemplary medical device 10 having a medical device proximal end 11 and a medical device distal end 13 and comprising an elongate member 12, handle 14, wire member 16, imaging device 18, data transfer cable 20, first optical fiber 22, and second optical fiber 24.

Elongate member 12 can have any suitable outside diameter and any suitable length, and skilled artisans will be able to select a suitable outside diameter and length for an elongate member according to a particular embodiment based on various considerations, including the desired bodily passage within which a medical device is intended to be used. The inventors have determined that elongate members having an outside diameter between about 1 mm to about 15 mm are suitable. The inventors have also determined that elongate members having an outside diameter between about 1 mm to about 10 mm are suitable. The inventors have also determined that elongate members having an outside diameter less than 5 mm are suitable. The inventors have also determined that elongate members having an outside diameter less than 4 mm are suitable. In embodiments in which an elongate member includes a portion that comprises an oval, or substantially oval, cross section, the inventors have determined that elongate members having a width between about 1 mm to about 3 mm are suitable and heights between about 3 mm and about 10 mm are suitable. The inventors have determined that elongate members having a length between about 0.3048 meters to about 4.572 meters are suitable. The inventors have also determined that elongate members having a length between about 1.524 meters to about 3.048 meters are suitable. The inventors have also determined that elongate members having a length between about 1.524 meters to about 2.4384 meters are suitable. The inventors have also determined that elongate members having a length about 0.70 meters are suitable. For example, in embodiments in which it is desired to attach a handle of a medical device to the arm of the individual on which a procedure is being performed, the inventors have determined that elongate members having a length about 0.70 meters are suitable. In embodiments in which it is desired to attach a handle of a medical device to the bed on which the individual is positioned, the inventors have determined that elongate members having a length between about 1.524 meters to about 2.4384 meters are suitable.

Elongate member 12 can be formed of any suitable material and can be fabricated using any suitable method of manufacture. Skilled artisans will be able to select a suitable material to form an elongate member and a suitable method of manufacture according to a particular embodiment based on various considerations, including the desired flexibility of the elongate member. Example materials considered suitable to form an elongate member include, but are not limited to, biocompatible materials, materials that can be made biocompatible, metals such as stainless steel, titanium, nickel-titanium alloy (e.g., Nitinol), polymers, Pebax (Pebax is a registered trademark of AtoChimie Corporation of Allee des Vosges, Courbevoie, France), nylon, polyethylene, polyurethane, silicone, coiled materials, braided materials, and any other material considered suitable for a particular application. Example methods of manufacture considered suitable to fabricate an elongate member include, but are not limited to, extrusion processes, molding processes, and any other method considered suitable for a particular application.

For example, an elongate member, or a portion of an elongate member, can be formed of a braided material to add torsional strength to the elongate member or of a coiled material to impart kink-resistance along the length of elongate member that includes coiled material. Optionally, an elongate member, or a portion of an elongate member, can be formed of both a braided material and coiled material, to impart torsional strength and kink-resistance along the length of elongate member that includes braided and coiled material.

Optionally, an elongate member, or a portion of an elongate member, can be formed of a malleable material such that a user can bend and/or shape the elongate member before or during a procedure to conform with the actual or expected anatomy of a bodily passage, such as a sinus passage, airway, sinus cavity, or any other suitable bodily passage. Alternatively, a malleable elongate member can be disposed within an elongate member body, or a lumen defined by an elongate member body, such that a user can bend and/or shape the elongate member before or during a procedure to conform with the actual or expected anatomy of a bodily passage, such as a sinus passage, airway, sinus cavity, or any other suitable bodily passage.

Figure 5:
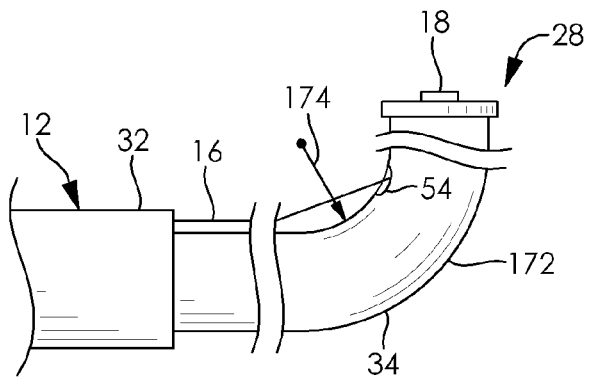
FIG. 5 is a partial side view of the medical device illustrated in FIG. 1 in a second configuration.

In the illustrated embodiment, elongate member 12 comprises an elongate member proximal end 26, elongate member distal end 28, elongate member body 30, elongate member first portion 32 (e.g., first portion of the axial length of the elongate member 12), elongate member second portion 34 (e.g., second portion of the axial length of the elongate member 12), and an elongate member lengthwise axis 35 that extends through the length of elongate member 12. Elongate member body 30 defines a first elongate member lumen 36, second elongate member lumen 38, first elongate member proximal opening 40, first elongate member distal opening 42, second elongate member proximal opening 44, imaging device opening 46, first optical fiber opening 48, second optical fiber opening 50, wire member opening 52, and elongate member first aperture 54. Elongate member 12 has a first straight, or substantially straight, configuration, as shown in FIG. 1, and a second curved configuration, as shown in FIG. 5.

As an alternative to elongate member body 30 defining imaging device opening 46, first optical fiber opening 48, second optical fiber opening 50, and wire member opening 52, a separate cap can be disposed on the distal end of the elongate member and can comprise part of the elongate member. In these embodiments, the cap can have a cap body that defines an imaging device opening, a first optical fiber opening, a second optical fiber opening, a wire member opening, or any other opening described herein as defined by an elongate member body. The cap can be adapted to be attached to the distal end of the elongate member using any suitable composition, structure, or technique for attaching components to each other, including permanent and temporary attachments. For example, the components can define threads, or an adhesive can be applied to one or both components. The components could be welded or fused together. Also, a separate attachment member, such as a clip, could be used to attach the components to each other. Any of the devices described herein (e.g., optical fiber, imaging device, wire member) can be attached to the cap, as described with respect to attachment of a device to an elongate member.

FIGS. 22, 23, 24, and 25 illustrate an exemplary cap 10" that can be attached to the distal end of an elongate member, such as those described herein (e.g., elongate member 12). The cap 10" has a lengthwise axis 11", a proximal end 12", a distal end 14", and a body 16". The body 16" defines a shaft 18", a flange 20", a passageway 22", a wire member opening 24", a first optical fiber opening 26", a second optical fiber opening 28", an irrigation opening 30", a first shaft opening 32", and a second shaft opening 34".

The shaft 18" extends from the proximal end 12" of the cap 10" to the flange 20" and has a length 19". The proximal end 12" of the shaft 18" defines two protrusions that are sized and configured to assist with attachment of an imaging device to cap 10". The flange 20" extends from the shaft 18" and away from the lengthwise axis 11" of the cap 10" and has a length 23". The length 23" of the flange 20" is less than the length 19" of the shaft 18". The shaft 18" has a first outside diameter 25" and the flange 20" has a second outside diameter 27". The second outside diameter 27" is greater than the first outside diameter 25". This provides a mechanism for passing an elongate member that includes a cap 10" through the anatomy of a bodily passage, sinus passage, airway, and/or sinus cavity, which may have a non-circular cross-sectional configuration. The passageway 22" extends through the shaft 18" and the flange 20" from the proximal end 12" of the cap 10" to the distal end 14" of the cap 10" and is sized and configured to receive a portion of an imaging device (e.g., imaging device 18) and/or a data transfer cable (e.g., data transfer cable 20). Each of the wire member opening 24", first optical fiber opening 26", second optical fiber opening 28", and irrigation opening 30" extends through the length 23" of the flange 20". The wire member opening 24" is sized and configured to receive a portion of a wire member (e.g., wire member 16) such that the wire member can be attached within the wire member opening 24". Each of the first optical fiber opening 26" and second optical fiber opening 28" is sized and configured to receive a portion of an optical fiber (e.g., first optical fiber 22, second optical fiber 24) such that the optical fiber can be attached within the first optical fiber opening 24" or the second optical fiber opening 26". The irrigation opening 30" is sized and configured to receive a portion of an irrigation tube. For example, any of the medical devices described herein can include an irrigation tube that has a proximal end, a distal end, and a body that defines a proximal end opening and a distal end opening in communication with a passageway. The handle included on any of the medical devices described herein can define a flush port and/or opening such that the irrigation tube can be attached to the handle. The proximal end of the irrigation tube can be attached to the flush port, or be disposed within the opening, defined by the handle and the distal end of the irrigation tube can be attached within the irrigation opening 30". Optionally, the distal end of the irrigation tube can include a nozzle to direct the flow of fluid toward the imaging device. Optionally, the distal end of the irrigation tube can be attached to the cap 10" such that the distal end opening is directed toward an imaging device included on the medical device (e.g., toward the lengthwise axis of the elongate member, through an 90 degree, or substantially 90 degree bend in the irrigation tube).

Each of the first shaft opening 32" and second shaft opening 34" is defined between the proximal end 12" of the cap 10" and the flange 20" and provides access to the passageway 22". Each of the first shaft opening 32" and second shaft opening 34" is sized and configured to allow adhesive to be passed through a respective shaft opening to assist with attachment of an imaging device and/or lenses to the cap 10". Alternatively, other methods of attachment are considered suitable, such as those described herein. Optionally, each of the first shaft opening and second shaft opening can be sized and configured to receive one or more of a wire member (e.g., wire member 16), optical fiber (e.g., first optical fiber 22, second optical fiber 24), and/or an irrigation tube, such as the irrigation tube described above. For example, a wire member, optical fiber, and/or irrigation tube can extend through a lumen defined by an elongate member (e.g., second elongate member lumen 38) and be passed through the first shaft opening 32" or the second shaft opening 34" and extend to an opening defined by the flange 20" (e.g., wire member opening 24", first optical fiber opening 26", second optical fiber opening 28", irrigation opening 30"). Alternatively, a wire member, optical fiber, and/or irrigation tube can extend through a lumen defined by an elongate member (e.g., second elongate member lumen 38) and be positioned between the exterior surface of the shaft and the interior surface of the elongate member and extend to an opening defined by the flange 20" (e.g., wire member opening 24", first optical fiber opening 26", second optical fiber opening 28", irrigation opening 30").

In the embodiment shown, the first outside diameter 25" of the shaft 18" is sized and configured to be received by a lumen defined by an elongate member (e.g., second elongate member lumen 38). For example, the shaft 18" can be entirely disposed within a lumen defined by an elongate member (e.g., second elongate member lumen 38) such that the flange 20" is adjacent the elongate member distal end (e.g., elongate member distal end 28). Alternatively, the shaft 18" can be partially disposed within a lumen defined by an elongate member (e.g., second elongate member lumen 38). The cap 10" can be attached to an elongate member using any suitable method of attachment, such as those described herein (e.g., adhesive), or any other method of attachment considered suitable for a particular embodiment.

While cap 10" has been illustrated as having a particular structural configuration, a cap can have any suitable structural configuration, and skilled artisans will be able to select a suitable structural configuration for a cap according to a particular embodiment based on various considerations, including the structural configuration of the lumen in which a portion of the cap is intended to be disposed. Example structural configurations considered suitable include caps that define a passageway (e.g., passageway 22") that has an inside diameter between about 1.790 millimeters and about 1.830 millimeters, caps that define a passageway (e.g., passageway 22") that has an inside diameter equal to, substantially equal to, or about 1.810 millimeters, caps that define a wire member opening (e.g., wire member opening 24") equal to, substantially equal to, or about 0.356 millimeters, caps that define an optical fiber opening (e.g., first optical fiber opening 26", second optical fiber opening 28") and/or a irrigation opening (e.g., irrigation opening 30") equal to, substantially equal to, or about 0.55 millimeters, caps that have a length from the proximal end of the cap to the distal end of the cap equal to, substantially equal to, or about 6.2 millimeters, caps that define a shaft opening (e.g., first shaft opening 32", second shaft opening 34") equal to, substantially equal to, or about 0.80 millimeters, and any other configuration considered suitable for a particular embodiment.

Elongate member first portion 32 extends from elongate member proximal end 26 to a location between elongate member proximal end 26 and elongate member distal end 28. In the illustrated embodiment, elongate member first portion 32 has an oval, or substantially oval, cross section. This structural arrangement provides a mechanism for passing elongate member 12 through tortuous bodily passages (e.g., turbinates).

Elongate member second portion 34 extends from a location between elongate member proximal end 26 and elongate member distal end 28 (e.g., from distal end of elongate member first portion 32) to elongate member distal end 28. In the illustrated embodiment, elongate member second portion 34 has a circular, or substantially circular, cross section. In the embodiment illustrated, the material that forms elongate member second portion 34 has a durometer hardness that is less than the durometer hardness of the material that forms elongate member first portion 32. Thus, the durometer hardness at elongate member first portion 32 has a first quantity and the durometer hardness at the elongate member second portion 34 has a second quantity that is different than the first quantity, or less than the first quantity. This configuration allows for the elongate member 12 to move between the straight, or substantially straight, configuration and the curved configuration with the application of less force on wire member, as described in more detail herein, relative to a medical device that does not include varying durometer harnesses along its length. However, an elongate member can have a constant, or substantially constant, durometer hardness along its length.

While elongate member first portion 32 has been illustrated as having an oval, or substantially oval, cross section and elongate member second portion 34 has been illustrated as having a circular, or substantially circular, cross section an elongate member can have any suitable structural arrangement along its length. Skilled artisans will be able to select a suitable structural arrangement for an elongate member according to a particular embodiment based on various considerations, including the desired procedure intended to be performed. Example structural arrangements considered suitable include, but are not limited to, an elongate member having a cross section that is continuous along its length, an elongate member having a first cross-sectional configuration and a second, different, cross-sectional configuration, an elongate member having a first cross-sectional configuration, a second, different, cross-sectional configuration, and a third cross-sectional configuration that is the same, or different than, the first-cross sectional configuration, and any other arrangements considered suitable for a particular application. Example number of cross section arrangements considered suitable to include on an elongate member include, but are not limited to, one, at least one, two, a plurality, three, four, five, six, and any other number considered suitable for a particular application. Example structural arrangement considered suitable include, but are not limited to, any suitable geometric cross-sectional arrangement, such as circular, substantially circular, oval, substantially oval, triangular, substantially triangular, square, substantially square, rectangular, substantially rectangular, and any other arrangement considered suitable for a particular application.

First elongate member lumen 36 extends from first elongate member proximal opening 40 to first elongate member distal opening 42 and is adapted to receive wire member 16. Second elongate member lumen 38 extends from second elongate member proximal opening 44 to imaging device opening 46, first optical fiber opening 48, second optical fiber opening 50, and wire member opening 52. Second elongate member lumen 38 is adapted to receive imaging device 18, data transfer cable 20, first optical fiber 22, and second optical fiber 24. Elongate member first aperture 54 is disposed between elongate member proximal end 26 and elongate member distal end 28, extends through elongate member body 30, provides access to second elongate member lumen 38, and is adapted to receive a portion of wire member 16. In the illustrated embodiment, elongate member first aperture 54 is disposed between the distal end of elongate member first portion 32 and elongate member distal end 28.

In the illustrated embodiment, each of first elongate member distal opening 42 and elongate member first aperture 54 is disposed on a plane that extends from elongate member lengthwise axis 35. Thus, first elongate member distal opening 42 and elongate member first aperture 54 are spaced longitudinally along the length of elongate member 12 and are disposed linearly along elongate member 12.

Each of first elongate member proximal opening 40, first elongate member distal opening 42, second elongate member proximal opening 44, imaging device opening 46, first optical fiber opening 48, second optical fiber opening 50, wire member opening 52, and elongate member first aperture 54 can have any suitable structural configuration. Skilled artisans will be able to select a suitable structural configuration for an elongate member opening and/or aperture defined by an elongate member body according to a particular embodiment based on various considerations, including the material forming an elongate member. Example structural configurations considered suitable for an elongate member opening and/or aperture defined by an elongate member body include, but are not limited to, defining a continuous diameter, a variable diameter, a tapered diameter, and any other structural configuration considered suitable for a particular application.

While first elongate member distal opening 42 and elongate member first aperture 54 are illustrated as disposed linearly along elongate member 12 and on a plane that extends from elongate member lengthwise axis 35, any suitable number of openings and/or apertures can be defined by an elongate member body and can be positioned at any suitable location relative to one another on an elongate member. Skilled artisans will be able to select a suitable number of openings and/or apertures to define on an elongate member and/or a suitable position to locate an elongate member opening relative to an elongate member aperture according to a particular embodiment based on various considerations, including the structural arrangement of the bodily passage within which a medical device is intended to be used. Example number of openings and/or apertures considered suitable to define on an elongate member include, but are not limited to, one, at least one, two, a plurality, three, four, five, six, and any other number considered suitable for a particular application. Example locations considered suitable to position an elongate member opening and/or elongate member aperture on an elongate member include, but are not limited to, such that the elongate member opening and elongate member aperture are contained on a plane that extends from the elongate member lengthwise axis, such that the elongate member opening is disposed on a first plane that extends from the elongate member lengthwise axis and the elongate member aperture is disposed on a second plane that extends from the elongate member lengthwise axis, the first plane is different than the second plane and is disposed at an angle to the second plane. Example angles considered suitable between a first plane containing an elongate member opening and a second plane containing an elongate member aperture include, but are not limited to, a 45 degree angle, an angle between about 1 degree to about 90 degrees, an angle about 90 degrees, an angle between about 90 degrees to about 180 degrees, an angle between about 180 degrees to about 270 degrees, an angle between about 270 degrees to about 360 degrees, and any other angle considered suitable for a particular application. Thus, an elongate member opening and elongate member aperture can be disposed linearly or offset from one another about the circumference of the elongate member.

Embodiments that include more than one elongate member aperture can also have any suitable arrangement. Example locations considered suitable to position an elongate member first aperture relative to an elongate member second aperture on an elongate member include, but are not limited to, such that the elongate member first aperture and elongate member second aperture are contained on a plane that extends from the elongate member lengthwise axis, such that the elongate member first aperture is disposed on a first plane that extends from the elongate member lengthwise axis and the elongate member second aperture is disposed on a second plane that extends from the elongate member lengthwise axis. The first plane is different than the second plane and is disposed at an angle to the second plane. Example angles considered suitable between a first plane containing an elongate member first aperture and a second plane containing an elongate member second aperture include, but are not limited to, a 45 degree angle, an angle between about 1 degree to about 90 degrees, an angle about 90 degrees, an angle between about 90 degrees to about 180 degrees, an angle between about 180 degrees to about 270 degrees, an angle between about 270 degrees to about 360 degrees, and any other angle considered suitable for a particular application. Thus, an elongate member first aperture and elongate member second aperture can be disposed linearly or offset from one another about the circumference of the elongate member.

While elongate member body 30 is illustrated as defining a first elongate member lumen 36 and a second elongate member lumen 38, an elongate member can define any suitable number of lumens, and skilled artisans will be able to select a suitable number of lumens for an elongate member body to define according to a particular embodiment based on various considerations, including the procedure intended to be performed. Example number of lumens considered suitable for an elongate member body to define include, but are not limited to, one, at least one, two, a plurality, three, four, five, six, and any other number considered suitable for a particular application. For example, alternative to wire member passing through first elongate member lumen, an elongate member can define a single lumen through which a wire member is passed.

Any portion, or the entirety, of the length of elongate member 12 or the portion of elongate member body 30 that defines first elongate member lumen 36 or second elongate member lumen 38, or any other lumen defined by an elongate member, can be lined and/or coated with any suitable material to reduce the coefficient of friction between the outer surface of the elongate member and the surface in which the outer surface is intended to, or may, contact, or the surface defining the lumen and the surface of a device being passed through the lumen. Any suitable lining and/or coating capable of reducing the coefficient of friction is considered suitable, and skilled artisans will be able to select a suitable lining and/or coating according to a particular embodiment based on various considerations, such as the bodily passage within which the medical device is intended to be used. Example lubricious coatings considered suitable to reduce the coefficient of friction include, but are not limited to, polymers such as polyethylene (PE), polytetrafluoroethylene (PTFE), and any other polymer or substance having properties that result in the lowering of the coefficient of friction between two surfaces. For example, a lining and/or coating can be included on the portion of the elongate member body 30 that defines first elongate member lumen 36 to reduce the coefficient of friction between elongate member body 30 and wire member 16 when the medical device is in use.

Handle 14 can have any suitable structural configuration, can be formed of any suitable material, and can be fabricated using any suitable method of manufacture. Skilled artisans will be able to select a suitable structural configuration, material, and a method of manufacture for a handle according to a particular embodiment based on various considerations, including the devices intended to be housed by the handle. Example materials considered suitable to form a handle include, but are not limited to, biocompatible materials, materials that can be made biocompatible, metals such as stainless steel, titanium, polymers, Pebax, nylon, polyethylene, polyurethane, silicone, and any other material considered suitable for a particular application. Example methods of manufacture considered suitable to fabricate a handle include, but are not limited to, extrusion processes, molding processes, and any other method considered suitable for a particular application.

In the illustrated embodiment, handle 14 is attached to elongate member proximal end 26 and comprises a housing first portion 56, housing second portion 58, actuator housing 60, actuator 62, and houses a control board 64.

Housing first portion 56 is adapted to be attached to housing second portion 58. In the illustrated embodiment, housing first portion 56 has a housing first portion proximal end 66, housing first portion distal end 68, housing first portion first side 70, housing first portion second side 72, and a housing first portion body 74. Housing first portion first side 70 is opposably facing, or substantially opposably facing, housing first portion second side 72. Housing first portion body 74 defines a housing first portion cavity 76, housing first portion notch 78, actuator opening 80, first toothed geometry 82, second toothed geometry 84, plurality of recesses 86, and a plurality of apertures 88.

Housing first portion cavity 76 extends into housing first portion body 74 from housing first portion second side 72 and is adapted to receive a portion of actuator housing 60, actuator 62, and/or control board 64. Housing first portion notch 78 extends into housing first portion body 74 from housing first portion second side 72 and extends from housing first portion distal end 68 to housing first portion cavity 76. Housing first portion notch 78 is adapted to receive a portion of elongate member 12. Actuator opening 80 is defined between housing first portion proximal end 66 and housing first portion distal end 68 and extends through housing first portion body 74 to provide access to housing first portion cavity 76. Each of the first toothed geometry 82 and second toothed geometry 84 extends into housing first portion cavity 76, is disposed along the length, or a portion of the length, of actuator opening 80, and is adapted to interact with a portion of actuator 62. Each recess of the plurality of recesses 86 extends into housing first portion body 74 from housing first portion second side 72 and is adapted to receive a portion of a protuberance of the plurality of protuberances 104, as described in more detail below. Each aperture of the plurality of apertures 88 extends through housing first portion body 74 and is adapted to receive a portion of an attachment member (e.g., length of hook and loop fastener material) to attach the handle to an individual or other device (e.g., bed).

In the illustrated embodiment, housing second portion 58 has a housing second portion proximal end 90, housing second portion distal end 92, housing second portion first side 94, housing second portion second side 96, and a housing second portion body 98. Housing second portion first side 94 is opposably facing, or substantially opposably facing, housing second portion second side 96. Housing second portion body 98 defines a housing second portion cavity 100, housing second portion notch 102, plurality of protuberances 104, and a plurality of apertures 106.

Housing second portion cavity 100 extends into housing second portion body 98 from housing second portion first side 94 and is adapted to receive a portion of actuator housing 60, actuator 62, and/or control board 64. Housing second portion notch 102 extends into housing second portion body 98 from housing second portion first side 94 and extends from housing second portion distal end 92 to housing second portion cavity 100. Housing second portion notch 102 is adapted to receive a portion of elongate member 12. Each protuberance of the plurality of protuberances 104 extends from the base of housing second portion cavity 100 and away from housing second portion first side 94. A portion of a protuberance of the plurality of protuberances 104 is adapted to be received by a recess of the plurality of recesses 86 to achieve attachment of housing first portion 56 to housing second portion 58. Each aperture of the plurality of apertures 106 extends through housing second portion body 98 and is adapted to receive a portion of an attachment member (e.g., length of hook and loop fastener material) to attach the handle to an individual or other device (e.g., bed).

Housing first portion cavity 76 and housing second portion cavity 100 combine to form a housing chamber 108 that is in communication with first elongate member lumen 36 and second elongate member lumen 38 and is adapted to house actuator housing 60, a portion of actuator 62, and control board 64. Thus, handle 14 defines a chamber that is in communication with the lumens defined by elongate member 12.

Optionally, housing section portion body 98 can define a housing second portion second notch that extends into housing second portion body 98 from housing second portion first side 94 and extends from housing second portion proximal end 90 to housing second portion cavity 100. Housing second portion second notch can be adapted to allow another device (e.g., communications device, HDMI cable) to pass through housing second portion second notch such that it can be attached to control board 64.

While a plurality of recesses 86 and a plurality of protuberances 104 have been illustrated and described as accomplishing attachment between housing first portion 56 and housing second portion 58, any suitable structural arrangement and/or method of attachment is considered suitable between a housing first portion and a housing second portion. Skilled artisans will be able to select a suitable structural arrangement and/or method of attachment between a housing first portion and a housing second portion according to a particular embodiment based on various considerations, including the structural arrangement of an actuator. An example structural arrangement considered suitable includes, but is not limited to, forming a housing first portion and housing second portion as an integral component. Example methods of attachment considered suitable between a housing first portion and a housing second portion include, but are not limited to, using an adhesive, welding, fusing (e.g., heat fusing), threaded fasteners, and any other method of attachment considered suitable for a particular application.

While housing first portion 56 and housing second portion 58 have been illustrated and described as having a particular structural configuration, a housing can have any suitable structural configuration, and skilled artisans will be able to select a suitable structural configuration for a housing according to a particular embodiment based on various considerations, including the structural arrangement of a control board and/or actuator.

Actuator housing 60 has an actuator housing proximal end 110, actuator housing distal end 112, actuator housing first side 114, actuator housing second side 116, and an actuator housing body 118 that defines an actuator housing recess 120, actuator housing notch 122, and a plurality of apertures 124. Actuator housing first side 114 is opposably facing, or substantially opposably facing, actuator housing second side 116. Actuator housing recess 120 extends into actuator housing body 118 from actuator housing first side 114 and is adapted to contain a portion of actuator 62. Actuator housing notch 122 extends into actuator housing body 118 from actuator housing first side 114 and extends from actuator housing distal end 112 to actuator housing recess 120. Each aperture of the plurality of apertures 124 extends through actuator housing body 118 and is adapted to receive a portion of a protuberance of the plurality of protuberances 104.

Actuator 62 comprises an actuator base 126 and an actuator control 128. Actuator base 126 comprises an actuator base proximal end 130, actuator base distal end 132, actuator base first side 134, actuator base second side 136, first base support 138, second base support 140, and an actuator base body 142 that defines a first protuberance 144, second protuberance 146, first toothed geometry 148, and second toothed geometry 150. Actuator base first side 134 is opposably facing, or substantially opposably facing, actuator base second side 136. Each of the first base support 138 and second base support 140 is biased such that it defines a curve between actuator base proximal end 130 and actuator base distal end 132. Each of the first protuberance 144 and second protuberance 146 extends from actuator base first side 134 and away from actuator base second side 136. Each of the first toothed geometry 148 and second toothed geometry 150 extends from actuator base first side 134 and away from actuator base second side 136 and is complementary to first toothed geometry 82 and second toothed geometry 84. First toothed geometry 82 and second toothed geometry 84 are adapted to interact with first toothed geometry 148 and second toothed geometry 150 to provide releasable engagement between housing first portion 56 and actuator 62.

Actuator control 128 has an actuator control first side 152, actuator control second side 154, and an actuator control body 156 that defines a first recess 158, and second recess 160. Actuator control first side 152 is opposably facing, or substantially opposably facing, actuator control second side 154. Each of the first recess 158 and second recess 160 extends into actuator control body 156 from actuator control second side 154. First recess 158 is adapted to receive a portion of first protuberance 144 and second recess 160 is adapted to receive a portion of second protuberance 146 to attach actuator control 128 to actuator base 126.

Control board 64 can comprise any suitable structure and include any suitable device, and skilled artisans will be able to select a suitable structure and device to include on a control board according to a particular embodiment based on various considerations, including the procedure intended to be performed. Example structure considered suitable includes, but is not limited to, stripboards, printed circuit boards, and any other structure considered suitable for a particular application. Example devices considered suitable to include on a control board include, but are not limited to, energy storage devices, light sources, power sources, storage devices (e.g., computer-readable medium), data transfer devices, communication devices, high-definition multimedia compliant (HDMI) compliant devices, HDMI ports, MHL ports, energy transfer devices, and any other device considered suitable for a particular application. For example, a control board can include computer readable media such that data obtained during the performance of a procedure can be transferred to another device during, or subsequent to, the performance of the procedure. A control board can be adapted to be attached to a power source or another device (e.g., computer, network) using a data transfer cable (e.g., HDMI cable, MHL cable), or communications cable, such that data obtained during the performance of a procedure can be transferred to another device during, or subsequent to, the performance of the procedure.

In the illustrated embodiment, control board 64 has a control board body 162 that defines a plurality of apertures 164. Each aperture of the plurality of apertures 164 extends through control board body 162 and is adapted to receive a portion of a protuberance of the plurality of protuberances 104. In the illustrated embodiment, control board 64 is in signal communication with imaging device 18, first optical fiber 22, and second optical fiber 24, as described in more detail herein.

Optionally, one or more data transfer devices can be operatively attached to control board 64 to transmit data to one or more devices. Skilled artisans will be able to select a suitable data transfer device to operatively attach to a control board to transfer data to one or more other devices according to a particular embodiment based on various considerations, including the type of data being transferred. Example data transfer devices considered suitable to operatively attach to a control board include, but are not limited to, data transmission cables, multi-conductor cables, coaxial cables, united serial bus (USB) cables, serial cables, Ethernet cables, (HDMI) cables, (MHL) cables, wireless transmission devices, and any other structure considered suitable for a particular application. Optionally, the control board distal end, or any other suitable portion of a control board, can comprise an HDMI port, or other suitable port or attachment mechanism, such that control board can be operatively attached to another device, such as a computer, network, storage device, computer readable storage medium, or any other suitable device, such as those described herein. Optionally, a handle can omit the inclusion of a control board and an imaging device, first optic fiber, and second optic fiber can be attached to a device separate from a medical device.

Figure 3:
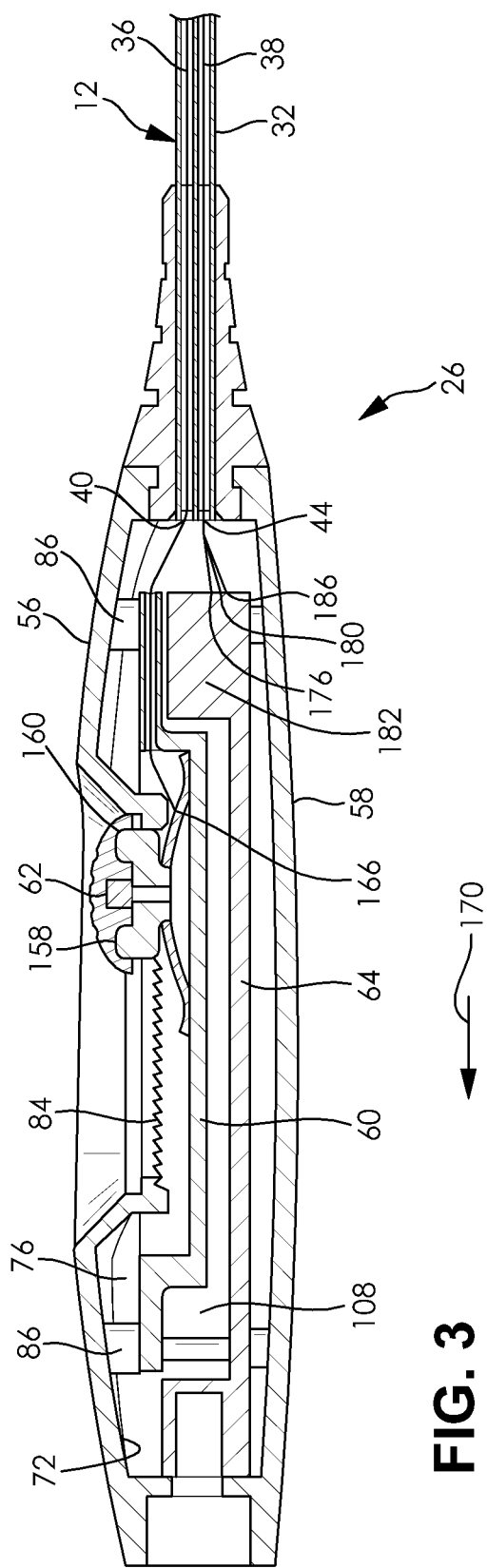
FIG. 3 is a partial sectional view of the medical device illustrated in FIG. 1, taken along line 1A-1A.
Figure 4:
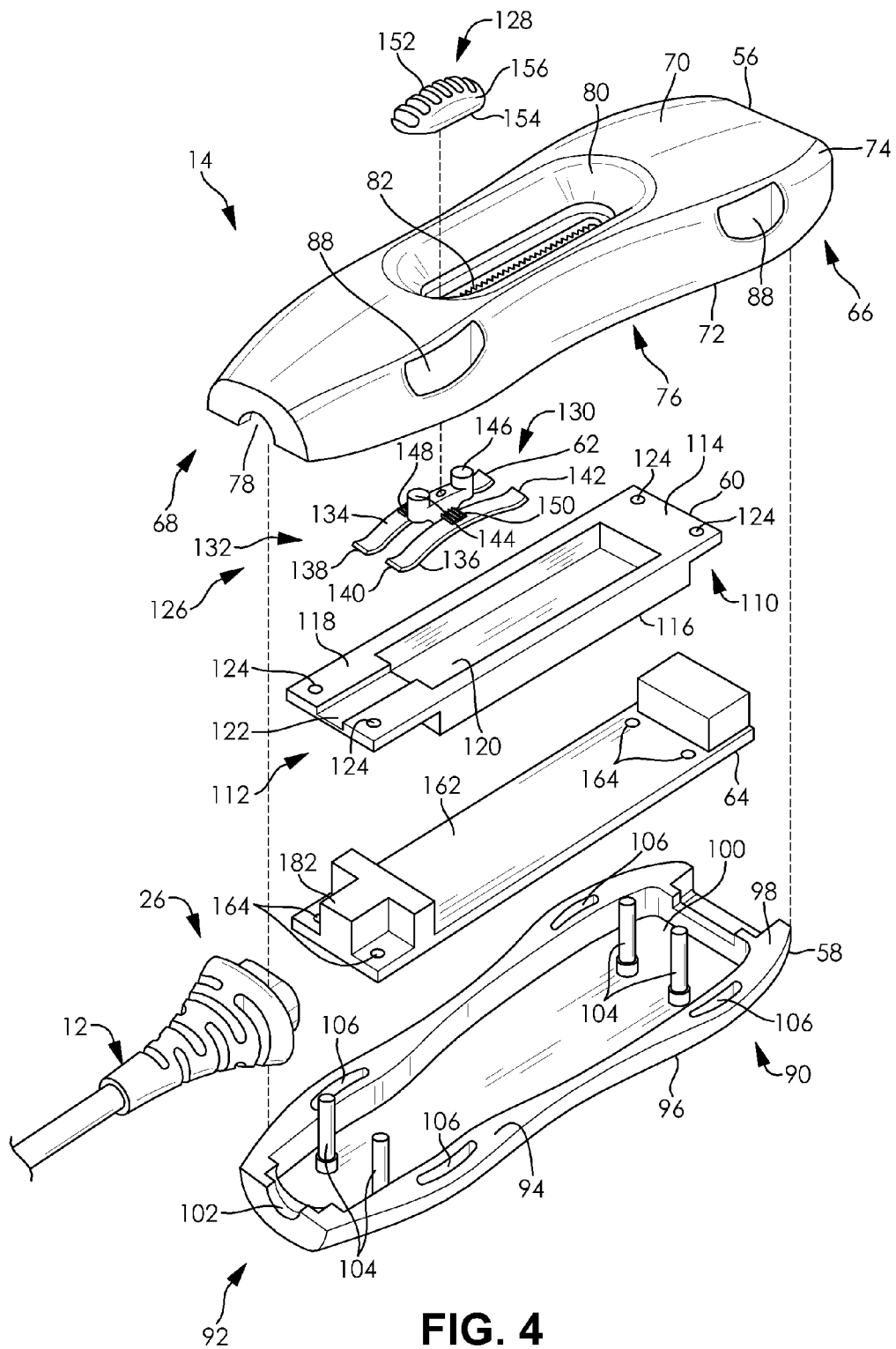
FIG. 4 is a partial exploded view of the medical device illustrated in FIG. 1.

Actuator 62 is moveable between an actuator first position, as shown in FIGS. 1 and 3, and an actuator second position (e.g., such that the actuator is disposed at the proximal end of the actuator opening 80, such that the actuator is disposed between the proximal end and the distal end of the actuator opening 80), not shown. Movement of actuator 62 between the actuator first position and actuator second position results in movement of elongate member 12 between the first straight, or substantially straight, configuration and curved configuration, as described in more detail herein.

Actuator 62 is attached to wire member 16 and is adapted to be releasably fixed in the actuator first position and actuator second position via the interaction of first toothed geometry 82 with first toothed geometry 148 and second toothed geometry 84 with second toothed geometry 150. When a force is applied to actuator control 128 toward housing second portion 58, each of the first base support 138 and second base support 140 compress against, or toward, actuator housing 60 such that actuator 62 can be moved within actuator opening 80. This provides a mechanism to prevent, or substantially prevent, movement of elongate member 12, actuator 62, and/or wire member 16 when elongate member 12 defines a desired radius of curvature. For example, by including a mechanism for releasably fixing actuator 62 along the length of actuator opening 80 the configuration of elongate member 12 can be releasably fixed, or substantially fixed, when a procedure is being performed.

While an actuator that is moveable along the length of an elongate member (e.g., linear actuator) is illustrated, any suitable actuator can be used to move an elongate member between a first configuration and second configuration, and skilled artisans will be able to select a suitable actuator to include on a medical device according to a particular embodiment based on various considerations, including the desired radius of curvature intended to be defined by an elongate member when the actuator is moved between an actuator first position and an actuator second position. Example actuators considered suitable include, but are not limited to, linear actuators, rotatable actuators, pivotable actuators, electro-mechanical actuators, and any other actuator considered suitable for a particular application.

While housing first portion 56 has been illustrated as having first toothed geometry 82 and second toothed geometry 84 and actuator base 126 has been illustrated as having first toothed geometry 148 and second toothed geometry 150, any suitable structural configuration capable of maintaining the position of an actuator in an actuator first portion and/or actuator second position, or a position between the actuator first position and the actuator second position, can be used. Skilled artisans will be able to select a suitable structural configuration to maintain the position of an actuator according to a particular embodiment based on various considerations, including the structural arrangement of an elongate member. Example structural arrangements considered suitable include, but are not limited to, snap-fit configurations, press-fit configurations, and any other structural configuration considered suitable for a particular application.

Wire member 16 can have any suitable outside diameter and length, and skilled artisans will be able to select a suitable outside diameter and length for a wire member according to a particular embodiment based on various considerations, including the desired bodily passage within which a medical device is intended to be used. The inventors have determined that wire members having an outside diameter between about 0.003 inches to about 0.015 inches are suitable. The inventors have also determined that wire members having an outside diameter between about 0.008 inches to about 0.010 inches are suitable.

Wire member 16 can be formed of any suitable material, and skilled artisans will be able to select a suitable material to form a wire member according to a particular embodiment based on various considerations, including the material that forms an elongate member. Example materials considered suitable to form a wire member include, but are not limited to, biocompatible materials, materials that can be made biocompatible, braided materials, polymers, nylon, metals such as stainless steel, titanium, and nickel-titanium alloy (e.g., Nitinol), and any other material considered suitable for a particular application. Any portion, or the entirety, of the length of wire member 16 can be lined and/or coated with any suitable material to reduce the coefficient of friction between the outer surface of wire member 16 and the surface in which the outer surface is intended to, or may, contact. Any suitable lining and/or coating capable of reducing the coefficient of friction is considered suitable, and skilled artisans will be able to select a suitable lining and/or coating according to a particular embodiment based on various considerations, such as the bodily passage within which the medical device is intended to be used. Example lubricious coatings considered suitable to reduce the coefficient of friction include, but are not limited to, polymers such as polyethylene (PE), polytetrafluoroethylene (PTFE), and any other polymer or substance having properties that result in the lowering of the coefficient of friction between two surfaces. By lining and/or coating a portion, or the entirety, of the length of wire member 16 the coefficient of friction between the elements in contact with one another can be reduced when moving elongate member 12 between a curved configuration and a straight, or substantially straight, configuration relative to when a lining and/or coating is not included on a wire member.

In the illustrated embodiment, wire member 16 comprises a wire member first end 166 and a wire member second end 168. Wire member first end 166 can be attached to any suitable portion of actuator 62. In the illustrated embodiment, wire member first end 166 is attached to first protuberance 144. Wire member second end 168 is attached to elongate member 12 within second elongate member lumen 38 proximal to elongate member distal end 28. Wire member 16 extends from wire member first end 166 through first elongate member lumen 36 to elongate member first aperture 54, passes through elongate member first aperture 54 and into second elongate member lumen 38, and is attached to elongate member 12 proximal to elongate member distal end 28. Thus, the wire member 16 extends along a portion of the exterior surface of the elongate member 12, passes through the elongate member body 30 once (e.g., at elongate member first aperture 54), and along a portion of the interior surface of the elongate member 12. Alternative embodiments, such as those described herein, include a wire member that extends along a portion of the exterior surface of an elongate member, passes through the elongate member body more than once (e.g., at least once, twice, a plurality of times, repeatedly), and along a portion of the interior surface of the elongate member.

A wire member can be attached to an actuator (e.g., first protuberance 144) using any suitable method of attachment, and skilled artisans will be able to select a suitable method of attachment between a wire member and an actuator according to a particular embodiment based on various considerations, including the material that forms the wire member and/or actuator. Example methods of attachment between a wire member and an actuator include, but are not limited to, bonding the wire member and actuator to one another, using an adhesive, fusing, welding, tying the wire member to the actuator, passing the wire member through an aperture defined by the actuator (e.g., actuator protuberance) and tying the wire member about the actuator, passing the wire member through an aperture defined by the actuator (e.g., actuator protuberance) and attaching a stopper having an outside diameter greater than the aperture defined by the actuator to the wire member, and any other method of attachment considered suitable for a particular application.

While wire member second end 168 is illustrated as attached to elongate member 12 within second elongate member lumen 38 proximal to elongate member distal end 28, a wire member second end can be attached at any suitable location along the length of an elongate member, and to any suitable portion of an elongate member, using any suitable method of attachment. Skilled artisans will be able to select a suitable location to attach a wire member second end to an elongate member and a suitable method of attachment between a wire member and an elongate member according to a particular embodiment based on various considerations, including the axial length of the elongate member and/or the radius of curvature desired to be achieved by the elongate member when in a second configuration. For example, alternative to wire member second end 168 being attached within second elongate member lumen 38 proximal to elongate member distal end 28, a wire member second end can be attached to the exterior of an elongate member, within an elongate member lumen at the elongate member distal end, or between the elongate member proximal end and the elongate member distal end. For example, alternative to wire member second end 168 being attached to elongate member 12 proximal to elongate member distal end 28, wire member second end 168 can be attached to elongate member distal end 28, within wire member opening 52, within a wire member opening 24" defined by a cap 10", or can be passed through wire member opening 52 and attached using any suitable method of attachment. Example methods of attachment between a wire member and an elongate member considered suitable include, but are not limited to, using an adhesive, welding, fusing (e.g., heat fusing), and any other method of attachment considered suitable for a particular application.

In use, movement of actuator 62 away from elongate member distal end 28, as shown by arrow 170, from the actuator first position, as shown in FIGS. 1 and 3, to the actuator second position (not shown) causes wire member 16 to move in a proximal, or substantially proximal, direction such that wire member first end 166 advances toward housing first portion proximal end 66. This creates tension in wire member 16 that results in movement of wire member second end 168 and elongate member 12 such that elongate member 12 moves from a straight, or substantially straight, configuration, as shown in FIG. 1, to a curved configuration, as shown in FIG. 5, in which elongate member 12 defines curve 172 at a radius of curvature 174. Movement of actuator 62 toward elongate member distal end 28, in a direction opposite that of arrow 170, from the actuator second position to the actuator first position, causes wire member 16 to move in a distal, or substantially distal, direction such that wire member first end 166 advances toward housing first portion distal end 68. This reduces, or eliminates, tension in wire member 16 and results in elongate member 12 returning to the straight, or substantially straight, configuration. Thus, when actuator 62 is in the actuator first position, elongate member 12 is in the straight, or substantially straight, configuration and when actuator 62 is in the actuator second position, elongate member 12 is in the curved configuration.

Optionally, a curve, or slight curve, can be imparted in elongate member 12 between elongate member proximal end 26 and elongate member distal end 28, near elongate member distal end 28, or at elongate member distal end 28, to support movement of elongate member 12 between the straight, or substantially straight, configuration and the curved configuration. Example locations considered suitable to define a curve on an elongate member include, but are not limited to, between an aperture defined by elongate member and elongate member distal end, between an elongate member first aperture and an elongate member distal end, between the distal end of an elongate member first portion and an elongate member distal end, on the distal ¼ of an elongate member, on the distal ⅕ of an elongate member, and any other location considered suitable for a particular application.

When elongate member 12 is in the curved configuration, the portion of elongate member 12 disposed distal to curve 172 is disposed at an angle to the portion of the elongate member 12 disposed proximal to curve 172. The portion of an elongate member disposed distal to a curve can be disposed at any suitable angle to the portion of the elongate member disposed proximal to the curve, and skilled artisans will be able to select a suitable angle according to a particular embodiment based on various considerations, including the desired procedure intended to be performed. Example angles considered suitable include, but are not limited to, an angle between about 0 degrees and 180 degrees, about 45 degrees, about 90 degrees, about 120 degrees, and any other angle considered suitable for a particular application.

The radius of curvature 174 defined by elongate member 12 can vary and be based upon at least the material(s) forming elongate member 12, the location of the actuator second position, the length of elongate member 12, the length of wire member 16, the axial length of actuator opening 80 as it relates to the length of elongate member 12, and/or the distance between first elongate member distal opening 42 and elongate member first aperture 54. For example, if a small radius of curvature 174 is desired, the distance between first elongate member distal opening 42 and elongate member first aperture 54 can be less than the distance between first elongate member distal opening 42 and elongate member second aperture 54 when a large radius of curvature is desired. In addition, if a small radius of curvature 174 is desired, the length of wire member 16 can be reduced as it relates to the length of elongate member 12 and/or the length of actuator opening 80 can be increased as it relates to the length of elongate member 12. Alternatively, if a large radius of curvature 174 is desired, the length of wire member 16 can be increased as it relates to the length of elongate member 12 and/or the length of actuator opening 80 can be decreased as it relates to the length of elongate member 12. Alternatively, adjustment of actuator 62 provides a mechanism for manipulating the radius of curvature 174 defined by elongate member 12 such that a desired radius of curvature can be achieved. Optionally, the residual tension can be eliminated, or substantially eliminated, in wire member 16 when actuator 62 is in the actuator first position (e.g., actuator 62 is near, or at, the distal end of actuator opening 80) to configure elongate member 12 such that it is straight, or substantially straight, along its length when actuator is in the actuator first position. Optionally, an elongate member can be formed such that one or more curves are predefined between an elongate member proximal end and an elongate member distal end. This provides a mechanism for forming an elongate member such that known radii of curvature are defined along the length of an elongate member.

Elongate member 12 can define any suitable radius of curvature 174 along its length when in the curved configuration, and skilled artisans will be able to select a suitable radius of curvature to define along the length of an elongate member according to a particular embodiment based on various considerations, including the procedure intended to be performed. The inventors have determined that elongate members that define a curve having a radius of curvature between about 0.5 cm to about 1.5 cm are suitable. The inventors have also determined that elongate members that define a curve having a radius of curvature about 1.0 cm are suitable.

Movement of an elongate member 12 between a straight, or substantially straight, configuration and a curved configuration allows the medical device 10 to be advanced through tortuous bodily passages, such as airways, sinus cavities, and/or sinus passages. In addition, this allows for the elongate member 12 to be manipulated such that elongate member distal end 28 can be positioned in various configurations to view various aspects of a bodily passage (e.g., during the performance of a sleep study).

Imaging device 18 is disposed through imaging device opening 46 at elongate member distal end 28 and is operatively coupled to a control board 64 by a data transfer cable 20. Imaging device 18 is adapted to obtain images of features and/or material disposed distal to elongate member 12 and transmit the images to control board 64 via data transfer cable 20, or to another device wirelessly, or otherwise. Alternative to imaging device 18 being disposed at elongate member distal end 28, an imaging device can be disposed between an elongate member proximal end and an elongate member distal end such that the imaging device is disposed through an opening defined by the body of the elongate member and can obtain images radially from the elongate member. Optionally, an objective or image-forming lens can be disposed distal to imaging device 18 that is adapted to focus an image upon the imaging device 18.

Imaging device 18 can comprise any suitable device and/or structure capable of obtaining one or more images and transmitting the image to another device. Any suitable imaging device can be used, and skilled artisans will be able to select a suitable imaging device to include with a medical device according to a particular embodiment based on various considerations, including the bodily passage in which the medical device is intended to be used. Example imaging devices considered suitable include, but are not limited to, self-scanning solid state imaging devices, charge coupled (CCD) sensors, complementary metal-oxide semiconductor (CMOS) sensors, and any other imaging device considered suitable for a particular application. An example elongate member having an imaging device considered suitable includes, but is not limited to, an eyeMAX (eyeMAX is a registered trademark of Richard Wolf GmbH Corporation of Knittlingen, Federal Republic of Germany) endoscope with chip on-the-tip, or chip-in-tip, technology.

The data transmitted by imaging device 18 can comprise any suitable form of data, and skilled artisans will be able to select a suitable form of data to transmit from an imaging device according to a particular embodiment based on various considerations, including the type of imaging device desired to be utilized with a medical device. Example forms of data considered suitable include, but are not limited to, analog data, RGB data, RGB data that is digitized and then amplified, digital data, and any other data considered suitable for a particular application.

Data transfer cable 20 has a data transfer cable first end 176 operatively attached to control board 64 and a data transfer cable second end 178 operatively attached to imaging device 18. Data transfer cable 20 can comprise any suitable structure capable of transmitting data from one location to another, and skilled artisans will be able to select a suitable structure to transmit data according to a particular embodiment based on various considerations, including the structural arrangement of an elongate member. Alternatively, cable 20 can be omitted and imaging device 18 can be operatively connected to a wireless data transmission device, located at any suitable location on a medical device 10 (e.g., control board 64), such that the images obtained by the imaging device 18 can be wirelessly transmitted to a control board. Alternatively, imaging device 18 can attached directly to a display to provide still and/or live footage to the display for review by a user. Alternatively, multiple imaging devices can be used in conjunction with, or separate from, one another.

First optical fiber 22 has a first optical fiber first end 180 operatively attached to a light source 182 included on control board 64 and a first optical fiber second end 184 disposed through first optical fiber opening 48. Second optical fiber 24 has a second optical fiber first end 186 operatively attached to light source 182 included on control board 64 and a second optical fiber second end 188 disposed through second optical fiber opening 50. Each of the first optical fiber 22, second optical fiber 24, and light source 182 is described in more detail with respect to FIGS. 18, 18A, 18B, 18C, 18D, 18E, and 18F.

Figure 6:
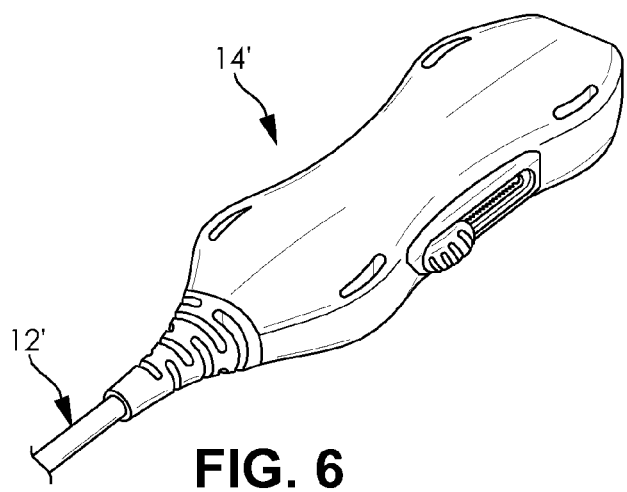
FIG. 6 is a partial perspective view of another exemplary medical device.
Figure 7:
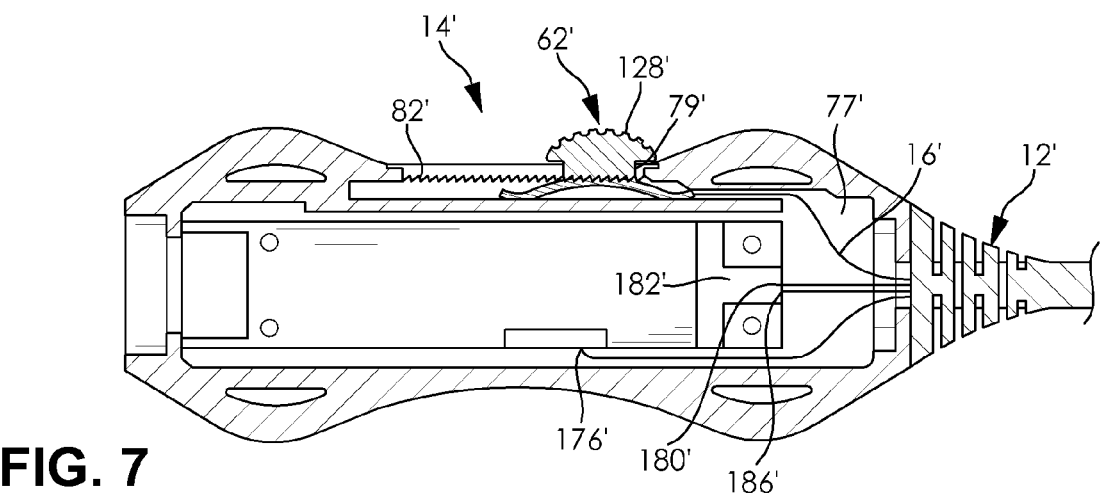
FIG. 7 is a partial sectional view of the medical device illustrated in FIG. 6.
Figure 8:
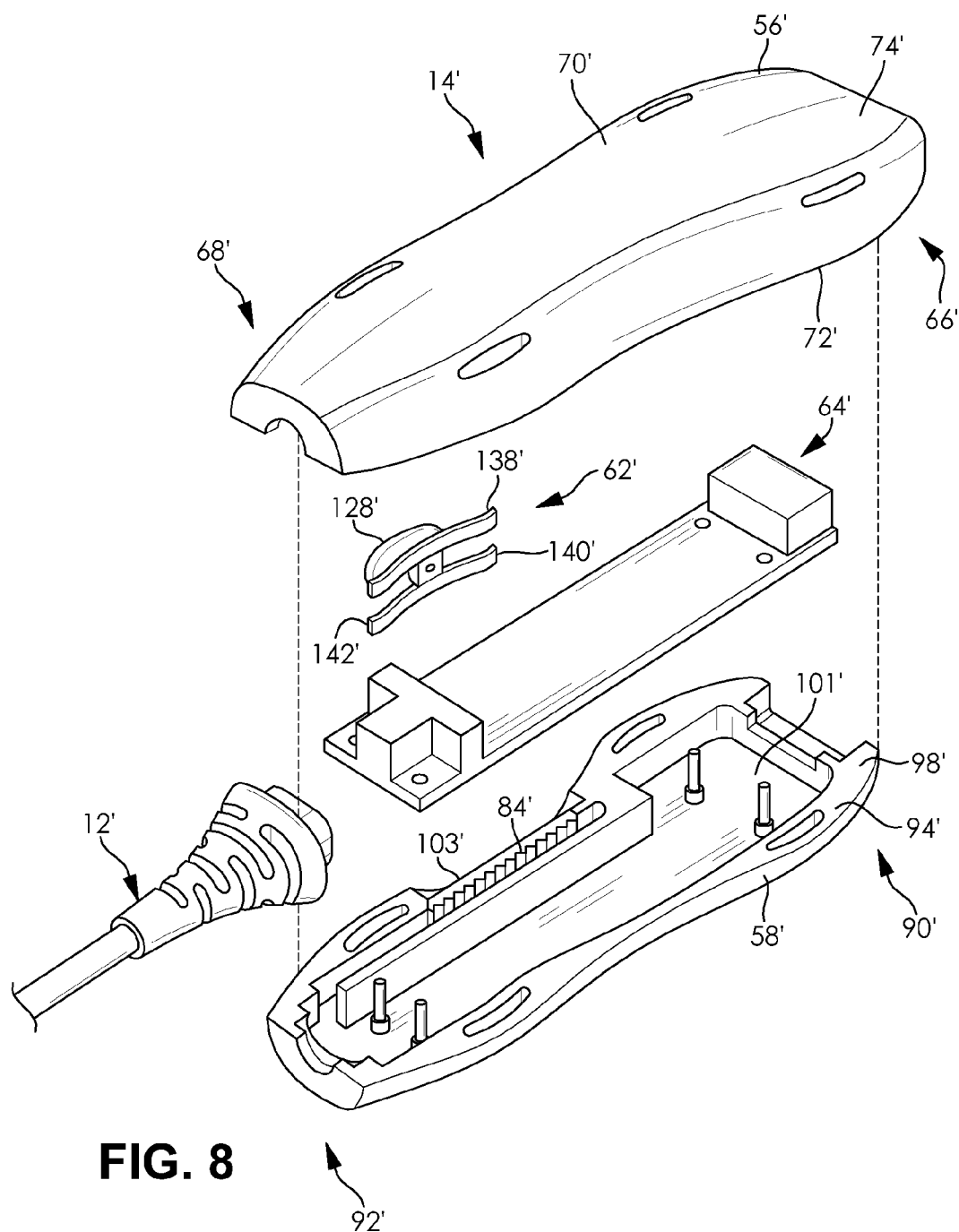
FIG. 8 is a partial exploded view of the medical device illustrated in FIG. 6.

FIGS. 6, 7, and 8 illustrate another exemplary handle 14'. Handle 14' is similar to handle 14 illustrated in FIGS. 1, 3, and 4 and described above, except as detailed below. Reference numbers in FIGS. 6, 7, and 8 refer to the same structural element or feature referenced by the same number in FIGS. 1, 3, and 4, offset by '. Thus, handle 14' comprises a housing first portion 56', housing second portion 58', actuator 62', and houses control board 64'.

In the illustrated embodiment, handle 14' omits the inclusion of an actuator housing (e.g., actuator housing 60), and housing first portion 56' and housing second portion 58' define structure to house a portion of actuator 62' and provide releasable attachment of actuator 62' to housing 14'.

In the illustrated embodiment, housing first portion body 74' defines a housing first portion second cavity 77', housing first portion second notch 79', and first toothed geometry 82'. Housing first portion second cavity 77' extends into housing first portion body 74' from housing first portion second side 72' and is adapted to receive a portion of actuator 62' (e.g., actuator first base support 138'). Housing first portion second notch 79' is defined between housing first portion proximal end 66' and housing first portion distal end 68' and on a side orthogonal, or substantially orthogonal, to housing first portion first side 70'. Housing first portion second notch 79' is defined along the length of housing first portion second cavity 77'. First toothed geometry 82' extends into housing first portion second cavity 77' and is disposed along the length, or a portion of the length, of housing first portion second notch 79'.

In the illustrated embodiment, housing second portion body 98' defines a housing second portion second cavity 101', housing second portion second notch 103', and second toothed geometry 84'. Housing second portion second cavity 101' extends into housing second portion body 98' from housing second portion first side 94' and is adapted to receive a portion of actuator 62' (e.g., actuator second base support 140'). Housing second portion second notch 103' is defined between housing second portion proximal end 90' and housing second portion distal end 92' and on a side orthogonal, or substantially orthogonal, to housing second portion first side 94'. Housing second portion second notch 103' is defined along the length of housing second portion second cavity 101'. Second toothed geometry 84' extends into housing second portion second cavity 101' and is disposed along the length, or a portion of the length, of housing second portion second notch 103'.

Actuator first base support 138' is disposed within the housing first portion second cavity 77' and actuator second base support 140' is disposed within housing second portion second cavity 101'. Actuator base body 142' extends through housing first portion first notch 79' and housing second portion second notch 103' such that actuator control 128' is disposed along the exterior surface of housing first portion 56' and housing second portion 58'. Actuator 62' is moveable between the actuator first position and actuator second position along the length of the opening created by housing first portion first notch 79' and housing second portion second notch 103' when housing first portion 56' and housing second portion 58' are attached to one another.

Figure 9:
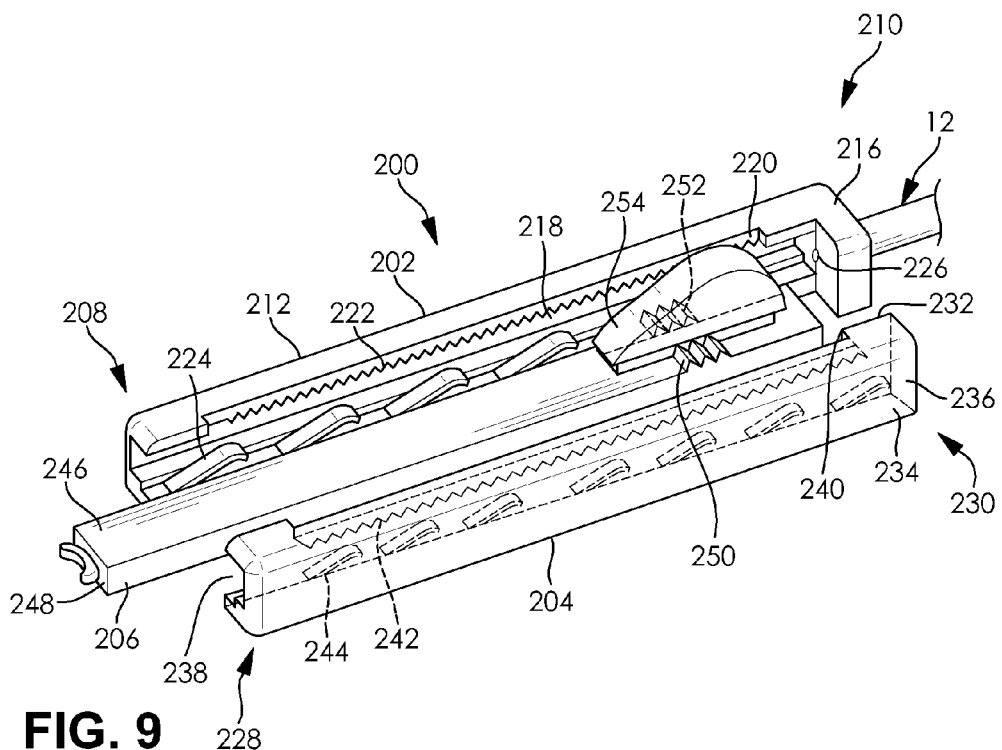
FIG. 9 is a partial exploded view of another exemplary medical device.
Figure 10:
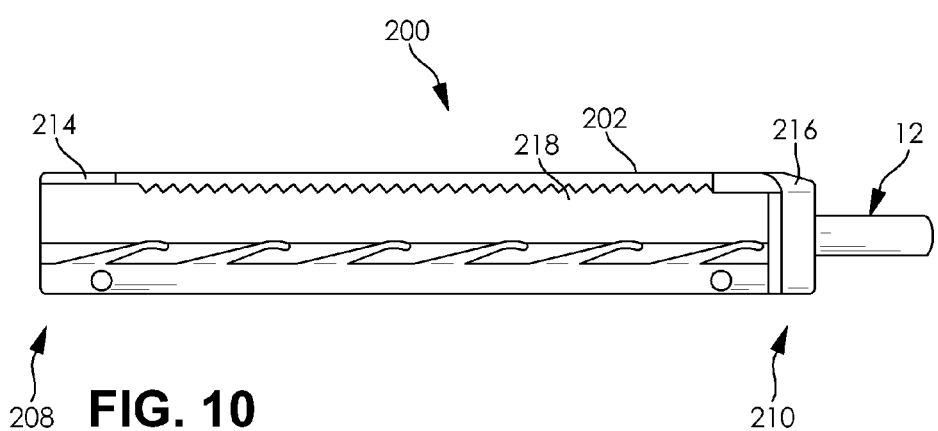
FIG. 10 is a partial side view of the medical device illustrated in FIG. 9.

FIGS. 9 and 10 illustrate another exemplary handle 200 attached to an elongate member 12. Handle comprises a housing first portion 202, housing second portion 204, and an actuator 206.

In the illustrated embodiment, handle 200 omits the inclusion of an actuator housing (e.g., actuator housing 60) and control board (e.g., control board 64). Thus, an imaging device, first optical fiber, and second optical fiber can be operatively attached to a control board separate from a medical device.

In the illustrated embodiment, housing first portion 202 has a housing first portion proximal end 208, housing first portion distal end 210, housing first portion first side 212, housing first portion second side 214, and a housing first portion body 216. Housing first portion first side 212 is opposably facing, or substantially opposably facing, housing first portion second side 214. Housing first portion body 216 defines a housing first portion cavity 218, housing first portion notch 220, first toothed geometry 222, plurality of protuberances 224, and an aperture 226.

Housing first portion cavity 218 extends into housing first portion body 216 from housing first portion second side 214 and is adapted to receive a portion of actuator 206. Housing first portion notch 220 is defined between housing first portion proximal end 208 and housing first portion distal end 210 on a side orthogonal, or substantially orthogonal, to housing first portion second side 214. Housing first portion notch 220 extends through housing first portion body 216 and provides access to housing first portion cavity 218. First toothed geometry 222 extends into housing first portion cavity 218, is disposed along the length, or a portion of the length, of housing first portion notch 220, and is adapted to interact with a portion of actuator 206. Each protuberance of the plurality of protuberances 224 extends from housing first portion body 216 and into housing first portion cavity 218 toward housing first portion distal end 210. Alternatively, each protuberance of a plurality of protuberances can extend from a housing first portion body and into housing first portion cavity toward housing first portion proximal end. Aperture 226 extends through housing first portion body 216, is disposed on housing first portion distal end 210, and is adapted to receive a portion of a wire member (e.g., wire member 16).

In the illustrated embodiment, housing second portion 204 is similar to housing first portion 202, except that it omits the inclusion of an aperture and as described below. Thus, housing second portion 204 has a housing second portion proximal end 228, housing second portion distal end 230, housing second portion first side 232, housing second portion second side 234, and a housing second portion body 236. Housing second portion first side 232 is opposably facing, or substantially opposably facing, housing second portion second side 234. Housing second portion body 236 defines a housing second portion cavity 238, housing second portion notch 240, second toothed geometry 242, and a plurality of protuberances 244.

Housing second portion cavity 238 extends into housing second portion body 236 from housing second portion first side 232 and is adapted to receive a portion of actuator 206. Housing second portion notch 240 is defined between housing second portion proximal end 228 and housing second portion distal end 230 on a side orthogonal, or substantially orthogonal, to housing second portion first side 232. Housing second portion notch 240 extends through housing second portion body 236 and provides access to housing second portion cavity 238. Second toothed geometry 242 extends into housing second portion cavity 238, is disposed along the length, or a portion of the length, of housing second portion notch 240, and is adapted to interact with a portion of actuator 206. Each protuberance of the plurality of protuberances 244 extends from housing second portion body 236 and into housing second portion cavity 238 toward housing second portion distal end 230. Alternatively, each protuberance of a plurality of protuberances can extend from a housing second portion body and into housing second portion cavity toward housing second portion proximal end.

Actuator 206 comprises an actuator body 246 that defines an actuator base 248, first toothed geometry 250, second toothed geometry 252, and an actuator control 254. Actuator base 248 is elongated and adapted to be disposed within the cavity defined by housing first portion cavity 218 and housing second portion cavity 238 when housing first portion 202 is attached to housing second portion 204. Each of the first toothed geometry 250 and second toothed geometry 252 extends outward and away from actuator body 246 from actuator base 248. First toothed geometry 250 is adapted to interact with second toothed geometry 242 and second toothed geometry 252 is adapted to interact with first toothed geometry 222. Actuator control 254 extends from actuator base 248 and through the opening defined by housing first portion notch 220 and housing second portion notch 240 when housing first portion 202 is attached to housing second portion 204. A wire member (not shown) is attached to actuator 206 such that movement of an elongate member (not shown) between a straight, or substantially straight configuration, and a curved configuration can be accomplished. Actuator 206 is adapted to move between an actuator first position and an actuator second position, such as that described above with respect to actuator 62.

FIGS. 11 and 11A illustrate the distal end of another exemplary medical device 310 in a second configuration. Medical device 310 is similar to medical device 10 illustrated in FIGS. 1, 2, 2A, 2B, 2C, 3, 4, and 5 and described above, except as detailed below. Reference numbers in FIGS. 11 and 11A refer to the same structural element or feature referenced by the same number in FIGS. 1, 2, 2A, 2B, 2C, 3, 4, and 5, offset by 300. Thus, medical device 310 comprises an elongate member 312, handle 314, and a wire member 316. Imaging device, data transfer cable, first optical fiber, and second optical fiber have been omitted from the figures for clarity.

In the illustrated embodiment, elongate member 312 has a circular, or substantially circular, cross section. In addition, elongate member body 330 defines a first elongate member lumen 336, elongate member second aperture 355, an elongate member port 357, elongate member port opening 359, second elongate member distal opening 361, and a second elongate member lumen 363.

First elongate member lumen 336 extends from first elongate member proximal opening 340 to imaging device opening 346, first optical fiber opening 348, second optical fiber opening 350, and wire member opening 352. Elongate member second aperture 355 is disposed distal to elongate member first aperture 354 extends through elongate member body 330 and provides access to first elongate member lumen 336. When elongate member 312 is in the first straight, or substantially straight, configuration, each of elongate member first aperture 354 and elongate member second aperture 355 are disposed on a plane that extends from elongate member lengthwise axis.

Wire member 316 extends from actuator (not shown) within first elongate member lumen 336 to elongate member first aperture 354, passes through elongate member first aperture 354 and along the exterior of elongate member 312 to elongate member second aperture 355, passes through elongate member second aperture 355 and into first elongate member lumen 336 and is attached to elongate member 312 proximal to elongate member distal end 328. Thus, the wire member 316 extends along a first portion of the interior surface of the elongate member 312, passes through the elongate member body 330 twice (e.g., at elongate member first aperture 354 and elongate member second aperture 355), extends along a portion of the exterior surface of the elongate member 312, and extends along a second portion of the interior surface of the elongate member 312. The second portion of the interior surface is different than the first portion of the interior surface and is disposed distal to the first portion of the interior surface.

Second elongate member lumen 363 extends from elongate member port opening 359 to second elongate member distal opening 361. The inclusion of a second elongate member lumen 363 provides a mechanism for introducing air, medication, or other fluid into a bodily passage, or removing air, medication, or other fluid from a bodily passage, for treatment purposes or to clean the distal end of an optical fiber or an imaging device disposed within the bodily passage or an elongate member, as described in more detail herein.

FIG. 12 illustrates another exemplary medical device 510 in a second configuration. Medical device 510 is similar to medical device 310 illustrated in FIGS. 11 and 11A, and described above, except as detailed below. Reference numbers in FIG. 12 refer to the same structural element or feature referenced by the same number in FIGS. 11 and 11A, offset by 200. Thus, medical device 510 comprises an elongate member 512, handle 514, and wire member 516.

In the illustrated embodiment, elongate member body 530 defines a plurality of pores 565 that extend through elongate member body 530 and provide access to second elongate member lumen 563. The plurality of pores 565 is disposed between elongate member proximal end 526 and elongate member distal end 528 such that a first portion of the plurality of pores 565 is defined on curve 672 and a second portion of the plurality of pores 565 is defined proximal to curve 672. Each pore of the plurality of pores 565 is spaced longitudinally from another pore of the plurality of pores 565 along the length of elongate member 512. By defining a plurality of pores 565 the elongate member 512 provides a mechanism for introducing air, medication, or other fluid into a bodily passage, or removing air, medication, or other fluid from a bodily passage, for treatment purposes or to clean the distal end of an optical fiber or an imaging device disposed within the bodily passage or an elongate member, as described in more detail herein. For example, a topical anesthetic, such as xylocaine, can be passed through second elongate member lumen 563 and through each pore of the plurality of pores 565 to anesthetize a portion of a bodily passage during the performance of a procedure, or a portion thereof (e.g., sinus passage, airway, sinus cavity).

When elongate member 512 is in a first straight, or substantially straight configuration, each of elongate member first aperture 554 and elongate member second aperture 555 is disposed on a first elongate member longitudinal axis that is parallel to elongate member lengthwise axis and each pore of the plurality of pores 565 is disposed on a second elongate member longitudinal axis that is parallel to elongate member lengthwise axis. Elongate member lengthwise axis, first elongate member longitudinal axis, and second elongate member longitudinal axis are each contained on a plane that passes through elongate member 512.

While a plurality of pores 565 is illustrated as providing access to second elongate member lumen 563, any suitable number of pores can be defined by an elongate member body and can provide access to any lumen defined by an elongate member, and skilled artisans will be able to select a suitable number of pores for an elongate member body to define on an elongate member according to a particular embodiment based on various considerations, including the amount of material desired to be introduced into a bodily passage. Example number of pores considered suitable to define on an elongate member include, but are not limited to, one, at least one, two, a plurality, three, four, five, six, and any other number considered suitable for a particular application.

While a first portion of the plurality of pores 565 is illustrated as disposed on curve 672 and a second portion of the plurality of pores 565 is illustrated as disposed proximal to curve 672, any suitable number of pores of the plurality of pores can be defined on a curve, proximal to a curve, and/or distal to a curve defined by an elongate member when elongate member is a curved configuration, and skilled artisans will be able to select a suitable number of pores to define on a curve, proximal to a curve, and/or distal to a curve according to a particular embodiment based on various considerations, including the bodily passage within which a medical device is intended to be used. Example number of pores considered suitable to define on a curve, proximal to a curve, and/or distal to a curve defined by an elongate member include, but are not limited to, zero, one, at least one, two, a plurality, three, four, five, six, and any other number considered suitable for a particular application.

While the plurality of pores 565 is illustrated as being positioned on a plane that contains each of the elongate member first aperture 554, elongate member second aperture 555, and elongate member lengthwise axis, each pore of a plurality of pores can be positioned at any suitable location about an elongate member. Skilled artisans will be able to select a suitable position to locate a pore, or a plurality of pores, about an elongate member according to a particular embodiment based on various considerations, including the structural arrangement of a bodily passage within which a medical device is intended to be used. Example locations considered suitable to position a pore, or a plurality of pores, include, but are not limited to, such that a pore, or a plurality of pores, is disposed on a longitudinal axis that is parallel to the lengthwise axis of an elongate member and each of the longitudinal axis and the lengthwise axis are contained on a plane that passes through the elongate member, such that a first pore, or first plurality of pores, is disposed on a first elongate member longitudinal axis that is parallel to the lengthwise axis of an elongate member and a second pore, or second plurality of pores, is disposed on a second elongate member longitudinal axis that is different than the first elongate member longitudinal axis and is parallel to the lengthwise axis of the elongate member and each of the first longitudinal axis and lengthwise axis are contained on a first plane that passes through the elongate member and each of the second longitudinal axis and lengthwise axis are contained on a second plane that passes through the elongate member, the first plane and the second plane can be coplanar, or the first plane can be disposed at any suitable angle to the second plane, and any other location considered suitable for a particular application. Example angles considered suitable to position a first plane with respect to a second plane include, but are not limited to, orthogonal, a 45 degree angle, an angle between about 1 degree to about 90 degrees, an angle between about 90 degrees to about 180 degrees, an angle between about 180 degrees to about 270 degrees, an angle between about 270 degrees to about 360 degrees, and any other angle considered suitable for a particular application.

FIGS. 13 and 13A illustrate the distal end of another exemplary medical device 710. Medical device 710 is similar to medical device 510 illustrated in FIG. 12, and described above, except as detailed below. Reference numbers in FIGS. 13 and 13A refer to the same structural element or feature referenced by the same number in FIG. 12, offset by 200. Thus, medical device 710 comprises an elongate member 712 and wire member 716.

In the illustrated embodiment, elongate member 712 omits the inclusion of elongate member port (e.g., elongate member port 557), second elongate member lumen (e.g., second elongate member lumen 563), and the plurality of pores (e.g., plurality of pores 565). Elongate member body 730 defines a first plurality of reliefs 767 and a second plurality of reliefs 769. Any suitable type of relief (e.g., localized region of an elongate member that is relatively more flexible than another different region of the elongate member) capable of increasing the flexibility of an elongate member can be used and skilled artisans will be able to select a suitable relief according to a particular embodiment based on various considerations, including the material forming an elongate member. Example reliefs considered suitable include on an elongate member include, but are not limited to, including a relief that comprises a first portion positioned along the length of an elongate member that is formed of a first material that is relatively more flexible, or substantially relatively more flexible, relative to a second portion positioned along the length of the elongate member that is formed of a second material (e.g., same as the first material, different than the first material), defining one or more recesses along the length of an elongate member, and any other relief considered suitable for a particular application. For example, a relief can comprise a first portion of an elongate member that has a cross-sectional thickness that is less than the cross-sectional thickness of a second portion of the elongate member.

In the illustrated embodiment, the first plurality of reliefs 767 is a first plurality of recesses 771 and the second plurality of reliefs 769 is a second plurality of recesses 773. Elongate member body 730 defines first plurality of recesses 771 between elongate member first aperture 754 and elongate member second aperture 755 and second plurality of recesses 773 between elongate member proximal end (not shown) and elongate member distal end 728. Thus, the first plurality of reliefs 767 is defined between elongate member first aperture 754 and elongate member second aperture 755 and the second plurality of reliefs 769 is disposed between elongate member proximal end (not shown) and elongate member distal end 728. Elongate member first aperture 754, elongate member second aperture 755, and each recess of the first plurality of recesses 771 is disposed on a first elongate member longitudinal axis 775 that is parallel to elongate member lengthwise axis 735. Elongate member first aperture 754, elongate member second aperture 755, and each recess of the first plurality of recesses 771 are spaced longitudinally along the length of elongate member 712. Elongate member lengthwise axis 735 and first elongate member longitudinal axis 775 are each contained on a first plane that passes through elongate member 712. Each recess of the second plurality of recesses 773 is disposed on a second elongate member longitudinal axis 777 that is parallel to elongate member lengthwise axis 735 and contained on the first plane that passes through elongate member 712. Each recess of the second plurality of recesses 773 is spaced longitudinally along the length of elongate member 712 from another recess of the second plurality of recesses 773. In the illustrated embodiment, each feature disposed on the first elongate member longitudinal axis 775 is disposed on a first side of elongate member 712 that is opposably facing, or substantially opposably facing, a second side of elongate member 712 on which each feature disposed on the second elongate member longitudinal axis 777 is disposed.

Each recess of the first plurality of recesses 771 and second plurality of recesses 773 can extend through a portion of elongate member body 730 or through the entirety of elongate member body 730 to provide access to a lumen defined by elongate member (e.g., first elongate member lumen 736, second elongate member lumen 563). The inclusion of a first plurality of recesses 771 and second plurality of recesses 773 provides a mechanism for reducing the amount of force required to define curve 872 along the length of elongate member 712 relative to an elongate member that does not define a first and/or second plurality of reliefs.

While a first plurality of reliefs 767 (e.g., first plurality of recesses 771) is illustrated as disposed on a first side that is opposably facing, or substantially opposably facing, a second side on which a second plurality of reliefs 769 (e.g., second plurality of recesses 773) is disposed, an elongate member body can define any suitable number of reliefs (e.g., recesses) along the length of the elongate member at any suitable location. Skilled artisans will be able to select a suitable number of reliefs and/or recesses to define on an elongate member and a suitable position to locate a relief and/or recess according to a particular embodiment based on various considerations, including the desired second configuration of an elongate member. Example number of reliefs and/or recesses considered suitable to define on an elongate member include, but are not limited to, one, at least one, two, a plurality, three, four, five, six, a first plurality, a second plurality, a third plurality, a fourth plurality, and any other number considered suitable for a particular application. Optionally, an elongate member body can omit the inclusion of a first plurality of reliefs (e.g., first plurality of recesses) and/or a second plurality of reliefs (e.g., second plurality of recesses).

Example locations considered suitable to position a first relief, a first recess, a first plurality of reliefs, or a first plurality of recesses, relative to a second relief, a second recess, a second plurality of reliefs, or second plurality of recesses include, but are not limited to, such that the first relief, first recess, first plurality of reliefs, or the first plurality of recesses, is disposed on a first longitudinal axis that is parallel to the lengthwise axis of an elongate member and each of the first longitudinal axis and the lengthwise axis are contained on a first plane that passes through the elongate member and the second relief, second recess, second plurality of reliefs, or the second plurality of recesses, is disposed on a second longitudinal axis that is parallel to the lengthwise axis of an elongate member and each of the second longitudinal axis and the lengthwise axis are contained on a second plane that passes through the elongate member, the first plane and the second plane can be coplanar, or the first plane can be disposed at any suitable angle to the second plane. Example angles considered suitable to position a first plane with respect to a second plane include, but are not limited to, orthogonal, a 45 degree angle, an angle between about 1 degree to about 90 degrees, an angle between about 90 degrees to about 180 degrees, an angle between about 180 degrees to about 270 degrees, an angle between about 270 degrees to about 360 degrees, and any other angle considered suitable for a particular application. Thus, a first relief, first recess, first plurality of reliefs, or first plurality of recesses, can be disposed linearly, or offset, from a second relief, second recess, second plurality of reliefs, or second plurality of recesses, about the circumference of the elongate member.

While each recess of the first plurality of recesses 771 and second plurality of recesses 773 is illustrated as tapered, a recess defined by an elongate member body can have any suitable structural configuration, and skilled artisans will be able to select a suitable structural configuration for a recess according to a particular embodiment based on various considerations, including the desired radius of curvature intended to be defined by an elongate member. Example structural configurations considered suitable include, but are not limited to, rectangular, square, curved, circular, oblong, and any other structural configuration considered suitable for a particular application.

FIGS. 14, 14A, 14B, and 15 illustrate the distal end of another exemplary medical device 910. Medical device 910 is similar to medical device 310 illustrated in FIGS. 11 and 11A, and described above, except as detailed below. Reference numbers in FIGS. 14, 14A, 14B, and 15 refer to the same structural element or feature referenced by the same number in FIGS. 11, and 11A, offset by 600. Thus, medical device 910 comprises an elongate member 912 and wire member 916.

In the illustrated embodiment, elongate member 912 omits the inclusion of elongate member port (e.g., elongate member port 357), port opening (e.g., port opening 359), second elongate member distal opening (e.g., second elongate member distal opening 361), and second elongate member lumen (e.g., second elongate member lumen 363). Elongate member body 930 defines an elongate member first aperture 954, elongate member second aperture 955, elongate member third aperture 979, and elongate member fourth aperture 981. Elongate member first aperture 954 is disposed between elongate member proximal end (not shown) and elongate member distal end 928. Elongate member second aperture 955 is disposed between elongate member first aperture 954 and elongate member distal end 928. Elongate member third aperture 979 is disposed between elongate member second aperture 955 and elongate member distal end 928. Elongate member fourth aperture 981 is disposed between elongate member third aperture 979 and elongate member distal end 928. Thus, elongate member first aperture 954, elongate member second aperture 955, elongate member third aperture 979, and elongate member fourth aperture 981 are spaced longitudinally along the length of elongate member 912. Each of elongate member first aperture 954, elongate member second aperture 955, elongate member third aperture 979, and elongate member fourth aperture 981 extends through elongate member body 930 and provides access to elongate member lumen 936 and is adapted to receive a portion of wire member 916.

Wire member 916 extends from actuator (not shown) within elongate member lumen 936 to elongate member first aperture 954, passes through elongate member first aperture 954 and along the exterior of elongate member 912 to elongate member second aperture 955, passes through elongate member second aperture 955 and into elongate member lumen 936 and extends to elongate member third aperture 979, passes through elongate member third aperture 979 and along the exterior of elongate member 912 to elongate member fourth aperture 981, passes through elongate member fourth aperture 981 and into elongate member lumen 936 and is attached to elongate member 912 proximal to elongate member distal end 928. Thus, the wire member 916 extends along a first portion of the interior surface of the elongate member 912, passes through the elongate member body 930 a plurality of times (e.g., at elongate member first aperture 954, elongate member second aperture 955, elongate member third aperture 979, elongate member fourth aperture 981), extends along a first portion of the exterior surface of the elongate member 912, extends across the elongate member lumen 936, extends along a second portion of the exterior surface of the elongate member 912, and extends along a second portion of the interior surface of the elongate member 912. The second portion of the interior surface is different than the first portion of the interior surface and is disposed distal to the first portion of the interior surface. The second portion of the exterior surface is different than the first portion of the exterior surface and is disposed distal to the first portion of the exterior surface.

In the illustrated embodiment, each of elongate member first aperture 954 and elongate member second aperture 955 is disposed on a first elongate member longitudinal axis 975 that is parallel to elongate member lengthwise axis 935. Each of elongate member third aperture 979 and elongate member fourth aperture 981 is disposed on a second elongate member longitudinal axis 977 that is parallel to elongate member lengthwise axis 935. First elongate member longitudinal axis 975 is different than second elongate member longitudinal axis 977. First elongate member longitudinal axis 975 and second elongate member longitudinal axis 977 are each contained on a plane that contains elongate member lengthwise axis 935 and passes through elongate member 912. In the illustrated embodiment, each feature disposed on the first elongate member longitudinal axis 975 is disposed on a first side of elongate member 912 that is opposably facing, or substantially opposably facing, a second side of elongate member 912 on which each feature disposed on the second elongate member longitudinal axis 977 is disposed. This configuration provides a mechanism for defining more than one curve along the length of elongate member 912 such that elongate member distal end 928 can be positioned in a variety of different arrangements when disposed in a bodily passage (e.g., during the performance of a sleep study).

While each feature disposed on first elongate member longitudinal axis 975 is illustrated as disposed on a first side that is opposably facing, or substantially opposably facing, a second side on which each feature disposed on second elongate member longitudinal axis 977 is disposed, the features disposed on a first elongate member longitudinal axis can be positioned at any suitable location on an elongate member relative to the features disposed on a second elongate member longitudinal axis. Skilled artisans will be able to select a suitable position to locate the features disposed on a first elongate member longitudinal axis on an elongate member relative to the features disposed on a second elongate member longitudinal axis according to a particular embodiment based on various considerations, including the anatomy of the bodily passage within which a medical device is intended to be used. For example, a first elongate member longitudinal axis can be positioned at any suitable location about an elongate member relative to second elongate member longitudinal axis. Example locations considered suitable to position a first elongate member longitudinal axis on an elongate member relative to a second elongate member longitudinal axis include, but are not limited to, such that a first longitudinal axis and the lengthwise axis of an elongate member are contained on a first plane that passes through the elongate member and a second longitudinal axis and the lengthwise axis of the elongate member are contained on a second plane that passes through the elongate member. The first plane and the second plane can be coplanar, or the first plane can be disposed at any suitable angle to the second plane. Example angles considered suitable to position a first plane with respect to a second plane include, but are not limited to, orthogonal, a 45 degree angle, an angle between about 1 degree to about 90 degrees, an angle between about 90 degrees to about 180 degrees, an angle between about 180 degrees to about 270 degrees, an angle between about 270 degrees to about 360 degrees, and any other angle considered suitable for a particular application. Thus, a first aperture and second aperture can be disposed linearly, or offset, from a third aperture and fourth aperture about the circumference of the elongate member.

Alternative to elongate member first aperture 954 being disposed on a first elongate member longitudinal axis 975 that is parallel to elongate member lengthwise axis 935, an elongate member first aperture can comprise a first elongate member distal opening that is disposed an on elongate member first portion, such as first elongate member distal opening 42 illustrated in FIG. 2 that is disposed on elongate member first portion 32.

Figure 14:
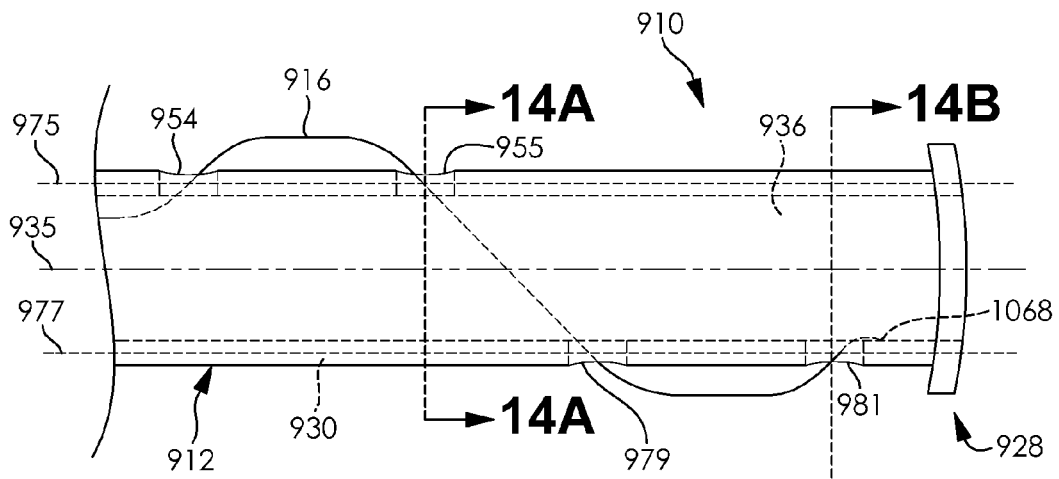
FIG. 14 is a partial side view of another exemplary medical device in a first configuration.
Figure 14A:
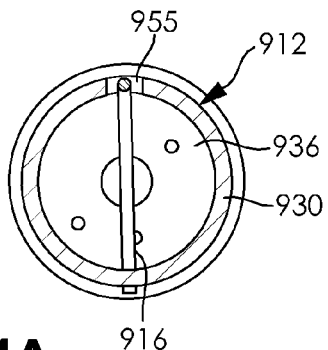
FIG. 14A is a sectional view of the medical device illustrated in FIG. 14, taken along line 14A-14A.
Figure 14B:
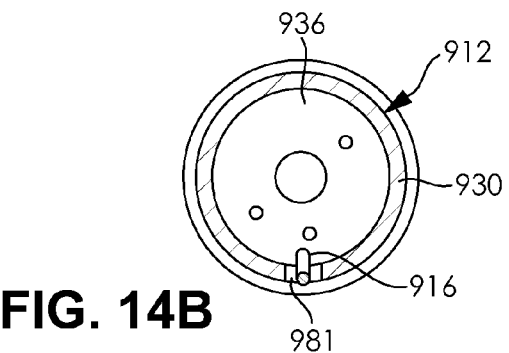
FIG. 14B is a sectional view of the medical device illustrated in FIG. 14, taken along line 14B-14B.
Figure 15:
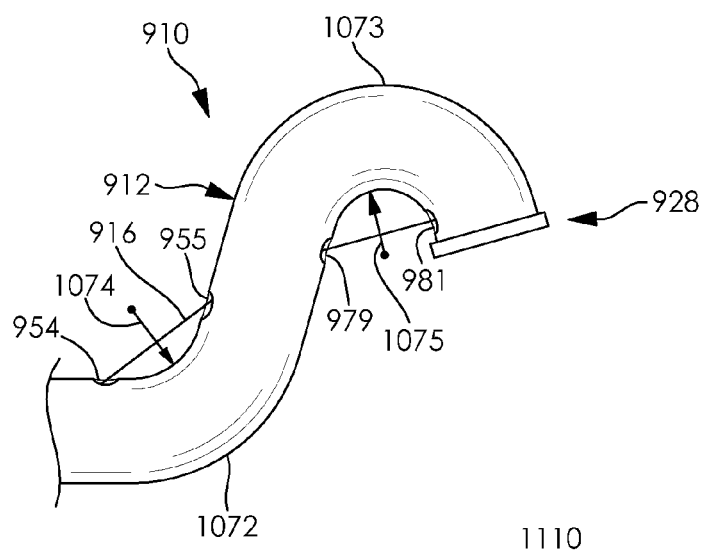
FIG. 15 is a partial side view of the medical device illustrated in FIG. 14 in a second configuration.

In use, as described herein, movement of actuator (not shown) away from elongate member distal end 928 from the actuator first position to the actuator second position results in movement of wire member second end 1068 and elongate member 912 such that elongate member 912 moves from a straight, or substantially straight, configuration, as shown in FIG. 14, to a curved configuration, as shown in FIG. 15, in which elongate member 912 defines a first curve 1072 at a first radius of curvature 1074 and a second curve 1073 at a second radius of curvature 1075. Each of the first radius of curvature 1074 and second radius of curvature 1075 can comprise any suitable radius of curvature, such as those described herein. Movement of actuator (not shown) toward elongate member distal end 928 results in elongate member 912 returning to its straight, or substantially straight, configuration. Thus, when actuator (not shown) is in the actuator first position, elongate member 912 is in the straight, or substantially straight, configuration and when actuator (not shown) is in the actuator second position, elongate member 912 is in the curved configuration.

When elongate member 912 is in the curved configuration, the portion of elongate member 912 disposed between first curve 1072 and second curve 1073 is disposed at a first angle to the portion of elongate member 912 disposed proximal to first curve 1072. In addition, the portion of elongate member 912 disposed between first curve 1072 and second curve 1073 is disposed at a second angle to the portion of elongate member 912 disposed distal to second curve 1073. The portion of an elongate member disposed between a first curve and a second curve can be disposed at any suitable angle to the portion of the elongate member disposed proximal to the first curve and the portion of the elongate member disposed distal to the second curve. Skilled artisans will be able to select a suitable angle according to a particular embodiment based on various considerations, including the desired procedure intended to be performed. Example angles considered suitable include, but are not limited to, an angle between about 0 degrees and 180 degrees, about 45 degrees, about 90 degrees, about 120 degrees, and any other angle considered suitable for a particular application.

Each of the first radius of curvature 1074 and second radius of curvature 1075 defined by elongate member 912 can be determined based upon at least the characteristics listed and described above with respect to radius of curvature 174. For example, the radius of curvature for a curve defined by an elongate member can be determined based upon at least the distance between elongate member first aperture and elongate member second aperture, the distance between elongate member second aperture and elongate member third aperture, and/or the distance between elongate member third aperture and elongate member fourth aperture. For example, if a small first radius of curvature 1074 is desired, the distance between elongate member first aperture 954 and elongate member second aperture 955 can be less than the distance between elongate member first aperture 954 and elongate member second aperture 955 when a large first radius of curvature is desired. In addition, if a small second radius of curvature 1075 is desired, the distance between elongate member third aperture 979 and elongate member fourth aperture 981 can be less than the distance between elongate member third aperture 979 and elongate member fourth aperture 981 when a large second radius of curvature is desired. In the embodiment illustrated, the elongate member has a first radius of curvature 1074 that is greater than a second radius of curvature 1075. However, other arrangements are considered suitable. For example, an elongate member can define a first radius of curvature that is greater than, less than, equal to, or substantially equal to, a second radius of curvature.

This configuration provides a mechanism for defining more than one curve along the length of elongate member 912, which allows for the positioning of elongate member distal end 928 to vary depending on the location of the apertures defined by elongate member body 930, first radius of curvature 1074, and second radius of curvature 1075.

Alternative to an elongate member defining a curve at a radius of curvature along its length (e.g., first curve 1072, second curve 1073), an elongate member can be configured to collapse and define a kink along the length of the elongate member upon movement of actuator from an actuator first position to an actuator second position such that the elongate member define an apex along its length.

Figure 15A:
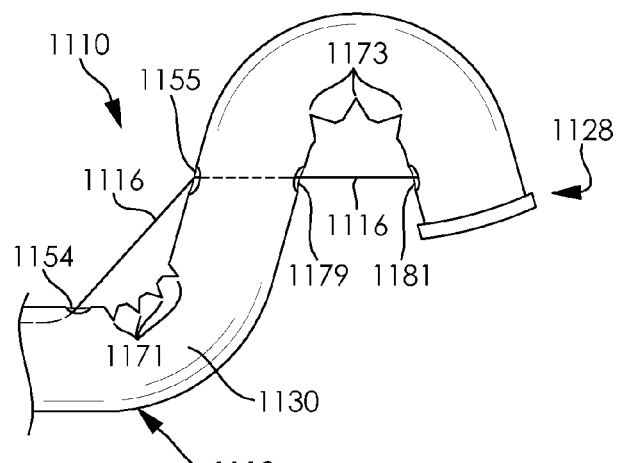
FIG. 15A is a partial side view of another exemplary medical device in a second configuration.

FIG. 15A illustrates the distal end of another exemplary medical device 1110. Medical device 1110 is similar to medical device 910 illustrated in FIGS. 14, 14A, 14B, and 15, and described above, except as detailed below. Reference numbers in FIG. 15A refer to the same structural element or feature referenced by the same number in FIGS. 14, 14A, 14B, and 15, offset by 200. Thus, medical device 1110 comprises an elongate member 1112 and wire member 1116.

In the illustrated embodiment, elongate member body 1130 defines a first plurality of recesses 1171 and a second plurality of recesses 1173. First plurality of recesses 1171 is disposed between elongate member first aperture 1154 and elongate member second aperture 1155. When elongate member 1112 is in the straight, or substantially straight, configuration, each of the elongate member first aperture 1154, elongate member second aperture 1155, and the first plurality of recesses 1171 is disposed on a first elongate member longitudinal axis that is disposed parallel to the lengthwise axis of elongate member 1112. The second plurality of recesses 1173 is disposed between elongate member third aperture 1179 and elongate member fourth aperture 1181. When elongate member 1112 is in the straight, or substantially straight, configuration, each of the elongate member third aperture 1179, elongate member fourth aperture 1181, and the second plurality of recesses 1173 is disposed on a second elongate member longitudinal axis that is disposed parallel to the lengthwise axis of the elongate member 1112. Thus, the elongate member body 1130 defines a first relief between elongate member first aperture 1154 and elongate member second aperture 1155 and a second relief between elongate member third aperture 1179 and elongate member fourth aperture 1181. In the illustrated embodiment, each of the first longitudinal axis and second longitudinal axis is contained on a plane that contains the elongate member lengthwise axis and passes through the elongate member 1112. In addition, each feature disposed on the first elongate member longitudinal axis is disposed on a first side of elongate member 1112 that is opposably facing, or substantially opposably facing, a second side of elongate member 1112 on which each feature disposed on the second elongate member longitudinal axis is disposed.

Elongate member first aperture 1154, elongate member second aperture 1155, and each recess of the first plurality of recesses 1171 are spaced longitudinally along the length of elongate member 1112. Elongate member third aperture 1179, elongate member fourth aperture 1181, and each recess of the second plurality of recesses 1173 are spaced longitudinally along the length of elongate member 1112. The inclusion of a plurality recesses between elongate member first aperture 1154 and elongate member second aperture 1155 and between elongate member third aperture 1179 and elongate member fourth aperture 1181 provides a mechanism for defining two curves along the length of elongate member 1112 and decreases the force necessary to define each curve as compared to a configuration that does not include a first plurality of recesses 1171 or a second plurality of recesses 1173.

While a plurality of reliefs (e.g., plurality of recesses 1171) is illustrated as positioned between elongate member first aperture 1154 and elongate member second aperture 1155 and a plurality of reliefs (e.g., plurality of recesses 1173) is illustrated as positioned between elongate member third aperture 1179 and elongate member fourth aperture 1181, any suitable number of reliefs (e.g., recesses) can be positioned between one or more apertures defined on an elongate member. Skilled artisans will be able to select a suitable number of reliefs (e.g., recesses) to define on an elongate member according to a particular embodiment based on various considerations, including the desired flexibility of an elongate member at a particular location. Example number of reliefs (e.g., recesses) considered suitable to define on an elongate member include, but are not limited to, one, at least one, two, a plurality, three, four, five, six, and any other number considered suitable for a particular application.

Figure 15B:
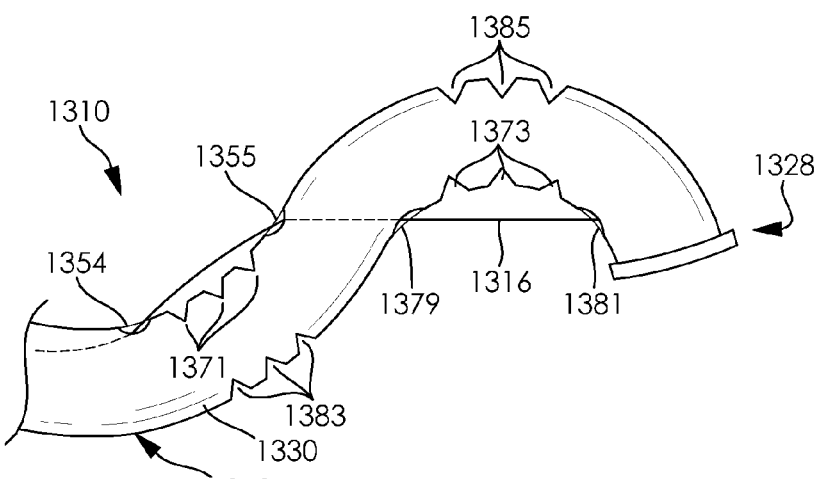
FIG. 15B is a partial side view of another exemplary medical device in a second configuration.

FIG. 15B illustrates the distal end of another exemplary medical device 1310. Medical device 1310 is similar to medical device 1110 illustrated in FIG. 15A, and described above, except as detailed below. Reference numbers in FIG. 15B refer to the same structural element or feature referenced by the same number in FIG. 15A, offset by 200. Thus, medical device 1310 comprises an elongate member 1312 and wire member 1316.

In the illustrated embodiment, elongate member body 1330 defines a third plurality of recesses 1383 and a fourth plurality of recesses 1385. Third plurality of recesses 1383 is disposed between elongate member proximal end (not shown) and elongate member third aperture 1379. When elongate member 1312 is in the straight, or substantially straight, configuration, each of the elongate member third aperture 1379, elongate member fourth aperture 1381, second plurality of recesses 1373, and the third plurality of recesses 1383 is disposed on the second elongate member longitudinal axis that is disposed parallel to the lengthwise axis of elongate member 1312. Fourth plurality of recesses 1385 is disposed between elongate member second aperture 1355 and elongate member distal end 1328. When elongate member 1312 is in the straight, or substantially straight, configuration, each of the elongate member first aperture 1354, elongate member second aperture 1355, first plurality of recesses 1371, and the fourth plurality of recesses 1385 is disposed on the first elongate member longitudinal axis that is disposed parallel to the lengthwise axis of the elongate member 1312 and contains. Thus, the elongate member body 1330 defines a third relief between elongate member proximal end (not shown) and elongate member third aperture 1379 and a fourth relief between elongate member second aperture 1355 and elongate member distal end 1328.

Elongate member first aperture 1354, elongate member second aperture 1355, each recess of the first plurality of recesses 1371, and each recess of the fourth plurality of recesses 1385 are spaced longitudinally along the length of elongate member 1312. Elongate member third aperture 1379, elongate member fourth aperture 1381, each recess of the second plurality of recesses 1373, and each recess of the plurality of third recesses 1383 are spaced longitudinally along the length of elongate member 1312. In the illustrated embodiment, each of the first longitudinal axis and second longitudinal axis is contained on a plane that passes through elongate member 1312 and contains the elongate member lengthwise axis. In addition, each feature disposed on the first elongate member longitudinal axis is disposed on a first side of elongate member 1312 that is opposably facing, or substantially opposably facing, a second side of elongate member 1312 on which each feature disposed on the second elongate member longitudinal axis is disposed. Optionally, elongate member 1312 can omit the inclusion of third plurality of recesses 1383 and/or fourth plurality of recesses 1385. The inclusion of a third plurality of recesses 1383 and a fourth plurality of recesses 1385 provides a mechanism for defining two curves along the length of an elongate member and decreases the force necessary to define each curve as compared to a configuration that does not include a third plurality of recesses 1383 or a fourth plurality of recesses 1385.

While a plurality of reliefs (e.g., recesses) is illustrated as positioned between elongate member proximal end (not shown) and elongate member third aperture 1379 and between elongate member second aperture 1355 and elongate member distal end 1328, any suitable number of reliefs (e.g., recesses) can be positioned between one or more apertures defined on an elongate member. Skilled artisans will be able to select a suitable number of reliefs (e.g., recesses) to define on an elongate member according to a particular embodiment based on various considerations, including the desired flexibility of an elongate member at a particular location. Example number of reliefs (e.g., recesses) considered suitable to define on an elongate member include, but are not limited to, one, at least one, two, a plurality, three, four, five, six, and any other number considered suitable for a particular application.

While third plurality of recesses 1383 is illustrated as positioned on a second longitudinal axis that is parallel to the lengthwise axis of elongate member 1312 and contains elongate member third aperture 1379 and elongate member fourth aperture 1381 and fourth plurality of recesses 1385 is illustrated as positioned on a first longitudinal axis that is parallel to the lengthwise axis of elongate member 1312 and contains elongate member first aperture 1354 and elongate member second aperture 1355, a third plurality of recesses and/or fourth plurality of recesses can be positioned at any suitable location about the circumference of an elongate member. Skilled artisans will be able to select a suitable position to locate a plurality of recesses according to a particular embodiment based on various considerations, including the desired flexibility of an elongate member. Example locations considered suitable to position a third plurality of recesses relative to a fourth plurality of recesses include, but are not limited to, such that a third plurality of recesses is disposed on a first longitudinal axis that is parallel to the lengthwise axis of an elongate member and each of the first longitudinal axis and the lengthwise axis are contained on a first plane that passes through the elongate member and a fourth plurality of recesses is disposed on a second longitudinal axis that is parallel to the lengthwise axis of an elongate member and each of the second longitudinal axis and the lengthwise axis are contained on a second plane that passes through the elongate member, the first plane and the second plane can be coplanar, or the first plane can be disposed at any suitable angle to the second plane. Example angles considered suitable to position a first plane with respect to a second plane include, but are not limited to, orthogonal, a 45 degree angle, an angle between about 1 degree to about 90 degrees, an angle between about 90 degrees to about 180 degrees, an angle between about 180 degrees to about 270 degrees, an angle between about 270 degrees to about 360 degrees, and any other angle considered suitable for a particular application. Thus, a third plurality of recesses can be disposed linearly, or offset, from a fourth plurality of recesses about the circumference of the elongate member.

Figure 15C:
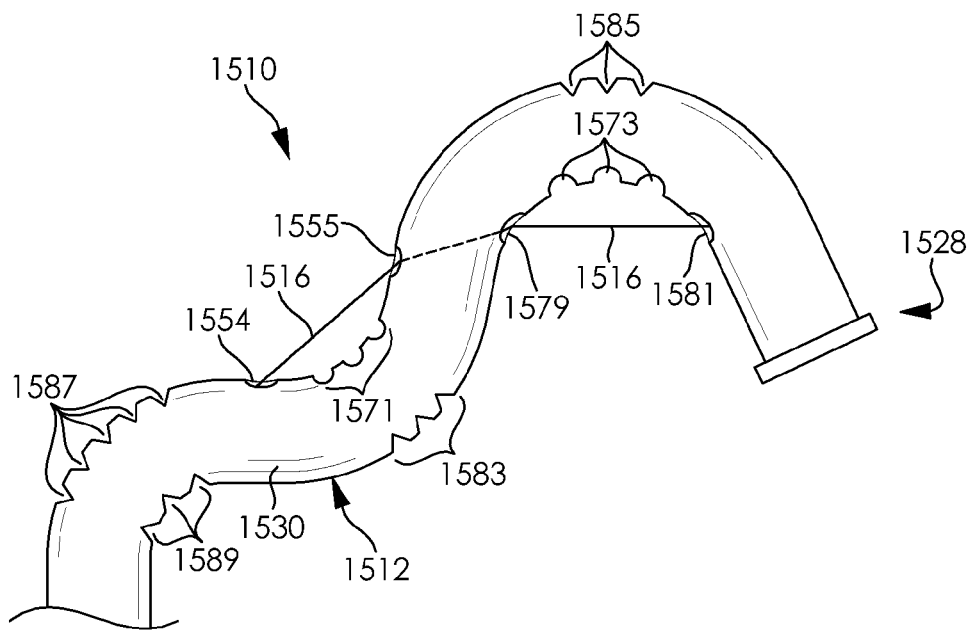
FIG. 15C is a partial side view of another exemplary medical device in a second configuration.

FIG. 15C illustrates the distal end of another exemplary medical device 1510. Medical device 1510 is similar to medical device 1310 illustrated in FIG. 15B, and described above, except as detailed below. Reference numbers in FIG. 15C refer to the same structural element or feature referenced by the same number in FIG. 15B, offset by 200. Thus, medical device 1510 comprises an elongate member 1512 and wire member 1516.

In the illustrated embodiment, elongate member body 1530 defines a fifth plurality of recesses 1587 and a sixth plurality of recesses 1589. The fifth plurality of recesses 1587 is disposed between elongate member proximal end (not shown) and elongate member first aperture 1554. When elongate member 1512 is in the straight, or substantially straight, configuration, each of the elongate member first aperture 1554, elongate member second aperture 1555, first plurality of recesses 1571, fourth plurality of recesses 1585, and the fifth plurality of recesses 1587 is disposed on the first elongate member longitudinal axis that is disposed parallel to the lengthwise axis of elongate member 1512. The sixth plurality of recesses 1589 is disposed between elongate member proximal end (not shown) and third plurality of recesses 1583. When elongate member 1512 is in the straight, or substantially straight, configuration, each of the third plurality of recesses 1583, elongate member third aperture 1579, second plurality of recesses 1573, elongate member fourth aperture 1581, and the sixth plurality of recesses 1589 is disposed on the second elongate member longitudinal axis that is disposed parallel to the lengthwise axis of elongate member 1512. Thus, the elongate member body 1530 defines a fifth relief between elongate member proximal end (not shown) and elongate member first aperture 1554 and a sixth relief between elongate member proximal end (not shown) and the third relief (e.g., third plurality of recesses 1573).

Elongate member first aperture 1554, elongate member second aperture 1555, and each recess of the fifth plurality of recesses 1587 are spaced longitudinally along the length of elongate member 1512. Elongate member third aperture 1579, elongate member fourth aperture 1581, and each recess of the sixth plurality of recesses 1589 are spaced longitudinally along the length of elongate member 1512. In the illustrated embodiment, each of the first longitudinal axis and second longitudinal axis is contained on a plane that passes through elongate member 1512 and contains the elongate member lengthwise axis. In addition, each feature disposed on the first elongate member longitudinal axis is disposed on a first side of elongate member 1512 that is opposably facing, or substantially opposably facing, a second side of elongate member 1512 on which each feature disposed on the second elongate member longitudinal axis is disposed. Optionally, elongate member 1512 can omit the inclusion of fifth plurality of recesses 1587 and/or sixth plurality of recesses 1589. The inclusion of a fifth plurality of recesses 1587 and sixth plurality of recesses 1589 disposed proximal to elongate member first aperture 1554 provides a mechanism for defining a curve along the length of elongate member 1512 proximal to elongate member first aperture 1554. In addition, this configuration allows for the proximal end to be arranged in a desired configuration prior to, or during the performance of a procedure (e.g., to reduce the discomfort during the performance of a procedure).

While a fifth plurality of recesses 1587 and a sixth plurality of recesses 1589 are illustrated as disposed proximal to elongate member first aperture 1554, any suitable number of recesses can be defined on an elongate member proximal to an aperture defined by the elongate member. Skilled artisans will be able to select a suitable number of recesses to define on an elongate member according to a particular embodiment based on various considerations, including the desired flexibility of an elongate member at a particular location. Example number of recesses considered suitable to define on an elongate member include, but are not limited to, one, at least one, two, a plurality, three, four, five, six, and any other number considered suitable for a particular application.

Figure 15D:
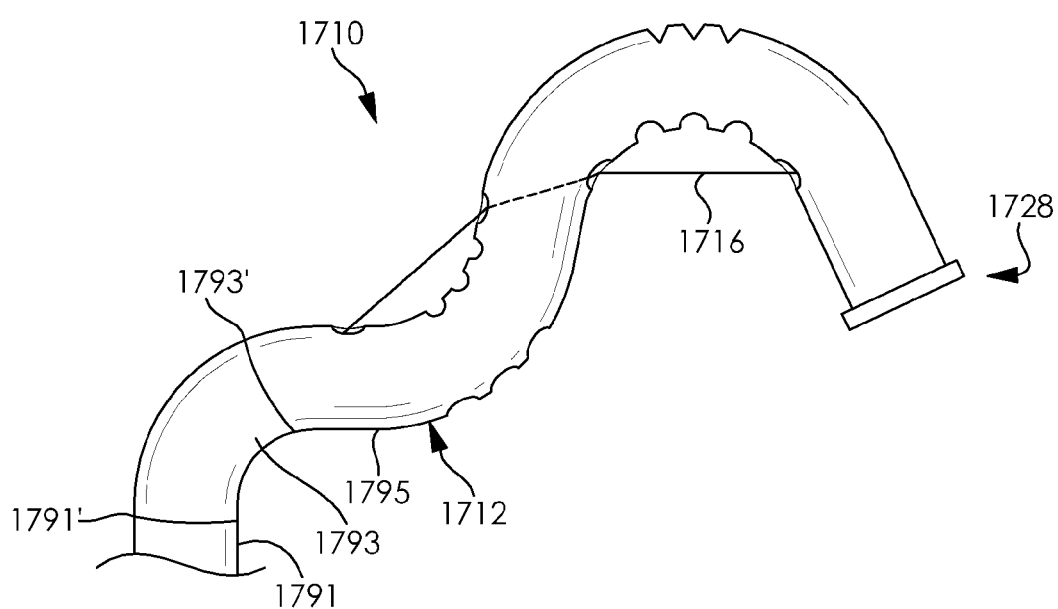
FIG. 15D is a partial side view of another exemplary medical device in a second configuration.

FIG. 15D illustrates the distal end of another exemplary medical device 1710. Medical device 1710 is similar to medical device 1510 illustrated in FIG. 15C, and described above, except as detailed below. Reference numbers in FIG. 15D refer to the same structural element or feature referenced by the same number in FIG. 15C, offset by 200. Thus, medical device 1710 comprises an elongate member 1712 and wire member 1716.

In the illustrated embodiment, alternative to including a fifth plurality of recesses (e.g., fifth plurality of recesses 1587) and a sixth plurality of recesses (e.g., sixth plurality of recesses 1589), elongate member 1712 has an elongate member first portion 1791, an elongate member second portion 1793, and an elongate member third portion 1795. Elongate member first portion 1791 extends from elongate member proximal end (not shown) to elongate member second portion 1793. Elongate member second portion 1793 extends from elongate member first portion 1791 toward elongate member elongate member distal end 1728 and comprises a relief. Elongate member third portion 1795 extends from elongate member second portion 1793 to elongate member distal end 1728.

Elongate member first portion 1791 is formed of a first material, elongate member second portion 1793 is formed of a second material, and elongate member third portion 1795 is formed of a third material. Each of the first material, second material, and/or third material can be identical or different from one another. In the illustrated embodiment, the first material and third material are the same and second material is different than the first material such that the second material is relatively more flexible, or substantially more flexible, than the first material and the third material is relatively more rigid, or substantially more rigid, than the second material.

In the illustrated embodiment, elongate member first portion 1791 abuts elongate member second portion 1793 at elongate member first junction 1791' and elongate member second portion 1793 abuts elongate member third portion 1795 at elongate member second junction 1793'. In the illustrated embodiment, each of elongate member first junction 1791' and elongate member second junction 1793' comprises an overlapping butt joint. While an overlapping butt joint is illustrated as the type of attachment between elongate member first portion 1791 and elongate member second portion 1793 and elongate member second portion 1793 and elongate member third portion 1795, any suitable method of attachment between an elongate member first portion, elongate member second portion, and/or an elongate member third portion can be used. Skilled artisans will be able to select a suitable method of attachment between an elongate member first portion, elongate member second portion, and/or an elongate member third portion according to a particular embodiment based on various considerations, including the type of the materials forming the elongate member first portion, elongate member second portion, and/or elongate member third portion. Example methods of attachment considered suitable between an elongate member first portion, an elongate member second portion, and/or an elongate member third portion include, but are not limited to, a butt joint, an overlapping butt joint (as illustrated in FIG. 15D), a threaded joint, an overlapped joint, and any other method of attachment considered suitable for a particular application. The use of an overlapping butt joint allows elongate member first portion, elongate member second portion, and elongate member third portion to be contiguous to one another. Alternatively, an elongate member can be a single component such that a first portion and second portion are integral with one another.

Elongate member first portion 1791, elongate member second portion 1793, and elongate member third portion 1795 can be formed of any suitable material and can be fabricated using any suitable method. Skilled artisans will be able to select suitable materials and methods of forming an elongate member first portion, an elongate member second portion, and an elongate member third portion according to a particular embodiment based on various considerations, including the desired flexibility of the elongate member. Example materials considered suitable to form an elongate member first portion, elongate member second portion, and/or an elongate member third portion include, but are not limited to, biocompatible materials, materials that can be made biocompatible, metals such as stainless steel, titanium, polymers, Pebax, nylon, polyethylene, polyurethane, silicone, coiled materials, and braided materials. Example methods of manufacture considered suitable to fabricate an elongate member first portion, elongate member second portion, and/or an elongate member third portion include, but are not limited to, extrusion processes, molding processes, and any other method considered suitable for a particular application.

While elongate member 1712 is illustrated as having an elongate member first portion 1791 formed of a first material, an elongate member second portion 1793 formed of a second material, and an elongate member third portion 1795 formed of a third material, an elongate member can have any suitable number of portions formed of any suitable number of materials, and skilled artisans will be able to select a suitable number of portions and materials to form an elongate member according to a particular embodiment based on various considerations, including the desired bodily passage within which a medical device is intended to be used. For example, alternative to an elongate member having an elongate member first portion formed of a first material, an elongate member second portion formed of a second material, and an elongate member third portion formed of a third material, an elongate member can be formed of the same material along its entire length, of different forms and/or compositions of the same material along its entire length, or a portion thereof, or formed of a plurality of different materials, each having a portion defined along the length of the elongate member. For example, an elongate member, or portion thereof (e.g., elongate member first portion, elongate member second portion, elongate member third portion), can be formed of a braided material to add torsional strength to the elongate member and/or formed of a coiled material to provide kink-resistance. Optionally, an elongate member, or portion thereof (e.g., elongate member first portion, elongate member second portion, elongate member third portion), can be formed of both a braided material and coiled material, to add torsional strength to the elongate member and to provide kink-resistance.

For example, an elongate member can be a single continuous component such that an elongate member first portion, elongate member second portion, and elongate member third portion are integral with one another (e.g., junction 1791' is omitted, junction 1793' is omitted) and elongate member is formed of a single continuous material along its length. The material forming the elongate member can have a hardness that changes from the elongate member proximal end to the elongate member distal end (e.g., durometer hardness). The hardness at the elongate member first portion can have a first quantity, the hardness at the elongate member second portion can have a second quantity that is different than the first quantity, and the hardness at the elongate member third portion can have a third quantity that is different, or the same as, the first quantity or second quantity such that the elongate member second portion and/or elongate member third portion is relatively more flexible than the elongate member first portion. Thus, the hardness at the elongate member first portion can be greater than the hardness at the elongate member second portion, or the elongate member third portion, to provide rigidity along the elongate member first portion and flexibility along the elongate member second portion, and/or elongate member third portion.

The inclusion of a relief (e.g., an elongate member second portion 1793) that is formed of a material that is relatively more flexible, or substantially more flexible, than an elongate member first portion 1791 and/or elongate member third portion 1795 provides a mechanism for defining a curve along the length of elongate member 1712 proximal to elongate member first aperture 1754. In addition, this configuration allows for the proximal end to be arranged in a desired configuration prior to, or during the performance of a procedure (e.g., to reduce the discomfort during the performance of a procedure).

While an elongate member first portion 1791, elongate member second portion 1793, and an elongate member third portion 1795 are illustrated as arranged in a particular configuration and as having particular properties, any arrangement of one or more portions of an elongate member having any suitable properties is considered suitable. Skilled artisans will be able to select a suitable arrangement for one or more portions of an elongate member and suitable properties for each portion of an elongate member according to a particular embodiment based on various considerations, including the desired flexibility of an elongate member at a particular location. For example, an elongate member first portion can be flexible relative to an elongate member third portion.

Furthermore, a relief that comprises a recess, or plurality of recesses, can be defined by an elongate member on an elongate member first portion, elongate member second portion, and/or elongate member third portion to increase the flexibility of the elongate member at a desired location. For example, a fifth plurality of recesses (e.g., fifth plurality of recesses 1587) and/or a sixth plurality of recesses (e.g., sixth plurality of recesses 1589) can be included on an elongate member second portion to increase the flexibility of elongate member at the elongate member second portion.

FIG. 15E illustrates another exemplary medical device 1910. Medical device 1910 is similar to medical device 910 illustrated in FIGS. 14, 14A, 14B, and 15, and described above, except as detailed below. Reference numbers in FIG. 15E refer to the same structural element or feature referenced by the same number in FIGS. 14, 14A, 14B, and 15, offset by 1000. Thus, medical device 1910 comprises an elongate member 1912, a handle 1914, and wire member 1916.

In the illustrated embodiment, medical device includes 1910 includes a second actuator 1962' and a second wire member 1916'. In addition, elongate member 1912 defines a second elongate member proximal opening 1940', third elongate member proximal opening 1940", second wire member opening 1952', second elongate member lumen 1936', and third elongate member lumen 1936". Second elongate member lumen 1936' extends from second elongate member proximal opening 1940' to wire member opening 1952. Third elongate member lumen 1936" extends from third elongate member proximal opening 1940" to second wire member opening 1952'.

In the illustrated embodiment, first wire member 1916 is attached to first actuator 1962 and second wire member 1916' is attached to second actuator 1962'. Second actuator 1962' is similar to first actuator 1962 and moveable within actuator opening 1980 between an actuator first position and an actuator second position, as described above with respect to actuator 62. Thus, handle 1914 comprises a first actuator 1962 and a second actuator 1962'.

Each of elongate member first aperture 1954 and elongate member second aperture 1955 extends through elongate member body 1930 and provides access to second elongate member lumen 1936'. Each of elongate member third aperture 1979 and elongate member fourth aperture 1981 extends through elongate member body 1930 and provides access to third elongate member lumen 1936".

In the illustrated embodiment, each of elongate member first aperture 1954 and elongate member second aperture 1955 is disposed on a first elongate member longitudinal axis 1975 that is parallel to elongate member lengthwise axis 1935. Each of elongate member third aperture 1979 and elongate member fourth aperture 1981 is disposed on a second elongate member longitudinal axis 1977 that is parallel to elongate member lengthwise axis 1935. Elongate member lengthwise axis 1935, first elongate member longitudinal axis 1975, and second elongate member longitudinal axis 1977 are each contained on a plane that passes through elongate member 1912. Thus, each feature disposed on the first elongate member longitudinal axis 1975 is disposed on a first side of elongate member 1912 that is opposably facing, or substantially opposably facing, a second side of elongate member 1912 on which each feature disposed on the second elongate member longitudinal axis 1977 is disposed.

Second actuator 1962' is moveable between an actuator first position, as shown in FIG. 15E, and an actuator second position (not shown). Movement of second actuator 1962' between the actuator first position and actuator second position results in movement of elongate member 1912 between a first straight, or substantially straight, configuration and a curved configuration, as described in more detail herein.

In the illustrated embodiment, first wire member 1916 has a wire member first end 2066 attached first actuator 1962 and a wire member second end 2068 attached within second elongate member lumen 1936' proximal to elongate member distal end 1928. First wire member 1916 extends from first actuator 1962 within second elongate member lumen 1936' to elongate member first aperture 1954, passes through elongate member first aperture 1954 to the exterior of elongate member 1912, extends from elongate member first aperture 1954 to elongate member second aperture 1955 along the exterior of elongate member 1912, passes through elongate member second aperture 1955 and into second elongate member lumen 1936', and is attached to elongate member 1912 proximal to elongate member distal end 1928. Thus, the first wire member 1916 extends along a first portion of the interior surface of the elongate member 1912, passes through the elongate member body 1930 a plurality of times (e.g., at elongate member first aperture 1954, elongate member second aperture 1955), extends along a first portion of the exterior surface of the elongate member 1912, and extends along a second portion of the interior surface of the elongate member 1912. The second portion of the interior surface is different than the first portion of the interior surface and is disposed distal to the first portion of the interior surface.

Second wire member 1916' has a wire member first end 2066' attached to second actuator 1962' and a wire member second end 2068' attached to elongate member 1912 within third elongate member lumen 1936" proximal to elongate member distal end 1928. Second wire member 1916' extends from second actuator 1962' within third elongate member lumen 1936" to elongate member third aperture 1979, passes through elongate member third aperture 1979 to the exterior of elongate member 1912, extends from elongate member third aperture 1979 to elongate member fourth aperture 1981 along the exterior of elongate member 1912, passes through elongate member fourth aperture 1981 and into third elongate member lumen 1936", and is attached to elongate member 1912 proximal to elongate member distal end 1928. Thus, each wire member is disposed in a separate lumen defined by elongate member 1912. Thus, the second wire member 1916' extends along a third portion of the interior surface of the elongate member 1912, passes through the elongate member body 1930 a plurality of times (e.g., at elongate member third aperture 1979, elongate member fourth aperture 1981), extends along a second portion of the exterior surface of the elongate member 1912, and extends along a fourth portion of the interior surface of the elongate member 1912. The fourth portion of the interior surface is different than the third portion of the interior surface and is disposed distal to the third portion of the interior surface. The third portion of the interior surface has a length that is greater than the first portion of the interior surface. The second portion of the exterior surface is disposed distal to the first portion of the exterior surface.

This configuration omits the inclusion of a wire member within first elongate member lumen 1936 and allows for a first curve to be defined when first actuator 1926 is moved between the actuator first position and the actuator second position and a second curve to be defined when second actuator 1926' is moved between the actuator first position and the actuator second position. Thus, a first curve can be defined independent of a second curve.

While first wire member 1916 and second wire member 1916' have been illustrated as attached to elongate member proximal to elongate member distal end 1928, a wire member can be attached to an elongate member at any suitable location, such as within a wire member opening defined by an elongate member. For example, a first wire member second end (e.g., first wire member second end 2068) can be attached within, or passed through, a wire member opening (e.g., wire member opening 1952) and a second wire member second end (e.g., second wire member second end 2068') can be attached within, or passed through, a second wire member opening (e.g., second wire member opening 1952').

Alternative to medical device including a second actuator 1926' and second wire member 1916' and elongate member defining a third elongate member lumen 1936", a medical device can include a single wire member that passes through a second elongate member lumen defined by an elongate member body.

Figure 15G:
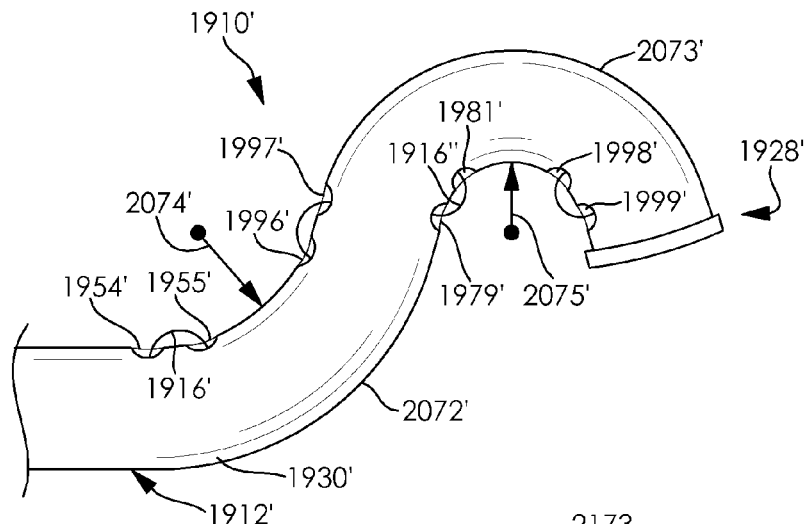
FIG. 15G is a partial side view of the medical device illustrated in FIG. 15F in a second configuration.

FIGS. 15F and 15G illustrate the distal end of another exemplary medical device 1910'. Medical device 1910' is similar to medical device 1910 illustrated in FIG. 15E, and described above, except as detailed below. Reference numbers in FIGS. 15F and 15G refer to the same structural element or feature referenced by the same number in FIG. 15E, offset by '. Thus, medical device 1910' comprises an elongate member 1912', a first wire member 1916' and a second wire member 1916".

In the illustrated embodiment, elongate member body 1930' defines an elongate member fifth aperture 1996', elongate member sixth aperture 1997', elongate member seventh aperture 1998', and an elongate member eighth aperture 1999'. Elongate member fifth aperture 1996' is disposed between elongate member second aperture 1955' and elongate member distal end 1928'. Elongate member sixth aperture 1997' is disposed between elongate member fifth aperture 1996' and elongate member distal end 1928'. Elongate member seventh aperture 1998' is disposed between elongate member fourth aperture 1981' and elongate member distal end 1928'. Elongate member eighth aperture 1999' is disposed between elongate member seventh aperture 1998' and elongate member distal end 1928'. Each of elongate member fifth aperture 1996', elongate member sixth aperture 1997', elongate member seventh aperture 1998', and elongate member eighth aperture 1999' is spaced longitudinally along the length of elongate member 1912'. Each of elongate member fifth aperture 1996' and elongate member sixth aperture 1997' extends through elongate member body 1930' and provides access to second elongate member lumen 1936" and is adapted to receive a portion of first wire member 1916'. Each of elongate member seventh aperture 1998' and elongate member eighth aperture 1999' extends through elongate member body 1930' and provides access to third elongate member lumen 1936"' and is adapted to receive a portion of second wire member 1916".

First wire member 1916' extends from first actuator (not shown) within second elongate member lumen 1936" to elongate member first aperture 1954', passes through elongate member first aperture 1954' and along the exterior of elongate member 1912' to elongate member second aperture 1955', passes through elongate member second aperture 1955' and into second elongate member lumen 1936" to elongate member fifth aperture 1996', passes through elongate member fifth aperture 1996' and along the exterior of elongate member 1912' to elongate member sixth aperture 1997', passes through elongate member sixth aperture 1997' and into second elongate member lumen 1936" and is attached to elongate member 1912' proximal to elongate member distal end 1928'. Thus, the first wire member 1916' extends along a first portion of the interior surface of the elongate member 1912', passes through the elongate member body 1930' a plurality of times (e.g., at elongate member first aperture 1954', elongate member second aperture 1955', elongate member fifth aperture 1996', elongate member sixth aperture 1997'), extends along a first portion of the exterior surface of the elongate member 1912', extends along a second portion of the interior surface of the elongate member 1912', extends along a second portion of the exterior surface of the elongate member 1912', and extends along a third portion of the interior surface of the elongate member 1912'. The third portion of the interior surface is different than the second portion and the first portion of the interior surface and is disposed distal to the second portion and the first portion of the interior surface. The second portion of the exterior surface is disposed distal to the first portion of the exterior surface.

Second wire member 1916" extends from second actuator (not shown) to elongate member third aperture 1979', passes through elongate member third aperture 1979' and along the exterior of elongate member 1912' to elongate member fourth aperture 1981', passes through elongate member fourth aperture 1981' and into third elongate member lumen 1936"' to elongate member seventh aperture 1998', passes through elongate member seventh aperture 1998' along the exterior of elongate member 1912' to elongate member eighth aperture 1999', passes through elongate member eighth aperture 1999' and is attached to elongate member 1912' proximal to elongate member distal end 1928'. Thus, the second wire member 1916" extends along a fourth portion of the interior surface of the elongate member 1912', passes through the elongate member body 1930' a plurality of times (e.g., at elongate member third aperture 1979', elongate member fourth aperture 1981', elongate member seventh aperture 1998', elongate member eighth aperture 1999'), extends along a third portion of the exterior surface of the elongate member 1912', extends along a fifth portion of the interior surface of the elongate member 1912', extends along a fourth portion of the exterior surface of the elongate member 1912', and extends along a sixth portion of the interior surface of the elongate member 1912'. The sixth portion of the interior surface is different than the fifth portion and the fourth portion of the interior surface and is disposed distal to the fifth portion and the fourth portion of the interior surface. Each of the fifth portion and sixth portion of the interior surface is disposed distal to the third portion of the interior surface. The fourth portion of the exterior surface is disposed distal to the third portion of the exterior surface and distal to the second portion of the exterior surface.

In the illustrated embodiment, each of elongate member first aperture 1954', elongate member second aperture 1955', elongate member fifth aperture 1996', and elongate member sixth aperture 1997' is disposed on the first elongate member longitudinal axis 1975' that is parallel to elongate member lengthwise axis 1935'. Each of elongate member third aperture 1979', elongate member fourth aperture 1981', elongate member seventh aperture 1998', and elongate member eighth aperture 1999' is disposed on the second elongate member longitudinal axis 1977' that is parallel to elongate member lengthwise axis 1935'. The first elongate member longitudinal axis 1975' is different than second elongate member longitudinal axis 1977' and elongate member lengthwise axis 1935'. Each of the elongate member lengthwise axis 1935', first elongate member longitudinal axis 1975', and second elongate member longitudinal axis 1977' is contained on a plane that passes through elongate member 1912'. In the illustrated embodiment, each feature disposed on the first elongate member longitudinal axis 1975' is disposed on a first side of elongate member 1912' that is opposably facing, or substantially opposably facing, a second side of elongate member 1912' on which each feature disposed on the second elongate member longitudinal axis 1977' is disposed.

While fifth elongate member aperture 1996' and sixth elongate member aperture 1997' are illustrated as disposed on first longitudinal axis 1975' and seventh elongate member aperture 1998' and eighth elongate member aperture 1999' are illustrated as disposed on second longitudinal axis 1977', a fifth elongate member aperture, sixth elongate member aperture, seventh elongate member aperture, and/or eighth elongate member aperture can be disposed on any suitable longitudinal axis and positioned at any suitable location on an elongate member. Skilled artisans will be able to select a suitable longitudinal axis to position an aperture defined on an elongate member and a suitable position to locate an aperture according to a particular embodiment based on various considerations, including the desired structural configuration of a curve defined on an elongate member. For example, an elongate member aperture can be positioned on a third elongate member longitudinal axis that does not contain the first elongate member aperture, second elongate member aperture, third elongate member aperture, and/or fourth elongate member aperture. The third elongate member longitudinal axis can be disposed parallel to the elongate member lengthwise axis and on a third plane that is disposed at an angle, or that is coplanar with, a first plane that contains a first elongate member longitudinal axis and a first elongate member aperture. Example angles considered suitable to position a first plane relative to a third plane include, but are not limited to, orthogonal, a 45 degree angle, an angle between about 1 degree to about 90 degrees, an angle between about 90 degrees to about 180 degrees, an angle between about 180 degrees to about 270 degrees, and angle between about 270 degrees to about 360 degrees, and any other angle considered suitable for a particular application. Thus, a first elongate member aperture and/or second elongate member aperture can be disposed linearly, or offset, from a fifth elongate member aperture, sixth elongate member aperture, seventh elongate member aperture, and/or eighth elongate member aperture about the circumference of the elongate member. Alternatively, the fifth elongate member aperture can be disposed on a longitudinal axis that is different than a longitudinal axis that contains the sixth elongate member aperture or the seventh elongate member aperture can be disposed on a longitudinal axis that is different than a longitudinal axis that contains the eighth elongate member aperture.

In use, as described herein, movement of each of the first actuator (not shown) and second actuator (not shown) away from elongate member distal end 1928' from the actuator first position to the actuator second position results in movement of first wire member 1916' and second wire member 1916" such that elongate member 1912' moves from a straight, or substantially straight, configuration to a curved configuration, as shown in FIG. 15G. In the curved configuration, elongate member 1912' defines a first curve 2072' at a first radius of curvature 2074' and a second curve 2073' at a second radius of curvature 2075'. Movement of each of first actuator (not shown) and second actuator (not shown) towards elongate member distal end 1928' results in elongate member 1912' returning to its straight, or substantially straight, configuration. Thus, when each of the first actuator (not shown) and second actuator (not shown) is in the actuator first position, elongate member 1912' is in the straight, or substantially straight, configuration and when each of first actuator (not shown) and second actuator (not shown) is in the actuator second position, elongate member 1912' is in the curved configuration. This configuration provides a mechanism for defining more than one curve along the length of elongate member 1912' such that elongate member distal end 1928' can be positioned in a variety of different locations. In addition, this configuration provides a mechanism for increasing a radius of curvature defined by an elongate member when in the second configuration.

Figure 16:
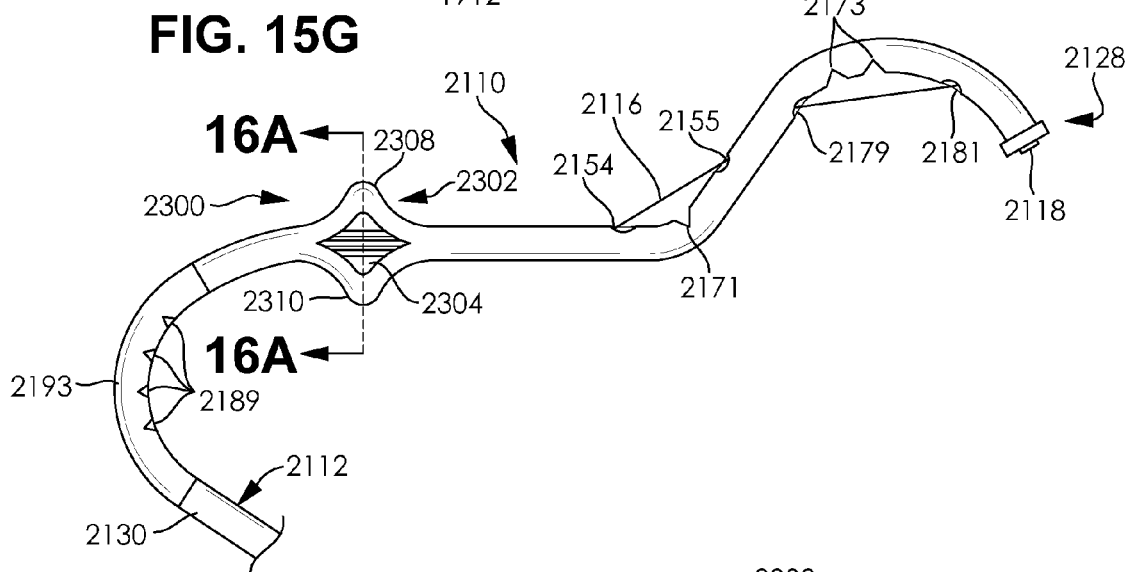
FIG. 16 is a partial side view of another exemplary medical device in a second configuration.
Figure 16A:
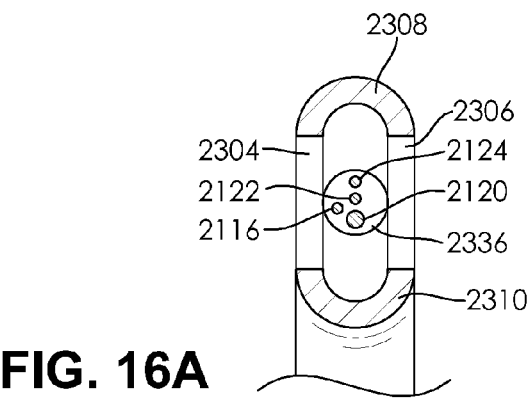
FIG. 16A is a sectional view of the medical device illustrated in FIG. 16, taken along line 16A-16A.

FIGS. 16 and 16A illustrate the distal end of another exemplary medical device 2110. Medical device 2110 is similar to medical device 1710 illustrated in FIG. 15D, and described above, except as detailed below. Reference numbers in FIGS. 16 and 16A refer to the same structural element or feature referenced by the same number in FIG. 15D, offset by 400. Thus, medical device 2110 comprises an elongate member 2112 and a wire member 2116. In the illustrated embodiment, the imaging device 2118, data transfer cable 2120, first optical fiber 2122, second optical fiber 2124 are illustrated for clarity.

In the illustrated embodiment, elongate member 2112 includes an anchoring member 2300 and defines a recess 2171 between elongate member first aperture 2154 and elongate member second aperture 2155, a plurality of recesses 2173 between elongate member third aperture 2179 and elongate member fourth aperture 2181, and a plurality of recesses 2189 on second portion of elongate member 2193. Thus, elongate member 2112 has a relief between elongate member first aperture 2154 and elongate member second aperture 2155, a plurality of reliefs between elongate member third aperture 2179 and elongate member fourth aperture 2181, and a plurality of reliefs 2189 on second portion of elongate member 2193. In addition, elongate member 2112 omits the inclusion of a third plurality of recesses (e.g., third plurality of recesses 1583) and a fourth plurality of recesses (e.g., fourth plurality of recesses 1585).

An anchoring member 2300 can comprise any suitable structural arrangement capable of fixedly attaching, releasably attaching, fixing, and/or centering an elongate member within a bodily passage. Skilled artisans will be able to select a suitable structural arrangement for an anchoring member according to a particular embodiment based on various considerations, including the material that forms an elongate member. Example structural arrangements considered suitable for an anchoring member include, but are not limited to, one or more curves defined by an elongate member (e.g., curve 172, curve 1072, curve 1073), malecot structures, one or more wire members, one or more balloons (e.g., inflatable balloons), one or more projections, and any other structural arrangement considered suitable for a particular application.

In the illustrated embodiment, anchoring member 2300 comprises a malecot structure 2302. Elongate member body 2130 defines a first opening 2304, a second opening 2306, a first wing member 2308, and a second wing member 2310 between the second portion of elongate member 2193 and elongate member first aperture 2154. Each of the first opening 2304 and second opening 2306 extends through elongate member body 2130 and provides access to elongate member lumen 2336. First opening 2304 is defined on a first side of elongate member 2112 that is opposably facing, or substantially opposably facing, a second side of elongate member 2112 on which second opening 2306 is defined. Malecot structure 2302 is adapted to move between a first configuration and a second configuration. In the first configuration, each of the first wing member 2308 and second wing member 2310 is disposed a first distance from the elongate member lengthwise axis and in the second configuration each of the first wing member 2308 and second wing member 2310 is disposed a second distance from elongate member lengthwise axis that is less than the first distance. Each of the first wing member 2308 and second wing member 2310 is biased to the first configuration. The inclusion of a malecot structure 2302 as anchoring member 2300 provides a mechanism for anchoring elongate member 2112 within a bodily passage such that it is fixedly, or releasably, attached and/or centered within the bodily passage.

Biasing a wing member can be accomplished using any suitable method and or structure, and skilled artisans will be able to select a suitable method and/or structure to bias a wing member according to a particular embodiment based on various considerations, including the structural arrangement of the wing member, the structural arrangement of an elongate member, and/or the material forming the elongate member. Example methods of biasing a wing member considered suitable include, but are not limited to, manufacturing an anchoring member in the first configuration, heat-treating the material forming an anchoring member, and any other method considered suitable for a particular application.

While a first opening 2304, second opening 2306, first wing member 2308, and second wing member 2310 are illustrated, any suitable number of openings and/or wing members can be defined on an elongate member. Skilled artisans will be able to select a suitable number of openings and/or wing members to define on an elongate member according to a particular embodiment based on various considerations, including the structural arrangement of the bodily passage within which a medical device is intended to be disposed. Example number of openings considered suitable to define on an elongate member include, but are not limited to, one, at least one, two, a plurality, three, four, five, and any other number considered suitable for a particular application. Example number of wing members considered suitable to include on an elongate member include, but are not limited to, one, at least one, two, a plurality, three, four, five, and any other number considered suitable for a particular application.

While only a single anchoring member is illustrated as disposed between an elongate member proximal end and an elongate member first aperture, a medical device can include any suitable number of anchoring members disposed at any suitable location along the length of an elongate member. Skilled artisans will be able to select a suitable number of anchoring members to include on an elongate member and a suitable location to position an anchoring member according to a particular embodiment based on various considerations, including the structural arrangement of the bodily passage within which a medical device is intended to be disposed. Example number of anchoring members considered suitable to include on an elongate member include, but are not limited to, one, at least one, two, a plurality, three, four, five, and any other number considered suitable for a particular application. Example locations considered suitable to position one or more anchoring members include, but are not limited to, between an elongate member proximal end and an elongate member distal end, between a second portion of an elongate member and an elongate member first aperture, between an elongate member second aperture and an elongate member third aperture, between an elongate member sixth aperture and an elongate member third aperture, between an elongate member eighth aperture and an elongate member distal end, and any other location considered suitable for a particular application.

Figure 16B:
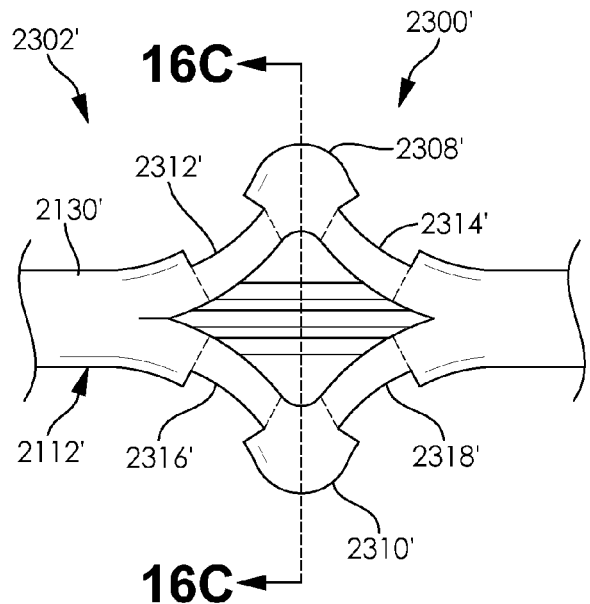
FIG. 16B is a partial side view of a medical device that has a first alternative anchoring member.
Figure 16C:
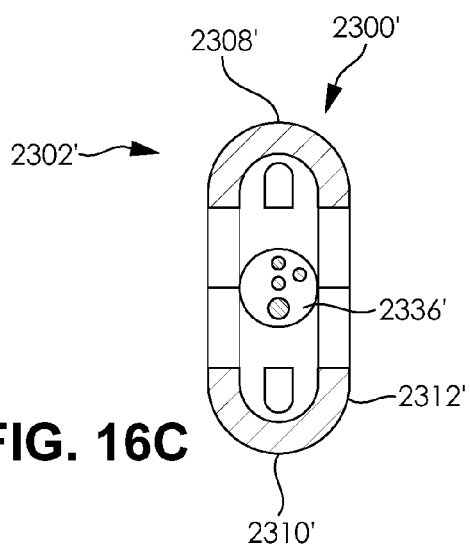
FIG. 16C is a sectional view of the medical device illustrated in FIG. 16B taken along line 16C-16C.

FIGS. 16B and 16C illustrate a first alternative anchoring member 2300'. In the illustrated embodiment, the first alternative anchoring member 2300' is an alternative malecot structure 2302' defined along the length of elongate member 2112'. Malecot structure 2302' is similar to malecot structure 2302 illustrated in FIGS. 16 and 16A, and described above, except as detailed below. Reference numbers in FIGS. 16B and 16C refer to the same structural element or feature referenced by the same number in FIGS. 16A and 16B, offset by '.

In the illustrated embodiment, elongate member body 2130' defines a first opening 2312' and a second opening 2314' on first wing member 2308' and a first opening 2316' and second opening 2318' on second wing member 2310'. Each of the first opening 2312' and second opening 2314' defined on first wing member 2308' and first opening 2316' and second opening 2318' defined on the second wing member 2310' extends through elongate member body 2330' and provides access to elongate member lumen 2336'. This configuration reduces the force necessary to move each of the first wing member 2308' and second wing member 2310' from the first configuration to the second configuration as compared to an anchoring member that does not include openings defined on a wing member. This configuration also provides a mechanism for fluid (e.g., air) to pass through the anchoring member during the performance of a procedure, which prevents, or substantially prevents, obstructing a bodily passage during the procedure.

While only a first opening 2312' and second opening 2314' are illustrated as being defined on first wing member 2308' and a first opening 2316' and second opening 2318' are illustrated as being defined on second wing member 2310', any suitable number of openings can be defined on a wing member. Skilled artisans will be able to select a suitable number of openings to define on a wing member according to a particular embodiment based on various considerations, including the desired flexibility of the wing member. Example number of openings considered suitable to define on a wing member include, but are not limited to, one, at least one, two, a plurality, three, four, five, and any other number considered suitable for a particular application.

Figure 17:
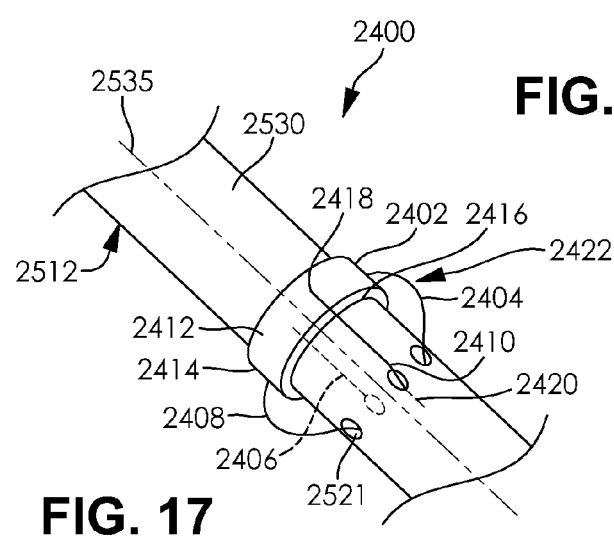
FIG. 17 is a partial side view of a medical device that has a second alternative anchoring member.

FIG. 17 illustrates a second alternative anchoring member 2400 disposed on an elongate member 2512. Elongate member 2512 is similar to elongate member 1712 illustrated in FIG. 15D, and described above, except as detailed below. With respect to elongate member 2512, reference numbers in FIG. 17 refer to the same structural element or feature referenced by the same number in FIG. 15D, offset by 800.

In the illustrated embodiment anchoring member 2400 comprises a band 2402, first wire member 2404, second wire member 2406, third wire member 2408, and fourth wire member 2410. Band 2402 is attached to elongate member 2512 and comprises a band body 2412 that defines a band outside diameter 2414 and a band inside diameter 2416. Band inside diameter 2416 is less than, equal to, or substantially equal to, the outside diameter of elongate member 2512. This provides a mechanism for attaching band 2402 to elongate member 2512.

Band 2402 can be attached to elongate member 2512 using any suitable method of attachment, and skilled artisans will be able to select a suitable method of attachment between a band and an elongate member according to a particular embodiment based on various considerations, including the material forming an elongate member. Example methods of attachment considered suitable between a band and an elongate member include, but are not limited to, using an adhesive, welding, and any other method of attachment considered suitable for a particular application. Alternatively, a band can be integral with an elongate member such that elongate member body defines band extending outward and away from an elongate member lengthwise axis.

Each of the first wire member 2404, second wire member 2406, third wire member 2408, and fourth wire member 2410 can be formed of any suitable material and can be attached to a band using any suitable method of attachment. Skilled artisans will be able to select a suitable material to form a wire member and a suitable method to attach a wire member to a band and/or an elongate member, according to a particular embodiment based on various considerations, including the material forming an elongate member. Example materials considered suitable to form a wire member include, but are not limited to, biocompatible materials, materials that can be made biocompatible, metals such as stainless steel, titanium, nickel-titanium alloy (e.g., Nitinol), coiled materials, braided materials, the material that form an elongate member, and any other material considered suitable for a particular application. Example methods of attachment considered suitable between a wire member and band and/or elongate member include, but are not limited to, using an adhesive, welding, and any other method of attachment considered suitable for a particular application. Alternatively, a wire member can be integral with an elongate member such that an elongate member body defines a wire member extending outward and away from an elongate member lengthwise axis.

In the illustrated embodiment, first wire member 2404 is disposed opposite, or substantially opposite, third wire member 2408 across elongate member lengthwise axis 2535 and second wire member 2406 is disposed opposite, or substantially opposite, fourth wire member 2410 across elongate member lengthwise axis 2535. Each of the first wire member 2404, second wire member 2406, third wire member 2408, and fourth wire member 2410 extends from a wire member first end 2418 attached to band 2402 outward and away from elongate member 2512 and towards elongate member distal end (not shown) to a wire member second end 2420 and defines a wire member bend 2422. Wire member bend 2422 is disposed between wire member first end 2418 and wire member second end 2420. Wire member first end 2418 is disposed a first distance from elongate member lengthwise axis 2535 and wire member second end 2420 is disposed a second distance from elongate member lengthwise axis 2535 that is less than the first distance. Elongate member 2512 defines a plurality of openings 2521 that extend into elongate member body 2530. The second end 2420 of a wire member is disposed through an opening of the plurality of openings 2521 such that each wire member can move between a first configuration and a second configuration. In the first configuration, the apex of each wire member is disposed a first distance from elongate member lengthwise axis 2535 and in the second configuration the apex of each wire member is disposed a second distance from elongate member lengthwise axis 2535 that is less than the first distance. Thus, each wire member is compressible along its length. The inclusion of an anchoring member 2400 on an elongate member provides a mechanism for anchoring elongate member 2512 within a bodily passage such that it is fixedly, or releasably, attached and/or centered within the bodily passage.

While a first wire member 2404, second wire member 2406, third wire member 2408, and fourth wire member 2410 are illustrated, any suitable number of wire members can be included in a medical device. Skilled artisans will be able to select a suitable number of wire members to include on a medical device according to a particular embodiment based on various considerations, including the desired flexibility of the elongate member at an anchoring member. Example number of wire members considered suitable to include on a medical device include, but are not limited to, one, at least one, two, a plurality, three, four, five, six, seven, eight, and any other number considered suitable for a particular application.

While first wire member 2404 is illustrated as disposed opposite, or substantially opposite, third wire member 2408 across elongate member lengthwise axis 2535 and second wire member 2406 is illustrated as disposed opposite, or substantially opposite, fourth wire member 2410 across elongate member lengthwise axis 2535, wire members included on a medical device can have any suitable structural arrangement. Skilled artisans will be able to select a suitable structural arrangement for one or more wire members included on a medical device according to a particular embodiment based on various considerations, including the desired flexibility of an anchoring member. Example configurations for a plurality of wire members include, but are not limited to, a first wire member being disposed adjacent a second wire member and a third wire member being disposed adjacent the second wire member and a fourth wire member about the lengthwise axis of an elongate member, such that a first wire member is disposed on a first plane that contains the lengthwise axis of an elongate member and a second wire member is disposed on a second plane that contains the lengthwise axis of an elongate member, the first plane being disposed at any suitable angle to the second plane, and any other configuration considered suitable for a particular application.

While each of the first wire member 2404, second wire member 2406, third wire member 2408, and fourth wire member 2410 are illustrated defining a bend 2422, a wire member can define any suitable number of bends along its length. Skilled artisans will be able to select a suitable number of bends to define on a wire member according to a particular embodiment based on various considerations, including the desired flexibility of the wire member. Example number of bends considered suitable to define on a wire member include, but are not limited to, one, at least one, two, a plurality, three, four, five, six, seven, eight, and any other number considered suitable for a particular application.

Figure 17A:
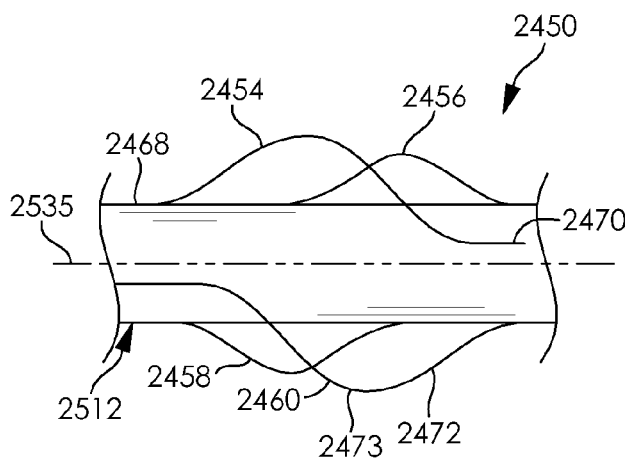
FIG. 17A is a partial side view of a medical device that has a third alternative anchoring member.

FIG. 17A illustrates a third alternative anchoring member 2450 disposed on an elongate member 2512. Elongate member 2512 is similar to elongate member 1712 illustrated in FIG. 15D, and described above, except as detailed below. With respect to elongate member 2512, reference numbers in FIG. 17A refer to the same structural element or feature referenced by the same number in FIG. 15D, offset by 800. Anchoring member 2450 is similar to anchoring member 2400 illustrated in FIG. 17, and described above, except as detailed below. With respect to anchoring member 2450, reference numbers in FIG. 17A refer to the same structural element or feature referenced by the same number in FIG. 17, offset by 50.

In the illustrated embodiment, anchoring member 2450 omits the inclusion of a band (e.g., band 2402) and comprises a first wire member 2454, second wire member 2456, third wire member 2458, and fourth wire member 2460. Each of the first wire member 2454, second wire member 2456, third wire member 2458, and fourth wire member 2460 extends from a wire member first end 2468 attached to elongate member 2512 to a wire member second end 2470 attached to elongate member 2512. Each wire member defines a bend 2472 having an apex 2473 disposed between wire member first end 2468 and wire member second end 2470.

Wire member first end 2468 is disposed a first distance from elongate member lengthwise axis 2535, wire member second end 2470 is disposed a second distance from elongate member lengthwise axis 2535, and apex 2473 is disposed a third distance from elongate member lengthwise axis 2535. In the illustrated embodiment, the first distance and second distance are equal, or substantially equal, and the third distance is greater than the first distance and the second distance. For each wire member, wire member first end 2468 is disposed on a first plane that contains elongate member lengthwise axis 2535 and wire member second end 2473 is disposed on a second plane that contains elongate member lengthwise axis 2535. The second plane is disposed orthogonal, or substantially orthogonal, to the first plane. Thus, for each wire member, wire member first end 2468 is offset from wire member second end 2470 about a quarter of the circumference of elongate member 2512.

Each of the first wire member 2454, second wire member 2456, third wire member 2458, and fourth wire member 2460 can be attached to elongate member 2512 using any suitable method of attachment. Skilled artisans will be able to select a suitable method to attach a wire member to an elongate member according to a particular embodiment based on various considerations, including the material that forms an elongate member. Example methods of attachment considered suitable between a wire member and an elongate member include, but are not limited to, using an adhesive, welding, and any other method of attachment considered suitable for a particular application. Optionally, a wire member can be integral with and/or formed of the same material as an elongate member such that an elongate member body defines a wire member that extends from a first end outward and away from an elongate member lengthwise axis and towards the elongate member lengthwise axis to a wire member second end.

Optionally, an elongate member can define a first opening through which a wire member first end is passed and/or a second opening through which a wire member second end is passed such that wire member first end and/or wire member second end can be attached within a lumen defined by elongate member or to the wall of an elongate member. If a wire member is disposed in a lumen defined by an elongate member, wire member can be moveable within the lumen such that it has a first configuration in which wire member second end is disposed within the lumen defined by elongate member and at a first distance from the lengthwise axis of the elongate member and a second configuration in which wire member second end is disposed outside of the lumen defined by the elongate member and a second distance from the elongate member lengthwise axis. Thus, a wire member can be advanced distally and out of a lumen defined by an elongate member to fixedly, or releasably, attach and/or center an elongate member within a bodily passage.

Figure 17B:
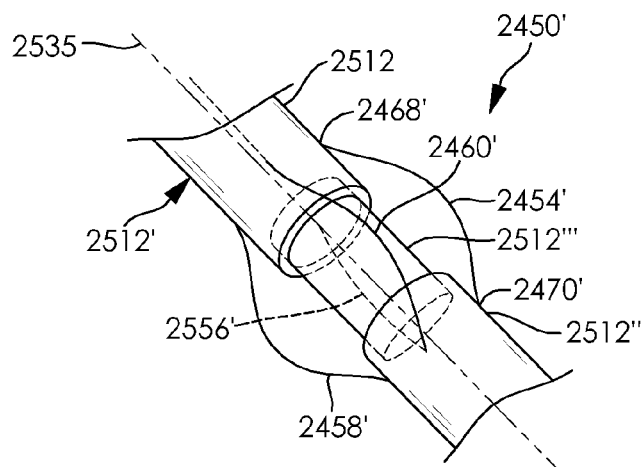
FIG. 17B is a partial side view of a medical device that has a fourth alternative anchoring member.

FIG. 17B illustrates a fourth alternative anchoring member 2450' disposed on an elongate member 2512. Elongate member 2512 is similar to elongate member 1712 illustrated in FIG. 15D, and described above, except as detailed below. With respect to elongate member 2512, reference numbers in FIG. 17B refer to the same structural element or feature referenced by the same number in FIG. 15D, offset by 800. Anchoring member 2450' is similar to anchoring member 2450 illustrated in FIG. 17A, and described above, except as detailed below. With respect to anchoring member 2450', reference numbers in FIG. 17B refer to the same structural element or feature referenced by the same number in FIG. 17A, offset by '.

In the illustrated embodiment, elongate member 2512 has an elongate member first portion 2512', an elongate member second portion 2512" separated from elongate member first portion 2512', and an elongate member third portion 2512" disposed within elongate member first portion 2512' and elongate member second portion 2512". Elongate member first portion 2512' is disposed proximal to elongate member second portion 2512" and is attached to elongate member second portion 2512" by first wire member 2454', second wire member 2456', third wire member 2458', and fourth wire member 2460'. Each of the elongate member first portion 2512' and wire member second portion 2512" is moveable along the length of wire member third portion 2512".

In the illustrated embodiment, the wire member first end 2468' and wire member second end 2470' of each wire member is disposed on a plane that contains elongate member lengthwise axis 2535. Each of the first wire member 2454', second wire member 2456', third wire member 2458', and fourth wire member 2460' can be biased to this configuration such that when no force is applied to elongate member 2512 or a wire member, each of the wire member first end 2468' and wire member second end 2470' is disposed on a first plane that contains elongate member lengthwise axis 2535.

Alternative to including an anchoring member, such as anchoring member 2300, anchoring member 2300', anchoring member 2400, anchoring member 2450, and/or anchoring member 2450', an elongate member can include an anchoring member comprising a balloon that is attached to the elongate member and moveable between a first deflated, or substantially deflated configuration, and a second inflated, or substantially inflated configuration. An elongate member can define a lumen in fluid communication with a chamber defined by the balloon such that a fluid can be introduced into the chamber of the balloon and withdrawn from the chamber of the balloon with the application of pressure. As fluid is introduced into the chamber of the balloon it moves from its first deflated, or substantially deflated, configuration to its inflated, or substantially inflated configuration. When the balloon is in its inflated, or substantially inflated configuration, the elongate member can be anchored within a bodily passage such that it is fixedly, or releasably, attached and/or centered within the bodily passage. Optionally, more than one balloon can be attached along the length of an elongate member and each balloon can define a chamber in fluid communication with a first lumen or with separate lumens.

Alternative to including an anchoring member, such as anchoring member 2300, anchoring member 2300', anchoring member 2400, anchoring member 2450, and/or anchoring member 2450', an anchoring member can comprise a plurality of bends defined along the length of an elongate member. The body of elongate member can define each bend such that it is biased to a first curved configuration and is moveable to a second configuration in which the bend is adapted to form to the structural configuration of a bodily passage. Alternative to the body of an elongate member defining each bend, a bend can be formed using the methods and structural arrangements described herein. For example, an elongate member body can define a first elongate member aperture and a second elongate member aperture on a first longitudinal axis, a third elongate member aperture and a fourth elongate member aperture on a second longitudinal axis, and a fifth elongate member aperture and a sixth elongate member aperture on a third longitudinal axis. Each aperture defined by the body of the elongate member being separated from another aperture defined by the body of the elongate member by a distance along the length of the elongate member. Each of the first longitudinal axis, second longitudinal axis, and third longitudinal axis is parallel to the lengthwise axis of the elongate member. The first longitudinal axis and third longitudinal axis can be coaxial and the second longitudinal axis can be disposed on a side that is opposably facing, or substantially opposable facing, the first longitudinal axis. In this configuration, when an actuator is moved to its second position elongate member defines multiple bends along its length that can be used to anchor the elongate member within a bodily passage such that it is fixedly, or releasably, attached and/or centered within the bodily passage.

Any suitable number of anchoring members can be included on an elongate member and disposed at any suitable location on an elongate member, and skilled artisans will be able to select a suitable number of anchoring members and a suitable location to position each anchoring member according to a particular embodiment based on various considerations, including the structural arrangement of a bodily passage. Example number of anchoring members considered suitable to include on an elongate member include, but are not limited to, one, at least one, two, a plurality, three, four, five, six, seven, eight, and any other number considered suitable for a particular application. Example locations considered suitable to position an anchoring member include, but are not limited to, positioning a first anchoring member proximal to a second anchoring member, a second anchoring member proximal to a third anchoring member, and any other location considered suitable for a particular application.

Figure 17C:
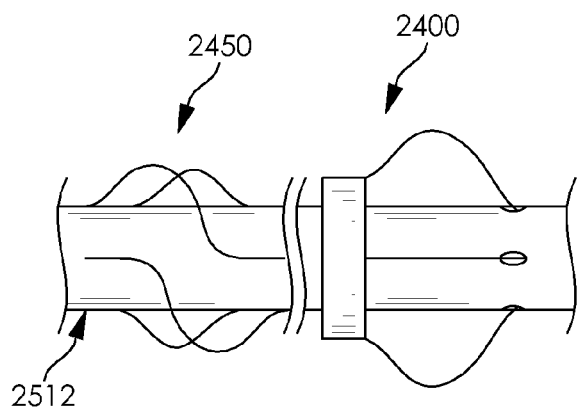
FIG. 17C is a partial side view of a medical device that has a fifth alternative anchoring member.

FIG. 17C illustrates a first anchoring member 2450 and a second anchoring member 2400 disposed on an elongate member 2512. Elongate member 2512 is similar to elongate member 1712 illustrated in FIG. 15D, and described above, except as detailed below. With respect to elongate member 2512, reference numbers in FIG. 17C refer to the same structural element or feature referenced by the same number in FIG. 15D, offset by 800. First anchoring member 2450 is similar to anchoring member 2450 illustrated in FIG. 17A, and described above, except as detailed below. With respect to first anchoring member 2450, reference numbers in FIG. 17C refer to the same structural element or feature referenced by the same number in FIG. 17A. Second anchoring member 2400 is similar to anchoring member 2400 illustrated in FIG. 17, and described above, except as detailed below. With respect to second anchoring member 2400, reference numbers in FIG. 17C refer to the same structural element or feature referenced by the same number in FIG. 17.

In the illustrated embodiment, first anchoring member 1450 is disposed proximal to second anchoring member 1400 along the length of elongate member 2512. The inclusion of a first anchoring member 1450 and a second anchoring member 1400 provides two locations in which elongate member 2512 can be fixedly, or releasably, attached and/or centered within a bodily passage.

Figure 18:
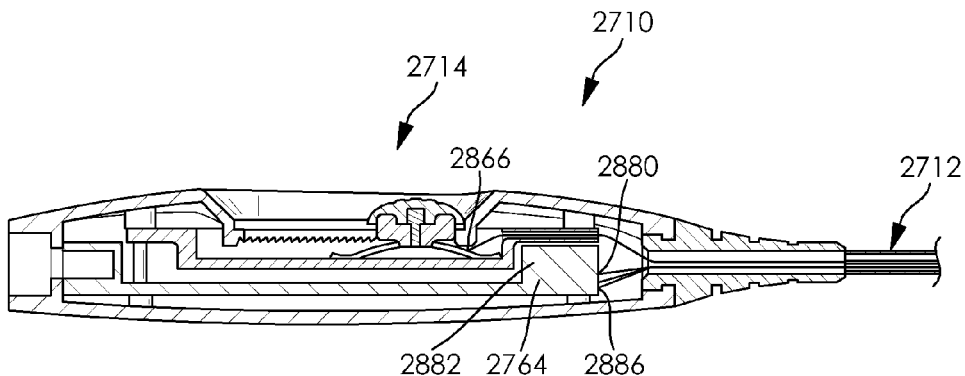
FIG. 18 is a partial sectional view of another exemplary medical device.
Figure 18A:
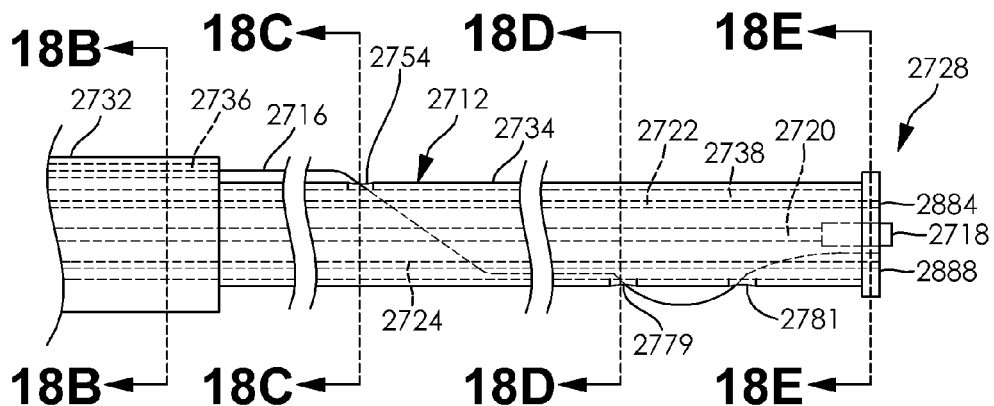
FIG. 18A is a partial side view of the medical device illustrated in FIG. 18.
Figure 18B:
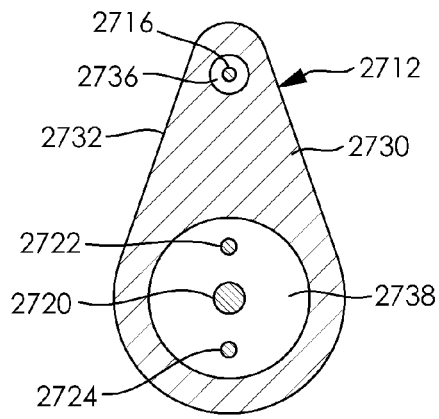
FIG. 18B is a sectional view of the medical device illustrated in FIG. 18A, taken along line 18B-18B.
Figure 18C:
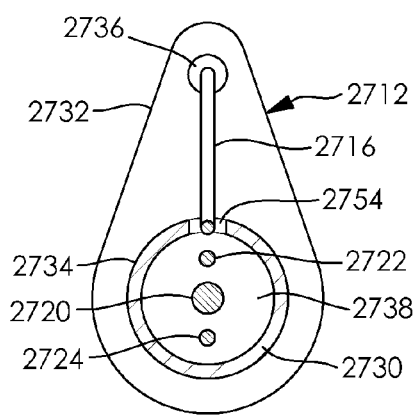
FIG. 18C is a sectional view of the medical device illustrated in FIG. 18A, taken along line 18C-18C.
Figure 18D:
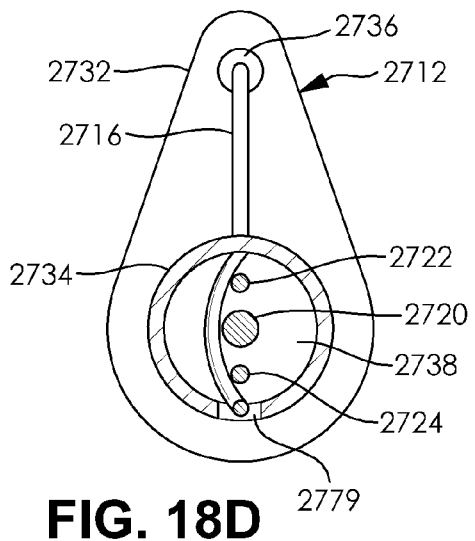
FIG. 18D is a sectional view of the medical device illustrated in FIG. 18A, taken along line 18D-18D.
Figure 18E:
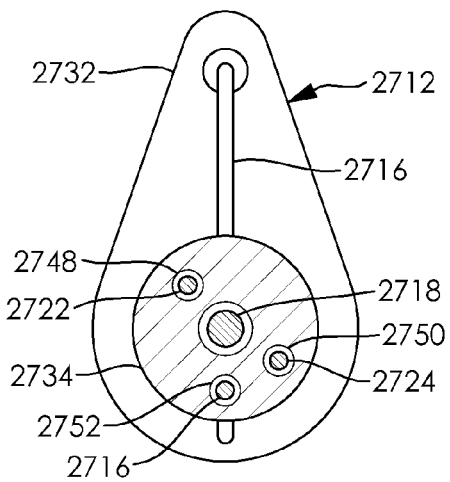
FIG. 18E is a sectional view of the medical device illustrated in FIG. 18A, taken along line 18E-18E.
Figure 18F:
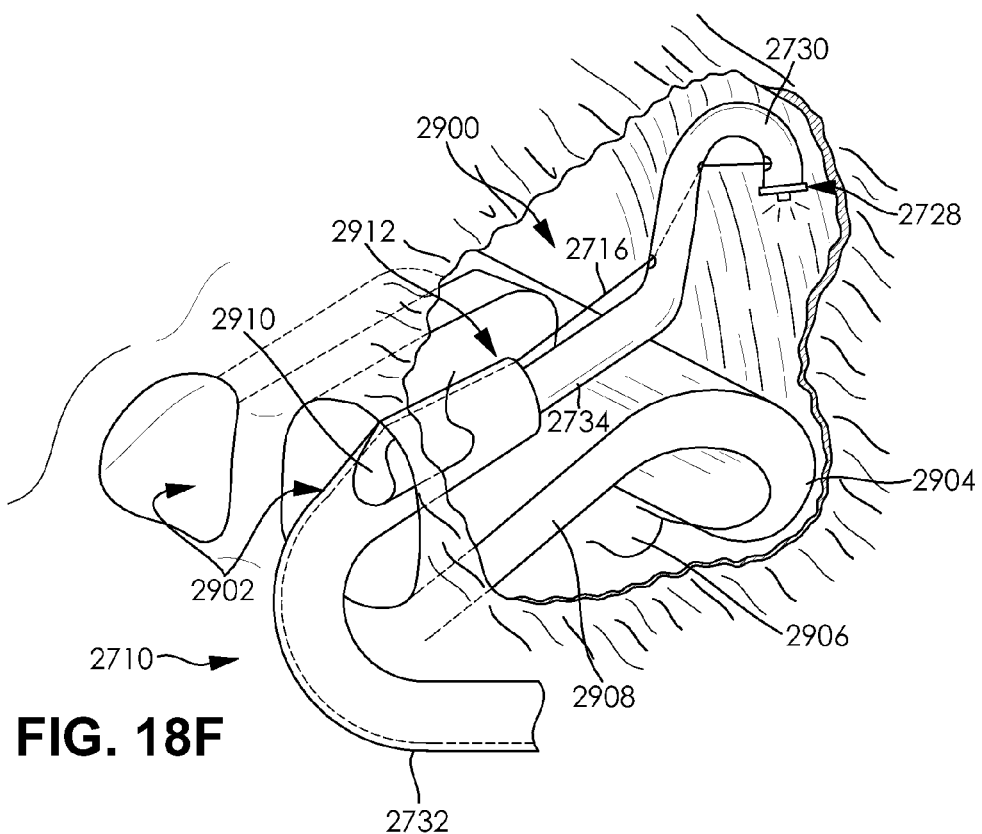
FIG. 18F is a partial perspective view of the medical device illustrated in FIGS. 18 and 18A partially disposed within a bodily passage.

FIGS. 18, 18A, 18B, 18C, 18D, 18E, and 18F illustrate another exemplary medical device 2710. In the illustrated embodiment, medical device 2710 is similar to medical device 10 illustrated in FIGS. 1, 2, 2A, 2B, 2C, 3, 4, and 5, and described above, except as detailed below. Reference numbers in FIGS. 18, 18A, 18B, 18C, 18D, 18E, and 18F refer to the same structural element or feature referenced by the same number in FIGS. 1, 2, 2A, 2B, 2C, 3, 4, and 5, offset by 2700. Thus, medical device 2710 comprises an elongate member 2712, handle 2714, and wire member 2716. FIGS. 18, 18A, 18B, 18C, 18D, and 18E illustrate the medical device 2710 in a first configuration and free of a bodily passage and FIG. 18F illustrates medical device 2710 in a second configuration and partially disposed within a bodily passage.

In the illustrated embodiment, elongate member 2712 defines elongate member third aperture 2779 and elongate member fourth aperture 2781 and wire member 2716 is attached within wire member opening 2752.

Elongate member third aperture 2779 is disposed between elongate member first aperture 2754 and elongate member distal end 2728. Elongate member fourth aperture 2781 is disposed between elongate member third aperture 2779 and elongate member distal end 2728. Thus, elongate member first aperture 2754, elongate member third aperture 2779, and elongate member fourth aperture 2781 are spaced longitudinally along the length of elongate member 2712. Each of the elongate member first aperture 2754, elongate member third aperture 2779, and elongate member fourth aperture 2781 extends through elongate member body 2730 and provides access to second elongate member lumen 2738 and is adapted to receive a portion of wire member 2716.

In the illustrated embodiment, each of the distal end of the first elongate member lumen 2736, elongate member first aperture 2754, elongate member third aperture 2779, and elongate member fourth aperture 2781 is disposed on a plane that contains the lengthwise axis of the elongate member 2712. In the illustrated embodiment, the elongate member first aperture 2754 is disposed on a first side of elongate member 2712 that is opposably facing, or substantially opposably facing, a second side of elongate member 2712 on which each of elongate member third aperture 2779 and elongate member fourth aperture 2781 is disposed.

Wire member 2716 extends from wire member first end 2866 through first elongate member lumen 2736 to elongate member first aperture 2754, passes through elongate member first aperture 2754 and into second elongate member lumen 2738 and extends to elongate member third aperture 2779, passes through elongate member third aperture 2779 and along the exterior of elongate member 2712 to elongate member fourth aperture 2781, passes through elongate member fourth aperture 2781 and into second elongate member lumen 2736 and is attached to elongate member 2712 at wire member opening 2752.

Imaging device 2718 is disposed at elongate member distal end 2728 and is operatively coupled to a control board 2764 by a data transfer cable 2720. Imaging device 2718 is adapted to obtain images of features and/or material disposed distal to elongate member 2712 and transmit the images to control board 2764 via data transfer cable 2720, or to another device wirelessly, or otherwise. Alternative to imaging device 2718 being disposed at elongate member distal end 2728, an imaging device can be disposed between an elongate member proximal end and an elongate member distal end such that the imaging device is disposed through an opening defined by the body of the elongate member and can obtain images radially from the elongate member. Optionally, an objective or image-forming lens can be disposed distal to imaging device 2718 that is adapted to focus an image upon the imaging device 2718.

Control board 2764 comprises a energy storage device, computer-readable medium, storage device, processor, light source, data transfer device, communication device, and/or one or more switches for manipulating the function of, or data received from, imaging device 2718, first optical fiber 2722, and/or second optical fiber 2724. Control board 2764 is adapted to obtain and process data and/or signals from imaging device 2718 and store the data and/or signals on a local or remote storage device, communicate the data and/or signals to another device, and/or display the data and/or signals on a display device (e.g., monitor, television). The data and/or signals can be processed into any suitable format (e.g., S-video) and the functions of the imaging device 2718, or the data received from imaging device 2718, can be controlled, for example, using a graphical user interface (GUI) and an input device (e.g., mouse).

Control board 2764 can comprise any suitable device and/or system capable of receiving signals and/or images from an imaging device, processing the signals and/or images, storing the signals and/or images, and/or outputting the signals and/or images to a display, device, system, and/or remote device or system. Skilled artisans will be able to select a suitable device and/or system capable of receiving signals and/or images from an imaging device, processing the signals and/or images, storing the signals and/or images, and/or outputting the signals and/or images to a display or other device or system according to a particular embodiment based on various considerations, including the type of procedure being performed. Example devices and systems considered suitable include, but are not limited to, general-purpose computers, special purpose computers, display devices, processors, display systems, storage devices, and any other device and/or system considered suitable for a particular application.

Each of the first optical fiber 2722 and second optical fiber 2724 defines a light path along its length. First optical fiber first end 2880 and second optical fiber first end 2886 are each operatively coupled to light source 2882 attached to control board 2764. First optical fiber second end 2884 is attached to elongate member 2712 within first optical fiber opening 2748 and second optical fiber second end 2888 is attached to elongate member 2712 within second optical fiber opening 2750.

Any suitable optical fiber can be used in combination with medical device 2710 and/or the medical devices described herein, and skilled artisans will be able to select a suitable optical fiber according to a particular embodiment based on various considerations, including the desired bodily passage within which a medical device is intended to be disposed. Example optical fibers considered suitable include, but are not limited to, commercially available optical fibers such as plastic optical fibers and glass optical fibers, with or without cladding.

Any suitable light source can be used, and skilled artisans will be able to select a suitable light source according to a particular embodiment based on various considerations, including the desired bodily passage within which a medical device is intended to be used. Example light sources considered suitable include, but are not limited to, commercially-available light sources such as xenon, laser, LED, and halogen light sources. Alternatively, an optical fiber first end can be attached to a light source that is separate from a control unit. Optionally, the light source can include a fiber coupling (not shown) which provides communication between the light source and first optical fiber 2722 and second optical fiber 2724. Light generated by light source travels through the light path defined by first optical fiber 2722 and second optical fiber 2724 and is emitted axially from each optical fiber second end 2884, 2888.

It is noted that while a first optical fiber 2722 and second optical fiber 2724 are illustrated, one or more different optical fibers can be used in combination, or independently, to provide axially directed and/or radially directed light. The one or more optical fibers can extend through the same or different lumens of an elongate member and can be operatively connected or attached to the same or two different light sources.

While an imaging device 2718, first optical fiber 2722, and second optical fiber 2724 have been illustrated and described as included in medical device 2710, a medical device can include any suitable device. Skilled artisans will be able to select a suitable device to include with a medical device according to a particular embodiment based on various considerations, including the physiological properties desired to be obtained and/or recorded during the performance of a procedure. For example, a medical device can include one or more transducers (e.g., mechanical transducers, pressure transducers, motion sensors, temperature transducers, acoustic transducers, electrical transducers, electromechanical transducers, thermal transducers, light transducers) adapted to obtain data relating to a bodily passage (e.g., airway) during the performance of a procedure.

FIG. 18F illustrates medical device 2710 in a second configuration and partially disposed in a bodily passage. In the illustrated embodiment, the bodily passage is an airway 2900 having an airway opening 2902. In addition, the soft pallet 2904, uvula 2906, hard pallet 2908, inferior turbinate 2910, and septum 2912 have been illustrated for clarity.

Medical device 2710 has been passed through the airway opening 2902 such that elongate member first portion 2732 is disposed within airway 2900 between the inferior turbinate 2910 and septum 2912 and elongate member distal end 2728 is disposed superiorly within airway 2900. The position of elongate member distal end 2728 is based on the position of actuator (not shown). The structural configuration of elongate member first portion 2732 relative to elongate member second portion 2734 reduces, or substantially reduces, rotation of elongate member distal end 2728 when elongate member second portion 2732 interacts with a portion of the bodily passage (e.g., septum and inferior turbinate). Optionally, an elongate member can include an anchoring member, such as those described herein, to maintain the position of the elongate member within a bodily passage during the performance of a procedure (e.g., sleep study).

Optionally, medical device 2710, or any other medical device described herein, can be passed through a sheath disposed, or partially disposed, in a bodily passage. A sheath can comprise a sheath proximal end, sheath distal end, and a sheath body that defines a sheath lumen that extends from a first opening defined on, or near, the sheath proximal end to a second opening defined on, or near, the sheath distal end. The sheath can be passed into the bodily passage prior to, or simultaneously, with a medical device being passed into and through the sheath lumen. Optionally, the sheath can define one or more pores along its length such that each of the one or more pores are in fluid communication with a sheath second lumen defined by the sheath body such that a medication introduced into sheath second lumen can be passed through each pore of the one or more pores. Optionally the sheath can include an anchoring device, such as those described herein. Passing a medical device through a sheath lumen can reduce interaction between the medical device and the wall of the bodily passage. In instances when a medical device is passed through a sheath lumen, an anchoring member included on an elongate member will move from a first configuration to a second configuration when the anchoring member is disposed within sheath lumen. Once the anchoring member is disposed distal to the sheath distal end, the anchoring member will move from a second configuration to the first configuration to anchor the elongate member within the bodily passage.

FIG. 19 is a schematic representation of an exemplary imaging system 3000 comprising a medical device 3110, control unit 3002, local image display 3004, an archival and communication system 3006, external storage 3008, and user input device 3010. Medical device 3110 is similar to medical device 2710 illustrated in FIGS. 18, 18A, 18B, 18C, 18D, 18E and 18F described above, except as detailed below. With respect to medical device 3110, reference numbers in FIG. 19 refer to the same structural element or feature referenced by the same number in FIGS. 18, 18A, 18B, 18C, 18D, 18E and 18F, offset by 400. Thus, medical device 3110 comprises an elongate member 3112 and handle 3114.

While imaging system 3000 has been illustrated as including medical device 3110, an imaging system (e.g., imaging system 3000, imaging system 3030) can include any suitable medical device, and skilled artisans will be able to select a suitable medical device to include in an imaging system according to a particular embodiment based on various considerations, including the procedure intended to be performed. Example medical devices considered suitable to include in an imaging system include, but are not limited to, medical device 10, medical device 310, medical device 510, medical device 710, medical device 910, medical device 1110, medical device 1310, medical device 1510, medical device 1710, medical device 1910, medical device 1910', medical device 2110, medical device 2710, and any other medical device considered suitable for a particular embodiment.

In the illustrated embodiment, handle 3114 is adapted to house an image and signal buffer 3012 and includes one or more switches 3014 that are adapted to interact with imaging device 3118 and control unit 3002 to control the data and/or signals obtained by imaging device 3118. Control unit 3002 includes an image and/or signal processor 3016, which receives raw video input 3002', a communications port 3018, and a video output 3020. Medical device 3110 is attached to control unit 3002 using an HDMI cable 3022. However, other methods of attachment (e.g., signal communication) between a control unit and a medical device are considered suitable, such as those described herein. Medical device 3110 is attached to control unit 3002 such that imaging device 3118 is in communication with control unit 3002.

Control unit 3002 can comprise any suitable device, such as a general purpose or special purpose computer adapted to be attached to, or included with, a medical device, such as those described herein. For example, control unit 3002 may be any one of a personal computer system, a work station computer system, a laptop computer system, an embedded controller system, a microprocessor-based system, a digital signal processor-based system, a hand held device system, a personal digital assistant (PDA) system, a wireless system, a wireless networking system, mobile device, mobile telephone, smart phone, electronic device, such as those described herein, or any other device considered suitable for a particular application. The control unit 3002 can include any suitable energy storage device (e.g., battery), a bus or other communication mechanism for communicating information and a processor coupled with bus for processing the information (e.g., signal processor 3016). The control unit 3002 can also include a main memory, such as a random access memory (RAM) or other dynamic storage device (e.g., dynamic RAM (DRAM), static RAM (SRAM), synchronous DRAM (SDRAM), flash RAM)), coupled to the bus for storing information and instructions to be executed by the processor. In addition, the main memory may be used for storing temporary variables or other intermediate information during execution of instructions to be executed by the processor. Control unit 3002 can further include a read only memory (ROM) or other static storage device (e.g., programmable ROM (PROM), erasable PROM (EPROM), and electrically erasable PROM (EEPROM)) coupled to the bus for storing static information and instructions for the processor. A storage device, such as a magnetic disk or optical disk, can be provided and coupled to the bus for storing information and instructions, such as instructions for completing one or more of the methods, elements, steps, optional steps, alternative steps, and/or components described herein.

The control unit 3002 may also include input/output ports to couple the control unit 3002 to external devices, such as external storage 3008. External storage 3008 can comprise any suitable computer readable media, such as those described herein. Such coupling may include direct electrical connections, wireless connections, networked connections, etc., for implementing automatic control functions, remote control functions, etc.

The control unit 3002 may also include special purpose logic devices (e.g., application specific integrated circuits (ASICs)) or configurable logic devices (e.g., generic array of logic (GAL) or re-programmable field programmable gate arrays (FPGAs)). Other removable media devices (e.g., a compact disc, a tape, and a removable magneto-optical media) or fixed, high-density media drives may be added to the control unit 3002 using an appropriate device bus (e.g., a small computer system interface (SCSI) bus, an enhanced integrated device electronics (IDE) bus, or an ultra-direct memory access (DMA) bus). The control unit 3002 may additionally include a compact disc reader, a compact disc reader-writer unit, each of which may be connected to the same device bus or another device bus.

The control unit 3002 may be coupled via the bus to a monitor (e.g., 3004) via any suitable output (e.g., video output 3020), such as a cathode ray tube (CRT), liquid crystal display (LCD), Light-emitting Diode (LED) display, plasma display, voice synthesis hardware and/or software, etc., for displaying and/or providing information to a computer user (e.g., one or more of the methods, elements, steps, optional steps, alternative steps, and/or components described herein). A display or graphics card may control the display. The control unit 3002 can include input devices (e.g., 3010), such as a keyboard and a cursor control, for communicating information and command selections to the processor. Such command selections can be implemented via voice recognition hardware and/or software functioning as the input devices. The cursor control, for example, can be a mouse, a trackball, cursor direction keys, touch screen display, optical character recognition hardware and/or software, voice recognition hardware and/or software, etc., for communicating direction information and command selections to the processor and for controlling cursor movement on the display. In addition, a printer may provide printed listings of the data structures, information, etc., or any other data stored and/or generated by the control unit 3002.

The control unit 3002 can perform a portion, or the entirety, of the processing steps, methods, elements, steps, optional steps, alternative steps, and/or components as described herein in response to the processor executing one or more sequences of one or more instructions contained in a memory, such as the main memory. Such instructions may be read into the main memory from another computer readable medium, such as a storage device, another computer, or otherwise. One or more processors in a multi-processing arrangement may also be employed to execute the sequences of instructions contained in the main memory. In alternative embodiments, hard-wired circuitry may be used in place of or in combination with software instructions. Thus, embodiments are not limited to any specific combination of hardware circuitry and software.

As stated above, the control unit 3002 includes at least one computer readable medium or memory programmed according to one or more of the methods, elements, steps, optional steps, alternative steps, and/or components described herein and/or for containing data structures, tables, records, or other data described herein. Examples of computer readable media are compact discs, hard disks, floppy disks, tape, magneto-optical disks, PROMs (EPROM, EEPROM, Flash EPROM), DRAM, SRAM, SDRAM, etc. Stored on any one or on a combination of computer readable media, the one or more methods, elements, steps, optional steps, alternative steps, and/or components described herein can include software for controlling the computer system, for driving a device or devices (e.g., one or more processors) for implementing the one or more methods, elements, steps, optional steps, alternative steps, and/or components described herein, and/or for enabling the computer system to interact with a human user. Such software may include, but is not limited to, device drivers, operating systems, development tools, and applications software. Such computer readable media further includes the computer program product of the one or more methods, elements, steps, optional steps, alternative steps, and/or components described herein for performing a portion (e.g., if processing is distributed), or the entirety, of the processing performed in implementing the one or more methods, elements, steps, optional steps, alternative steps, and/or components described herein.

Any method, element, step, optional step, alternative step, logic, and/or application described herein can comprise software or code that can be embodied in a non-transitory computer-readable medium, or one or more non-transitory computer-readable storage media, for use by or in connection with an instruction execution system such as, for example, a processor in a computing system (e.g., control unit 3002) or other system. In this sense, the method, element, step, optional step, alternative step, logic, or application, may comprise, for example, statement including instructions and declarations that can be fetched from the computer-readable medium and executed by the instruction execution system.

The term "computer readable medium" as used herein refers to any medium that can provide instructions to a processor for execution. A computer readable medium may take many forms, including but not limited to, non-volatile media, volatile media, and transmission media. Non-volatile media includes, for example, optical, magnetic disks, and magneto-optical disks, such as the storage device. Volatile media includes dynamic memory, such as the main memory. Transmission media includes coaxial cables, copper wire and fiber optics, including the wires that comprise the bus. Transmission media also may also take the form of acoustic or light waves, such as those generated during radio wave and infrared data communications.

Common forms of computer readable media include, for example, non-transitory media, non-transitory computer-readable storage media, hard disks, floppy disks, tape, magneto-optical disks, PROMs (EPROM, EEPROM, Flash EPROM), DRAM, SRAM, SDRAM, or any other magnetic medium, compact disks (e.g., CD-ROM), or any other optical medium, punch cards, paper tape, or other physical medium with patterns of holes, a carrier wave (described below), or any other medium from which a computer can read.

Various forms of computer readable media may be involved in carrying out, or containing, one or more sequences of one or more instructions to a processor for execution. For example, the one or more methods, elements, steps, optional steps, alternative steps, and/or components described herein can be described in the general context of computer executable instructions, such as program modules, or program components, being executed by a computer. Program modules or components include routines, objects, data structures, tasks, etc. that can perform particular tasks or implement particular abstract data types. For example, the instructions may initially be carried on a magnetic disk of a remote computer. The remote computer can load the instructions for implementing a portion, or the entirety, of the one or more methods, elements, steps, optional steps, alternative steps, and/or components described herein, remotely into a dynamic memory and send the instructions over a telephone line using a modem. Alternatively, in another example, the instructions can be sent over a network connection using a modem, a network interface card, a wireless connection, or any other suitable form of network connection.

The control unit 3002 can also include a communication interface (e.g., communications port 3018) coupled to the bus. The communication interface provides a two-way data communication coupling to a network link that may be connected to, for example, a local network. For example, the communication interface may be a network interface card to attach to any packet switched local area network (LAN). As another example, the communication interface may be an asymmetrical digital subscriber line (ADSL) card, an integrated services digital network (ISDN) card or a modem to provide a data communication connection to a corresponding type of telephone line. Wireless links may also be implemented via the communication interface. In any such implementation, the communication interface sends and receives electrical, electromagnetic, or optical signals that carry digital data streams representing various types of information.

The network link typically provides data communication through one or more networks to other data devices. For example, the network link may provide a connection to a computer, such as a computer that includes the components described with respect to control unit 3002 (e.g., archival and communication system 3006), through local network (e.g., a LAN) or through equipment operated by a service provider, which provides communication services through a communications network. In some embodiments, the local network and the communications network use electrical, electromagnetic, or optical signals that carry digital data streams. The signals through the various networks and the signals on the network link and through the communication interface, which carry the digital data to and from control unit 3002, are exemplary forms of carrier waves transporting the information. The control unit 3002 can transmit notifications and receive data, including program code, through the network(s), network link and communication interface. Alternatively, near field communication (NFC) can be utilized to provide data communication between one or more devices and/or systems.

Any of the imaging systems described herein can include any of the devices, systems, and/or components as described above with respect to control unit 3002. Skilled artisans will be able to select a suitable device, system, and/or component to include in imaging system according to a particular embodiment based on various considerations, including the intended use of the imaging system. Examples of imaging systems considered suitable to include one or more of the devices, systems, or components described above with respect to control unit 3002 include imaging system 3000, imaging system 3030, and any other imaging system considered suitable for a particular embodiment.

In use, when imaging device 3118 obtains an image, it is transferred to control unit 3002 which is adapted to process the image so that it can be provided to local image display 3004, archival and communication system 3006, external storage 3008, and/or any other suitable device. Each of the one or more switches 3014 and/or user input device 3010 is adapted to initiate certain functions within control unit 3002, such as freezing an image, unfreezing an image, and/or capturing an image. When a function is initiated by a switch 3014 and/or user input device 3010, the images obtained by imaging device 3118 can be communicated to local image display 3004 through video output 3020, through image and/or signal processor 3016 to archival and communication system 3006 through communications port 3018, and/or any other suitable device adapted to capture the image(s) and store the image(s) on a local and/or remote storage device. In addition, when a function is initiated by a switch 3014 and/or user input device 3010, the image and/or data can be written to a storage device (e.g., external storage 3008).

FIG. 19A is an alternative schematic representation of an exemplary imaging system 3030 similar to schematic 3000 except that the one or more switches (e.g., one or more switches 3014) have been omitted and a transducer 3032 is disposed elongate member distal end 3128 that is in signal communication with control unit 3002. Medical device 3110 is attached to control unit 3002 such that each of the imaging device 3118 and transducer 3032 is in communication with control unit 3002.

Transducer 3032 can comprise any suitable device capable of converting one form of energy to another form of energy. Skilled artisans will be able to select a suitable transducer to include on an elongate member according to a particular embodiment based on various considerations, including the bodily passage within which a medical device and/or scope is intended to be used. Example transducers considered suitable include, but are not limited to mechanical transducers, pressure transducers, motion sensors, temperature transducers, acoustic transducers, electrical transducers, electromechanical transducers, thermal transducers, light transducers, and any other transducer considered suitable for a particular application.

The inclusion of a transducer 3032 on elongate member 3112 can reduce the amount of imagery needed to review one or more events that occur during performance of a procedure (e.g., sleep study), and/or provides a mechanism to locate certain events that occur during the performance of a procedure without having to review the entire procedure. The inclusion of a transducer 3032 provides a mechanism for incorporating safety features into the performance of a procedure. For example, if a control unit 3002 receives a transducer 3032 signal, an alarm can be activated or a signal can be sent to a local and/or remote device and/or system to notify personnel.

Alternative to transducer 3032 being disposed on elongate member distal end 3128, a transducer can be positioned at any suitable location on an elongate member, or imaging system. For example, a transducer cable could bifurcate from an elongate member at a point proximal to the elongate member distal end, bifurcate from a cable disposed through an elongate member and connected to a control unit, or a transducer cable could be directly attached to a control unit. When a transducer is directly attached to a control unit the transducer can be reusable.

Example methods of configuring a control unit 3002 and/or the software contained thereon for performing a procedure are described below with respect to performing a sleep study. While the methods described below are illustrative of performing a sleep study, the steps, alternative steps, and/or optional steps, can be used to perform any suitable procedure.

A first example method of configuring a control unit 3002 and/or the software contained thereon for performing a procedure comprises initiating a recording sequence, which could have a length predetermined by a user or the software, when transducer 3032 provides a signal to control unit 3002, or when user or software defined transducer 3032 signal characteristics have been met. During the recording sequence, additional transducer 3032 signals can be ignored, and/or used to further configure control unit 3002 and/or the software contained thereon. Once the predetermined recording period has elapsed, the transducer 3032 signals can be further monitored to begin recording for a second interval of time. A recording sequence can include the recording of signals received from a transducer and/or images obtained by an imaging device, as described herein.

Alternatively, during the recording of a procedure and once control unit 3002 receives a transducer 3032 signal, the control unit 3002 can create a time-stamp on the data, or tag the data, provided by the transducer 3032 and/or imaging device 3118 such that the location of the transducer 3032 signal, and the associated data (e.g., image) from the imaging device 3118, can be located within the recorded data. A time-stamp, or tag, can be incorporated into the data and/or maintained in a separate data file so that each time-stamp, or tag, can be located. Alternatively, a time-stamp, or tag, can be incorporated into the images received from imaging device 3118. For example, if a temperature transducer is incorporated into a medical device, a tag and/or recording can be initiated once a temperature fluctuation is observed during the procedure.

Alternatively, transducer 3032 signals can be recorded (e.g., communicated to a storage device via a communications device and stored) for a first interval of time (e.g., a portion, or the entirety, of a procedure) and the data provided by the imaging device 3118 can be recorded (e.g., communicated to a storage device via a communications device and stored) for a second interval of time. The first interval of time and second interval of time can be concurrent with one another, consecutive to one another, or separated by an interval of time. When the first interval of time and second interval of time are concurrent with one another, the transducer 3032 signals are tied, or associated with, the data provided by an imaging device 3118. The transducer 3032 signals and the data provided by imaging device 3118 can be provided to a user in any suitable manner, such as those described herein. The transducer 3032 signals can be disposed on a monitor in a first display region and the data (e.g., images) provided by imaging device 3118 can be disposed on the monitor in a second display region. In the first display region, the transducer 3032 signals are displayed relative to the first interval of time. The first region comprises a bar, or slider, that is moveable relative to the first interval of time. As the bar, or slider, is moved relative to the first interval of time, the second display region displays the data (e.g., images) provided by imaging device 3118 at the point, or range in time, that the bar, or slider, is positioned over the transducer 3032 data. For example, if imaging device 3118 recorded video during the second interval of time, as the bar, or slider, is moved relative to the first interval of time and the transducer 3032 signals, the image, or video, recorded by imaging device 3118 can be displayed on the monitor in the second display region. This provides a mechanism for locating a desired event (e.g., apneic event), as indicated by transducer 3032 signals, and viewing data (e.g., images) associated with the event. While a monitor has been described as displaying a first region and second region, any suitable number of monitors, and/or regions, can be used, such as more than one, two, or any other suitable number.

Figure 26:
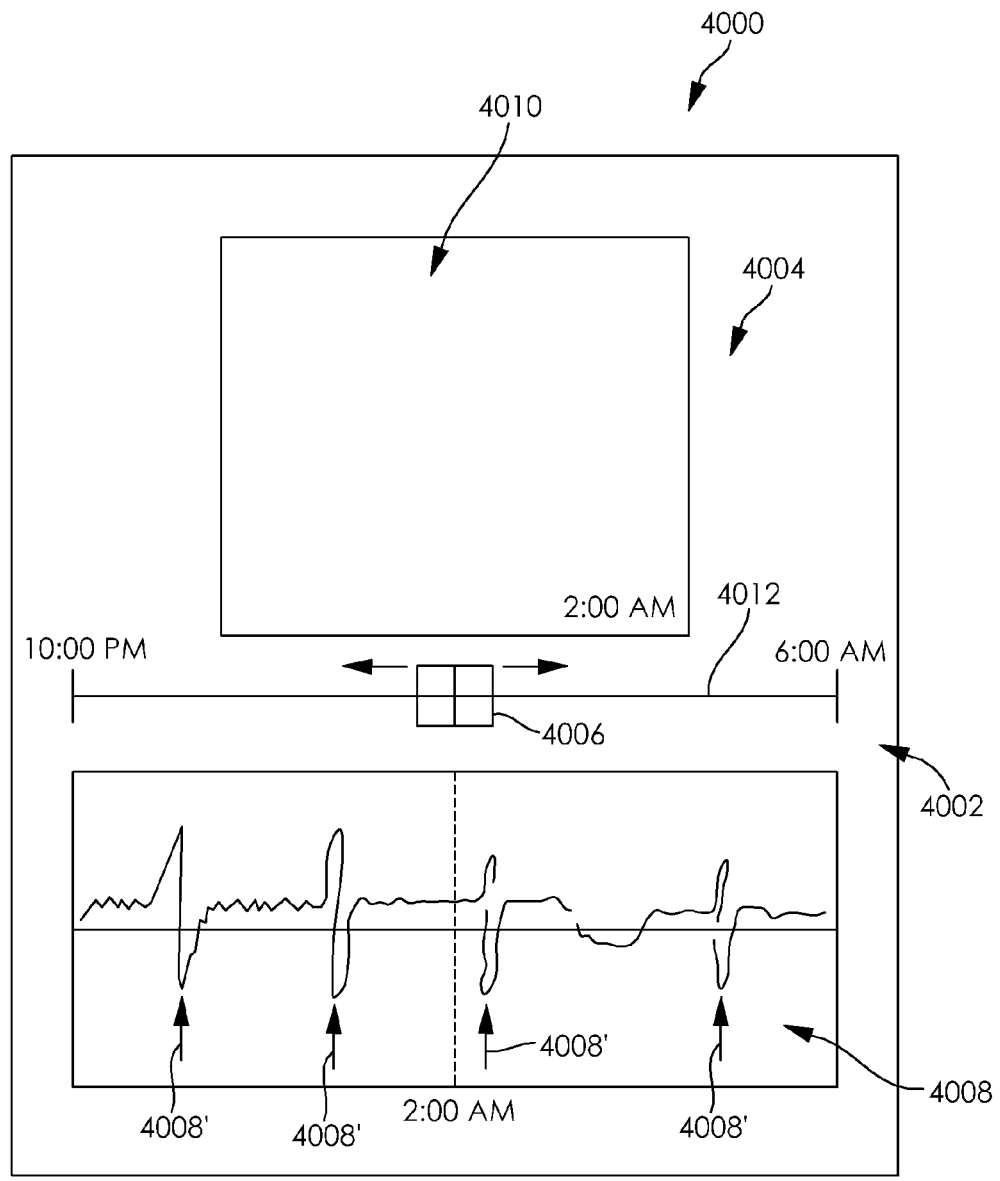
FIG. 26 illustrates data obtained during a sleep study displayed on a monitor.

FIG. 26 illustrates a monitor 4000 that displays transducer 3032 signals that are associated with the images provided by an imaging device 3118 such that the first interval of time in which the transducer 3032 signals have been recorded is concurrent with the second interval of time in which the data provided by the imaging device 3118 has been recorded. The monitor 4000 has a first display region 4002 and a second display region 4004. The first display region 4002 has a user interface control, which in the embodiment illustrated is slider 4006, and displays the transducer 3032 signals 4008. While a slider has been described, other user interface controls are considered suitable, such as knobs, buttons, and any other user interface control considered suitable for a particular embodiment. The transducer signals 4008 have tags 4008' incorporated into the data to locate a desired event (e.g., apneic event). The second display region 4004 displays the images 4010 provided by the imaging device 3118. In the first display region 4002, the transducer signals 4008 are displayed relative to the first interval of time 4012 and the slider 4006 is moveable relative to the first interval of time 4012 (e.g., using a user input device). As the slider 4006 is moved relative to the first interval of time, the second display region 4004 displays the images 4010 provided by imaging device 3118 at the point, or range in time, that the slider 4006 is positioned (e.g., relative to the transducer 3032 signals 4008). Thus, movement of the user interface control alters the images provided in the second display region. This provides a mechanism for locating a desired event (e.g., apneic event), as indicated by transducer signals 4008 and viewing images 4010 associated with the event.

Any of the steps described herein can be embodied in a system, such as a control unit 3002, be implemented in a method, such as a method of performing a procedure, method of performing a sleep study, or a method of obtaining data (e.g., relating to a sleep study), or can be embodied on a computer-readable medium, such as those described herein. For example, a method, such as those described herein (e.g., method of performing a procedure, method of performing a sleep study, method of obtaining data, computer-implemented method) can comprise one or more of the steps described herein, such as the steps of: recording one or more transducer signals for a first interval of time; recording the data provided by an imaging device for a second interval of time, the second interval of time can be concurrent with the first interval of time, consecutive with the first interval of time, or separated by an interval of time from the first interval of time; associating the transducer signals with the data provided by the imaging device; displaying the transducer signals to a user (e.g., via monitor); displaying the data provided by the imaging device to the user (e.g., via monitor); displaying the transducer signals relative to the first interval of time; displaying the data provided by the imaging device relative to the second interval of time; providing the user with an interactive control, which can be provided on the display (e.g., monitor), or be a separate switch (e.g., control knob attached to the system, control knob attached to control unit), to locate (e.g., using a user input device, such as user input device 3010) a desired point in time within the first interval of time and/or a desired transducer signal; altering the displayed data provided by the imaging device relative to the desired point in time within the first interval of time. Any of these steps can be accomplished under the control of one or more computers configured with specific executable instructions capable of performing the one or more steps.

Alternatively, a system, such as those described herein, can comprise one or more processors and one or more computer-readable media (e.g., non-transitory computer readable media) embodying computer-executable instructions that, when executed, cause the one or more processors to perform one or more of the acts described herein, such as the following acts: recording one or more transducer signals for a first interval of time; recording the data provided by an imaging device for a second interval of time, the second interval of time can be concurrent with the first interval of time, consecutive with the first interval of time, or separated by an interval of time from the first interval of time; associating the transducer signals with the data provided by the imaging device; displaying the transducer signals to a user (e.g., via monitor); displaying the data provided by the imaging device to the user (e.g., via monitor); displaying the transducer signals relative to the first interval of time; displaying the data provided by the imaging device relative to the second interval of time; providing the user with an interactive control, which can be provided on the display (e.g., monitor), or be a separate switch (e.g., control knob attached to the system, control knob attached to control unit), to locate (e.g., using a user input device, such as user input device 3010) a desired point in time within the first interval of time and/or a desired transducer signal; altering the displayed data provided by the imaging device relative to the desired point in time within the first interval of time.

Alternatively, a computer-readable storage media (e.g., non-transitory computer-readable storage media), such as those described herein, that stores computer-executable instructions that, when executed, cause one or more processors to perform any act described herein, such as the following acts: recording one or more transducer signals for a first interval of time; recording the data provided by an imaging device for a second interval of time, the second interval of time can be concurrent with the first interval of time, consecutive with the first interval of time, or separated by an interval of time from the first interval of time; associating the transducer signals with the data provided by the imaging device; displaying the transducer signals to a user (e.g., via monitor); displaying the data provided by the imaging device to the user (e.g., via monitor); displaying the transducer signals relative to the first interval of time; displaying the data provided by the imaging device relative to the second interval of time; providing the user with an interactive control, which can be provided on the display (e.g., monitor), or be a separate switch (e.g., control knob attached to the system, control knob attached to control unit), to locate (e.g., using a user input device, such as user input device 3010) a desired point in time within the first interval of time and/or a desired transducer signal; altering the displayed data provided by the imaging device relative to the desired point in time within the first interval of time.

Alternatively, during the recording of a procedure and once control unit 3002 receives a transducer 3032 signal, the control unit 3002 can stop a first recording sequence and start a second, different, recording sequence. Thus, multiple recording sequences can be created based on transducer 3032 signals received by control unit 3002.

Any of the elements, features, and/or structural arrangements described herein with respect to any medical device, elongate member, handle, wire member, actuator, and/or imaging system, can be combined in any suitable manner, and skilled artisans will be able to select a suitable element, feature, and/or structural arrangement for a medical device, elongate member, handle, wire member, actuator, and/or imaging system according to a particular embodiment based on various considerations, such as the desired bodily passage within which a medical device is intended to be deployed.

Various methods are described herein. While the methods described herein are shown and described as a series of acts, it is to be understood and appreciated that the methods are not limited by the order of acts, as some acts may, in accordance with these methods, occur in different orders, and/or concurrently with other acts described herein.

Figure 20:
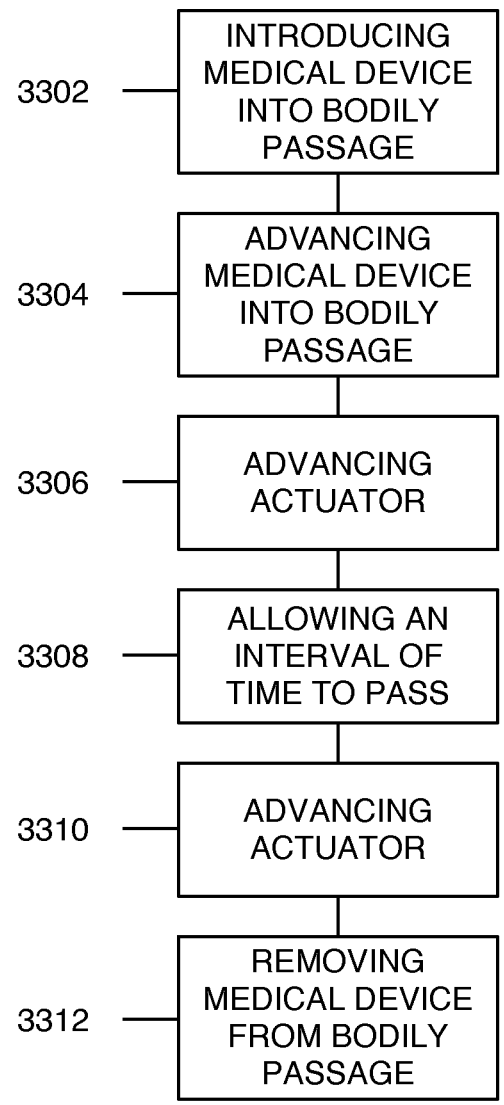
FIG. 20 is a flowchart representation of an exemplary method of visualizing a bodily passage.

FIG. 20 is a flowchart representation of an exemplary method 3300 of visualizing a bodily passage.

A step 3302 comprises introducing a medical device having a medical device proximal end and a medical device distal end into a bodily passage such that the medical device distal end is disposed in the bodily passage. The medical device comprising an elongate member, actuator, and a wire member. Another step 3304 comprises advancing the medical device distally and into the bodily passage such that an anchoring member is disposed in the bodily passage. Another step 3306 comprises advancing the actuator from an actuator first position to an actuator second position to define a curve along the length of the elongate member. Another step 3308 comprises allowing an interval of time to pass. Another step 3310 comprises advancing actuator from the actuator second position to the actuator first position. Another step 3312 comprises removing the medical device from the bodily passage.

Step 3302 can be accomplished by placing a proximally and/or distally directed force on any suitable portion of a medical device such that it is introduced into a bodily passage.

Step 3302 can be accomplished using any suitable medical device and/or imaging system, and skilled artisans will be able to select a suitable medical device and/or imaging system according to a particular embodiment based on various considerations, including the desired procedure intended to be performed. Example medical devices and imaging devices considered suitable include, but are not limited to, medical device 10, medical device 310, medical device 510, medical device 710, medical device 910, medical device 1110, medical device 1310, medical device 1510, medical device 1710, medical device 1910, medical device 1910', medical device 2110, medical device 2710, imaging system 3000, imaging system 3030, and any other suitable medical device and/or imaging system.

Furthermore, while method 3300 has been described as introducing a medical device into a bodily passage, it is considered suitable to deploy any suitable medical device into any suitable bodily passage. Skilled artisans will be able to select a suitable bodily passage to deploy a medical device according to a particular embodiment based on various considerations, including the desired procedure intended to be performed. Example bodily passages considered suitable include, but are not limited to, sinus passages, airways, sinus cavities, and any other bodily passage considered suitable for a particular application.

Step 3304 can be accomplished by applying a distally directed force on any suitable portion of the medical device such that it advances into the bodily passage and an anchoring member disposed on the elongate member is disposed within, or partially within, the bodily passage. Optionally, an anchoring member can be omitted from a medical device and a medical device can be advanced distally into a bodily passage such that a portion of the medical device (e.g., elongate member first portion 32) is disposed in the bodily passage (e.g., between the inferior turbinate and septum).

An optional step comprises bending the elongate member such that it is disposed at, or near, the cheek of the individual upon which a procedure is being performed. Bending an elongate member towards the cheek of an individual reduces the likelihood of the elongate member distal end from rotating during the performance of a procedure. Another optional step comprises attaching the elongate member to the cheek of the individual.

Step 3306 can be accomplished by a user applying a proximally directed force on the actuator, as described herein. The application of a proximally directed force on the actuator axially advances the wire member in the proximal direction such that the elongate member moves from a straight, or substantially straight, configuration, to a curved configuration in which elongate member defines one or more curves along its length.

Step 3308 can be accomplished by completing step 3304 and/or step 3306 and waiting for an interval of time to pass before completing step 3310 and/or step 3312. Any suitable interval of time is considered suitable, and skilled artisans will be able to select a suitable interval of time according to a particular embodiment based on various considerations, including the procedure being performed. Example intervals of time considered suitable include, but are not limited to, allowing one or more seconds to pass, one or more minutes to pass, one or more hours to pass, one or more days to pass, and any other interval of time considered suitable for a particular application.

An optional step comprises adjusting the position of the elongate member distal end within the bodily passage. This can be accomplished by moving the actuator between the actuator first position and actuator second position.

Step 3310 can be accomplished by a user applying a distally directed force on the actuator, as described herein. The application of a distally directed force on the actuator axially advances the wire member in the distal direction such that the elongate member moves to a straight, or substantially straight, configuration.

Step 3312 can be accomplished by placing a proximally and/or distally directed force on any suitable portion of a medical device such that it is withdrawn from the bodily passage.

An optional step comprises confirming placement of the elongate member and/or that the elongate member is defining one or more curves along its length. This optional step can be accomplished using any suitable method of visualization, and skilled artisans will be able to select a suitable method to visualize an elongate member according to a particular embodiment based on various considerations, such as the desired bodily passage within which a medical device is intended to be deployed. Example methods of visualization include, but are not limited, using direct visualization, fluoroscopy, a scope, transcutaneously, taking an x-ray, and any other method considered suitable for a particular application.

Another optional step comprises introducing a medication and/or fluid into a lumen defined by an elongate member such that it is passed through the lumen and exits an opening defined on the elongate member distal end. This optional step provides a mechanism for clearing the view of an imaging device when it has become obstructed or unclear.

While various steps, alternative steps, and optional steps have been described above with respect to introducing a medical device into a bodily passage, these steps, alternative steps, and optional steps can be included in, accomplished concurrently with, and/or accomplished in the alternative to, the methodology, steps, alternative steps, and/or optional steps described below with respect to methodology 3400.

Figure 21:
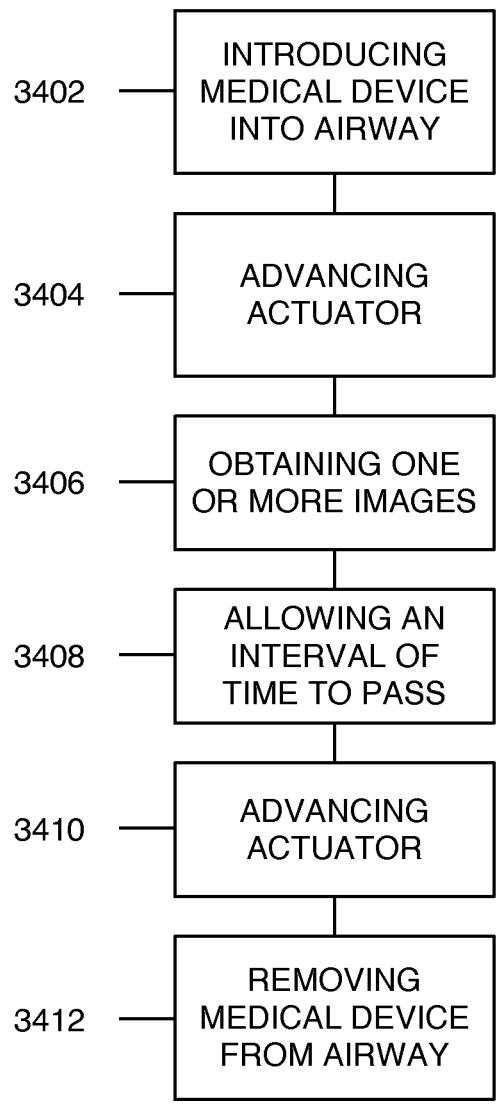
FIG. 21 is a flowchart representation of an exemplary method of performing a sleep study.
Figure 22:
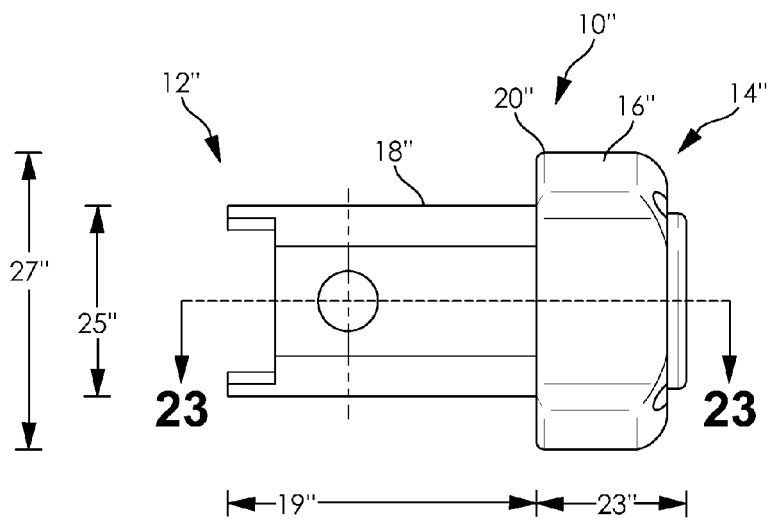
FIG. 22 is a side view of an exemplary cap that can be included on a medical device.
Figure 23:
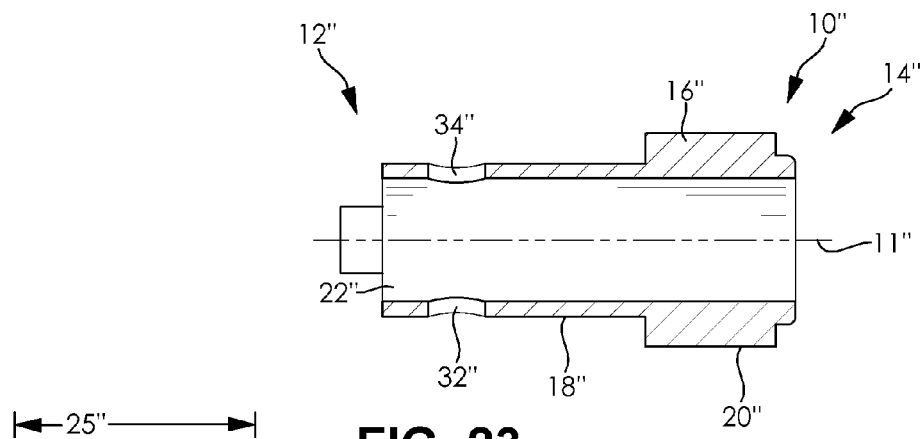
FIG. 23 is a sectional view of the cap illustrated in FIG. 22, taken along line 23-23.
Figure 24:
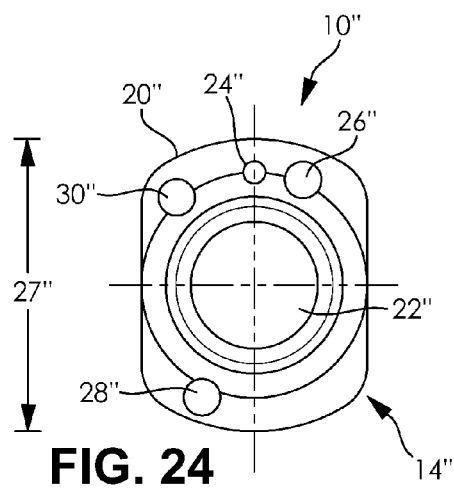
FIG. 24 is an end view of the distal end of the cap illustrated in FIG. 22.
Figure 25:
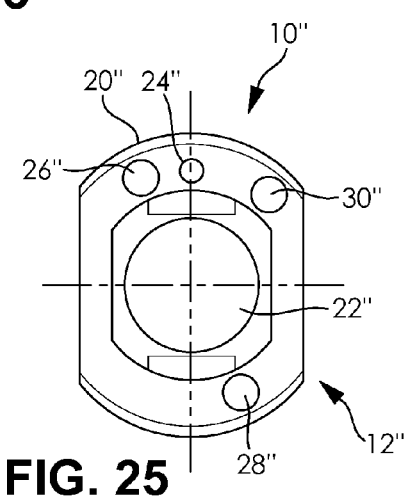
FIG. 25 is an end view of the proximal end of the cap illustrated in FIG. 22.

FIG. 21 is a flowchart representation of an exemplary method 3400 of performing a sleep study.

Method 3400 is similar to that described above with respect to method 3300, except as described below. A step 3402 comprises introducing a medical device having a medical device proximal end and a medical device distal end into an airway such that the medical device distal end is disposed in the airway. The medical device comprising an elongate member, actuator, and a wire member. Another step 3404 comprises advancing the actuator from an actuator first position to an actuator second position to define a curve along the length of the elongate member. Another step 3406 comprises obtaining one or more images of the airway. Another step 3408 comprises allowing an interval of time to pass. Another step 3410 comprises advancing actuator from the actuator second position to the actuator first position. Another step 3412 comprises removing the medical device from the airway.

Step 3402 can be accomplished prior, or subsequent, to the individual on whom the procedure is being performed entering a sleep state. An optional step comprises excluding administering a medication that artificially induces sleep such that the individual on which the procedure is being performed has natural, or substantially, natural body functions.

Step 3406 can be accomplished using any suitable method of obtaining one or more images of an airway, or bodily passage. For example, an imaging device included on a medical device can be activated such that one or more images are sent to a control board, or other device via wired data transfer cable or wirelessly, as described herein.

An optional step comprises attaching the medical device to a second device, such as a computer, network, storage device, computer readable storage medium, or any other suitable device, such as those described herein. Another optional step comprises storing the one or more images obtained by the imaging device relative to the interval of time. Another optional step comprises storing the data obtained by a transducer disposed on the medical device relative to the interval of time. Another optional step comprises displaying the one or more images obtained by the imaging device. Another optional step comprises displaying the data obtained by the transducer. Another optional step comprises displaying the one or more images obtained by the imaging device relative to the data obtained by the transducer.

An optional step comprises recording, or storing, a value of a physiological feature (e.g., air temperature, $O_2$ saturation) of the bodily passage or other anatomical location. This can be accomplished using one or more devices disposed within, or on, a medical device, as described herein. Another optional step comprises recording, or storing, a second value of a physiological feature of the bodily passage.

Optional steps comprise inserting a sheath having a sheath proximal end and a sheath distal end into a bodily passage such that the sheath distal end is disposed within the bodily passage. The sheath defining a lumen extending from a first opening defined on the sheath proximal end to a second opening defined on the sheath distal end. Another optional step comprises introducing the medical device into the sheath lumen and through the sheath such that the medical device distal end is disposed within the bodily passage. A sheath can be introduced into a bodily passage prior, or subsequent, to the individual on which the procedure is being performed entering a sleep state.

While various steps, alternative steps, and optional steps have been described above with respect to performing a sleep study, these steps, alternative steps, and optional steps can be included in, accomplished concurrently with, and/or accomplished in the alternative to, the methodology, steps, alternative steps, and/or optional steps described above with respect to methodology 3300.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:

1. A method of performing a sleep study within an airway, the method comprising the steps of:

introducing a medical device having a proximal end and a distal end into said airway such that the distal end of the medical device is disposed within said airway, the medical device attached to a control unit, the control unit attached to a monitor, the medical device comprising:

an elongate member having an elongate member lengthwise axis, an elongate member proximal end, an elongate member distal end, and an elongate member body defining an elongate member lumen, an elongate member proximal opening, an elongate member first aperture disposed between the elongate member proximal end and the elongate member distal end, an elongate member second aperture disposed between the elongate member first aperture and the elongate member distal end, an elongate member third aperture disposed between the elongate member second aperture and the elongate member distal end, and an elongate member fourth aperture disposed between the elongate member third aperture and the elongate member distal end, the elongate member lumen extending from the elongate member proximal opening to the elongate member distal end, each of the elongate member first aperture, elongate member second aperture, elongate member third aperture, and elongate member fourth aperture extending through the elongate member body and providing access to the elongate member lumen;

a handle attached to the elongate member and having an actuator moveable between an actuator first position and an actuator second position; and a wire member having a wire member first end attached to the actuator and a wire member second end attached to the elongate member, the wire member extending from the wire member first end within the elongate member lumen to the elongate member first aperture, the wire member passing through the elongate member first aperture and extending to the elongate member second aperture, the wire member passing through the elongate member second aperture and into the elongate member lumen and extending to the elongate member third aperture, the wire member passing through the elongate member third aperture and extending to the elongate member fourth aperture, the wire member passing through the elongate member fourth aperture and into the elongate member lumen;

an imaging device attached to the elongate member and adapted to obtain one or more images; and a transducer attached to the elongate member and in signal communication with the control unit, the transducer providing a signal to the control unit in response to an event;

recording the signal provided by the transducer relative to a first interval of time;

recording the one or more images obtained by the imaging device relative to a second interval of time;

wherein the elongate member is moveable between a substantially straight configuration when the actuator is in the actuator first position and a curved configuration when the actuator is in the actuator second position;

wherein movement of the actuator from the actuator first position to the actuator second position creates tension in the wire member and results in movement of the elongate member from the substantially straight configuration to the curved configuration; and wherein the elongate member defines a first curve and a second curve when the actuator is in the actuator second position.

2. The method of claim 1, wherein the first interval of time and the second interval of time are concurrent.

3. The method of claim 2, wherein the recorded signal provided by the transducer relative to the first interval of time is displayed on the monitor in a first display region; and wherein the recorded one or more images obtained by the imaging device relative to the second interval of time are displayed on the monitor in a second display region.

4. The method of claim 3, wherein the recorded signal provided by the transducer relative to the first interval of time is displayed on the monitor relative to the first interval of time.

5. The method of claim 4, wherein the first display region includes a control that is moveable relative to the first interval of time.

6. The method of claim 5, wherein the second display region displays the one or more images obtained by the imaging device during the second interval of time as the control is moved relative to the first interval of time.

7. The method of claim 1, wherein the elongate member first aperture and the elongate member second aperture are disposed on a second elongate member axis that is parallel to the elongate member lengthwise axis; and wherein the elongate member third aperture and the elongate member fourth aperture are disposed on a third elongate member axis that is parallel to the elongate member lengthwise axis.

8. The method of claim 7, wherein each of the elongate member lengthwise axis, second elongate member axis, and third elongate member axis is disposed on a plane.

9. The method of claim 1, wherein the first interval of time and the second interval of time are consecutive.

10. The method of claim 1, wherein the event is an apneic event.

11. The method of claim 1, wherein the step of recording the signal provided by the transducer relative to a first interval of time is initiated when the transducer provides the signal to the control unit.

12. The method of claim 1, wherein the signal provided by the transducer includes a tag that indicates when the event occurs within the first interval of time.

13. A method of performing a sleep study within an airway, the method comprising the steps of:

introducing a medical device having a proximal end and a distal end into said airway such that the distal end of the medical device is disposed within said airway, the medical device attached to a control unit, the control unit attached to a monitor, the medical device comprising:

an elongate member having an elongate member lengthwise axis, an elongate member proximal end, an elongate member distal end, and an elongate member body defining an elongate member lumen, an elongate member proximal opening, an elongate member first aperture disposed between the elongate member proximal end and the elongate member distal end, an elongate member second aperture disposed between the elongate member first aperture and the elongate member distal end, an elongate member third aperture disposed between the elongate member second aperture and the elongate member distal end, and an elongate member fourth aperture disposed between the elongate member third aperture and the elongate member distal end, the elongate member lumen extending from the elongate member proximal opening to the elongate member distal end, each of the elongate member first aperture, elongate member second aperture, elongate member third aperture, and elongate member fourth aperture extending through the elongate member body and providing access to the elongate member lumen, the elongate member first aperture and the elongate member second aperture disposed on a second elongate member axis that is parallel to the elongate member lengthwise axis, the elongate member third aperture and the elongate member fourth aperture disposed on a third elongate member axis that is parallel to the elongate member lengthwise axis;

a handle attached to the elongate member and having an actuator moveable between an actuator first position and an actuator second position; and a wire member having a wire member first end attached to the actuator and a wire member second end attached to the elongate member, the wire member extending from the wire member first end within the elongate member lumen to the elongate member first aperture, the wire member passing through the elongate member first aperture and extending to the elongate member second aperture, the wire member passing through the elongate member second aperture and into the elongate member lumen and extending to the elongate member third aperture, the wire member passing through the elongate member third aperture and extending to the elongate member fourth aperture, the wire member passing through the elongate member fourth aperture and into the elongate member lumen;

an imaging device attached to the elongate member and adapted to obtain one or more images; and a transducer attached to the elongate member and in signal communication with the control unit, the transducer providing a signal to the control unit in response to an event;

recording the signal provided by the transducer relative to a first interval of time;

recording the one or more images obtained by the imaging device relative to a second interval of time, the second interval of time being concurrent with the first interval of time;

wherein the elongate member is moveable between a substantially straight configuration when the actuator is in the actuator first position and a curved configuration when the actuator is in the actuator second position;

wherein movement of the actuator from the actuator first position to the actuator second position creates tension in the wire member and results in movement of the elongate member from the substantially straight configuration to the curved configuration; and wherein the elongate member defines a first curve and a second curve when the actuator is in the actuator second position.

14. The method of claim 13, wherein the recorded signal provided by the transducer relative to the first interval of time is displayed on the monitor in a first display region; and
wherein the recorded one or more images obtained by the imaging device relative to the second interval of time are displayed on the monitor in a second display region.

15. The method of claim 14, wherein the recorded signal provided by the transducer relative to the first interval of time is displayed on the monitor relative to the first interval of time.

16. The method of claim 15, wherein the first display region includes a control that is moveable relative to the first interval of time.

17. The method of claim 16, wherein the second display region displays the one or more images obtained by the imaging device during the second interval of time as the control is moved relative to the first interval of time.

18. The method of claim 13, wherein each of the elongate member lengthwise axis, second elongate member axis, and third elongate member axis is disposed on a plane.

19. The method of claim 13, wherein the event is an apneic event.

20. A method of performing a sleep study within an airway, the method comprising the steps of:

introducing a medical device having a proximal end and a distal end into said airway such that the distal end of the medical device is disposed within said airway, the medical device attached to a control unit, the control unit attached to a monitor, the medical device comprising:

an elongate member having an elongate member lengthwise axis, an elongate member proximal end, an elongate member distal end, and an elongate member body defining an elongate member lumen, an elongate member proximal opening, an elongate member first aperture disposed between the elongate member proximal end and the elongate member distal end, an elongate member second aperture disposed between the elongate member first aperture and the elongate member distal end, an elongate member third aperture disposed between the elongate member second aperture and the elongate member distal end, and an elongate member fourth aperture disposed between the elongate member third aperture and the elongate member distal end, the elongate member lumen extending from the elongate member proximal opening to the elongate member distal end, each of the elongate member first aperture, elongate member second aperture, elongate member third aperture, and elongate member fourth aperture extending through the elongate member body and providing access to the elongate member lumen, the elongate member first aperture and the elongate member second aperture disposed on a second elongate member axis that is parallel to the elongate member lengthwise axis, the elongate member third aperture and the elongate member fourth aperture disposed on a third elongate member axis that is parallel to the elongate member lengthwise axis;

a handle attached to the elongate member and having an actuator moveable between an actuator first position and an actuator second position; and a wire member having a wire member first end attached to the actuator and a wire member second end attached to the elongate member, the wire member extending from the wire member first end within the elongate member lumen to the elongate member first aperture, the wire member passing through the elongate member first aperture and extending to the elongate member second aperture, the wire member passing through the elongate member second aperture and into the elongate member lumen and extending to the elongate member third aperture, the wire member passing through the elongate member third aperture and extending to the elongate member fourth aperture, the wire member passing through the elongate member fourth aperture and into the elongate member lumen;

an imaging device attached to the elongate member and adapted to obtain one or more images; and a transducer attached to the elongate member and in signal communication with the control unit, the transducer providing a signal to the control unit in response to an event;

recording the signal provided by the transducer relative to a first interval of time, the recorded signal provided by the transducer relative to the first interval of time being displayed on the monitor in a first display region;

recording the one or more images obtained by the imaging device relative to a second interval of time, the second interval of time being concurrent with the first interval of time, the recorded one or more images obtained by the imaging device relative to the second interval of time being displayed on the monitor in a second display region;

wherein the elongate member is moveable between a substantially straight configuration when the actuator is in the actuator first position and a curved configuration when the actuator is in the actuator second position;

wherein movement of the actuator from the actuator first position to the actuator second position creates tension in the wire member and results in movement of the elongate member from the substantially straight configuration to the curved configuration;

wherein the elongate member defines a first curve and a second curve when the actuator is in the actuator second position; and wherein each of the elongate member lengthwise axis, second elongate member axis, and third elongate member axis is disposed on a plane.

* * * * *